United States Patent
Yacoby et al.

(10) Patent No.: US 10,478,594 B2
(45) Date of Patent: Nov. 19, 2019

(54) APPARATUS AND METHODS FOR DELIVERING DEVICES FOR REDUCING LEFT ATRIAL PRESSURE

(71) Applicant: V-Wave Ltd., Caesarea (IL)

(72) Inventors: Menashe Yacoby, Ramat Gan (IL); Boaz Harari, Tel-Aviv (IL); Yaacov Nitzan, Herzliya (IL)

(73) Assignee: V-Wave Ltd., Caesarea (IL)

( * ) Notice: Subject to any disclaimer, the term of this patent is extended or adjusted under 35 U.S.C. 154(b) by 245 days.

(21) Appl. No.: 15/656,936

(22) Filed: Jul. 21, 2017

(65) Prior Publication Data

US 2017/0319823 A1    Nov. 9, 2017

Related U.S. Application Data

(63) Continuation of application No. 14/282,615, filed on May 20, 2014, now Pat. No. 9,713,696.
(Continued)

(51) Int. Cl.
*A61F 11/00* (2006.01)
*A61M 25/01* (2006.01)
(Continued)

(52) U.S. Cl.
CPC ..... *A61M 25/0102* (2013.01); *A61B 17/0057* (2013.01); *A61B 17/3415* (2013.01);
(Continued)

(58) Field of Classification Search
CPC . A61B 17/29; A61B 17/0057; A61B 17/3415; A61B 2017/00243;
(Continued)

(56) References Cited

U.S. PATENT DOCUMENTS 3,852,334 A   12/1974 Dusza et al.
3,874,388 A    4/1975 King et al.
(Continued)

FOREIGN PATENT DOCUMENTS

EP    2 238 933 A1   10/2010
FR    2827153 A1     1/2003
(Continued)

OTHER PUBLICATIONS

Ando et al., "Left ventricular decompression through a patent foramen ovale in a patient with hypertropic cardiomyopathy: A case report," Cardiovascular Ultrasound 2: 1-7 (2004).
(Continued)

*Primary Examiner* — Amy R Weisberg
(74) *Attorney, Agent, or Firm* — Eversheds Sutherland (US) LLP; Christopher C. Bolten; Nicola A. Pisano

(57) ABSTRACT

A device for regulating blood pressure between a patient's left atrium and right atrium, and apparatus for delivery the device, are provided. The delivery apparatus may include one or more latching legs, a release ring, a pull chord, and a catheter wherein the latching legs are configured to engage the device for delivery. The inventive devices may reduce left atrial pressure and left ventricular end diastolic pressure, and may increase cardiac output, increase ejection fraction, relieve pulmonary congestion, and lower pulmonary artery pressure, among other benefits. The inventive devices may be used, for example, to treat subjects having heart failure, pulmonary congestion, or myocardial infarction, among other pathologies.

20 Claims, 30 Drawing Sheets

Related U.S. Application Data

(60) Provisional application No. 61/825,931, filed on May 21, 2013.

(51) Int. Cl.

| | | |
|---|---|---|
| *A61B 17/34* | (2006.01) | |
| *A61M 27/00* | (2006.01) | |
| *A61B 17/00* | (2006.01) | |
| *A61F 2/24* | (2006.01) | |
| *A61B 17/12* | (2006.01) | |

(52) U.S. Cl.
CPC .......... *A61F 2/2418* (2013.01); *A61F 2/2436* (2013.01); *A61M 27/002* (2013.01); *A61B 2017/00243* (2013.01); *A61B 2017/00526* (2013.01); *A61B 2017/00575* (2013.01); *A61B 2017/00592* (2013.01); *A61B 2017/00597* (2013.01); *A61B 2017/00601* (2013.01); *A61B 2017/00606* (2013.01); *A61B 2017/00623* (2013.01); *A61B 2017/12054* (2013.01)

(58) Field of Classification Search
CPC .......................................... A61B 2017/00575; A61B 2017/00597; A61B 2017/00601; A61B 2017/00623; A61B 2017/00526; A61B 2017/12054; A61B 2017/00592; A61B 2017/00606; A61M 25/0102; A61M 27/002; A61F 2/2436; A61F 2/2418
See application file for complete search history.

(56) References Cited

U.S. PATENT DOCUMENTS

| | | | |
|---|---|---|---|
| 3,952,334 A | 4/1976 | Bokros et al. | |
| 4,601,309 A | 7/1986 | Chang | |
| 4,617,932 A | 10/1986 | Kornberg | |
| 4,662,355 A | 5/1987 | Pieronne et al. | |
| 4,705,507 A | 11/1987 | Boyles | |
| 4,836,204 A | 6/1989 | Landymore et al. | |
| 4,979,955 A | 12/1990 | Smith | |
| 4,988,339 A | 1/1991 | Vadher | |
| 4,995,857 A | 2/1991 | Arnold | |
| 5,035,706 A | 7/1991 | Giantureo et al. | |
| 5,186,431 A | 2/1993 | Tamari | |
| 5,267,940 A | 12/1993 | Moulder | |
| 5,290,227 A | 3/1994 | Pasque | |
| 5,312,341 A | 5/1994 | Turi | |
| 5,326,374 A | 7/1994 | Ilbawi et al. | |
| 5,332,402 A | 7/1994 | Teitelbaum | |
| 5,334,217 A | 8/1994 | Das | |
| 5,409,019 A | 4/1995 | Wilk | |
| 5,429,144 A | 7/1995 | Wilk | |
| 5,500,015 A | 3/1996 | Deac | |
| 5,531,759 A | 7/1996 | Kensey et al. | |
| 5,556,386 A | 9/1996 | Todd | |
| 5,584,803 A | 12/1996 | Stevens et al. | |
| 5,597,377 A | 1/1997 | Aldea | |
| 5,645,559 A | 7/1997 | Hachtman et al. | |
| 5,655,548 A | 8/1997 | Nelson et al. | |
| 5,662,711 A | 9/1997 | Douglas | |
| 5,702,412 A | 12/1997 | Popov et al. | |
| 5,725,552 A | 3/1998 | Kotula et al. | |
| 5,779,716 A | 7/1998 | Cano et al. | |
| 5,795,307 A | 8/1998 | Krueger | |
| 5,810,836 A | 9/1998 | Hussein et al. | |
| 5,824,062 A | 10/1998 | Patke et al. | |
| 5,824,071 A | 10/1998 | Nelson et al. | |
| 5,910,144 A * | 6/1999 | Hayashi ............... | A61B 17/221 606/108 |
| 5,916,193 A | 6/1999 | Stevens et al. | |
| 5,941,850 A | 8/1999 | Shah et al. | |
| 5,957,949 A | 9/1999 | Leonhardt et al. | |
| 6,027,518 A | 2/2000 | Gaber | |
| 6,039,755 A | 3/2000 | Edwin et al. | |
| 6,039,759 A | 3/2000 | Carpentier et al. | |
| 6,086,610 A | 7/2000 | Duerig et al. | |
| 6,117,159 A | 9/2000 | Huebsch et al. | |
| 6,120,534 A | 9/2000 | Ruiz | |
| 6,124,523 A | 9/2000 | Banas et al. | |
| 6,126,686 A | 10/2000 | Badylak et al. | |
| 6,165,188 A | 12/2000 | Saadat et al. | |
| 6,210,318 B1 | 4/2001 | Lederman | |
| 6,214,039 B1 | 4/2001 | Banas et al. | |
| 6,217,541 B1 | 4/2001 | Yu | |
| 6,221,096 B1 | 4/2001 | Aiba et al. | |
| 6,242,762 B1 | 6/2001 | Brown et al. | |
| 6,245,099 B1 | 6/2001 | Edwin et al. | |
| 6,254,564 B1 | 7/2001 | Wilk et al. | |
| 6,260,552 B1 | 7/2001 | Mortier et al. | |
| 6,264,684 B1 | 7/2001 | Banas et al. | |
| 6,270,526 B1 | 8/2001 | Cox | |
| 6,277,078 B1 | 8/2001 | Porat et al. | |
| 6,302,892 B1 | 10/2001 | Wilk | |
| 6,328,699 B1 | 12/2001 | Eigler et al. | |
| 6,344,022 B1 | 2/2002 | Jarvik | |
| 6,358,277 B1 | 3/2002 | Duran | |
| 6,398,803 B1 | 6/2002 | Layne et al. | |
| 6,406,422 B1 | 6/2002 | Landesberg | |
| 6,447,539 B1 | 9/2002 | Nelson et al. | |
| 6,451,051 B2 | 9/2002 | Drasler et al. | |
| 6,458,153 B1 | 10/2002 | Bailey et al. | |
| 6,468,303 B1 | 10/2002 | Amplatz et al. | |
| 6,475,136 B1 | 11/2002 | Forsell | |
| 6,478,776 B1 | 11/2002 | Rosenman et al. | |
| 6,491,705 B2 | 12/2002 | Gifford et al. | |
| 6,527,698 B1 | 3/2003 | Kung et al. | |
| 6,544,208 B2 | 4/2003 | Ethier et al. | |
| 6,562,066 B1 | 5/2003 | Martin | |
| 6,572,652 B2 | 6/2003 | Shaknovich | |
| 6,579,314 B1 | 6/2003 | Lombardi et al. | |
| 6,589,198 B1 | 7/2003 | Soltanpour et al. | |
| 6,632,169 B2 | 10/2003 | Korakianitis et al. | |
| 6,638,303 B1 | 10/2003 | Campbell | |
| 6,641,610 B2 | 11/2003 | Wolf et al. | |
| 6,652,578 B2 | 11/2003 | Bailey et al. | |
| 6,685,664 B2 | 2/2004 | Levin et al. | |
| 6,712,836 B1 | 3/2004 | Berg et al. | |
| 6,740,115 B2 | 5/2004 | Lombardi et al. | |
| 6,758,858 B2 | 7/2004 | McCrea et al. | |
| 6,764,507 B2 | 7/2004 | Shanley et al. | |
| 6,770,087 B2 | 8/2004 | Layne et al. | |
| 6,797,217 B2 | 9/2004 | McCrea et al. | |
| 7,001,409 B2 | 2/2006 | Amplatz | |
| 7,004,966 B2 | 2/2006 | Edwin et al. | |
| 7,060,150 B2 | 6/2006 | Banas et al. | |
| 7,083,640 B2 | 8/2006 | Lombardi et al. | |
| 7,149,587 B2 | 12/2006 | Wardle et al. | |
| 7,169,160 B1 | 1/2007 | Middleman et al. | |
| 7,169,172 B2 * | 1/2007 | Levine ............ | A61F 2/95 623/1.11 |
| 7,208,010 B2 | 4/2007 | Shanley et al. | |
| 7,226,558 B2 | 6/2007 | Nieman et al. | |
| 7,294,115 B1 | 11/2007 | Wilk | |
| 7,306,756 B2 | 12/2007 | Edwin et al. | |
| 7,468,071 B2 | 12/2008 | Edwin et al. | |
| 7,578,899 B2 | 8/2009 | Edwin et al. | |
| 7,794,473 B2 | 9/2010 | Tessmer et al. | |
| 7,842,083 B2 | 11/2010 | Shanley et al. | |
| 7,914,639 B2 | 3/2011 | Layne et al. | |
| 7,939,000 B2 | 5/2011 | Edwin et al. | |
| 7,988,724 B2 | 8/2011 | Salahieh et al. | |
| 7,993,383 B2 | 8/2011 | Hartley et al. | |
| 8,012,194 B2 | 9/2011 | Edwin et al. | |
| 8,016,877 B2 | 9/2011 | Seguin et al. | |
| 8,025,668 B2 | 9/2011 | McCartney | |
| 8,043,360 B2 | 10/2011 | McNamara et al. | |
| 8,070,708 B2 | 12/2011 | Rottenberg et al. | |
| 8,091,556 B2 | 1/2012 | Keren et al. | |
| 8,096,959 B2 | 1/2012 | Stewart et al. | |
| 8,137,605 B2 | 3/2012 | McCrea et al. | |
| 8,147,545 B2 | 4/2012 | Avior | |

(56) References Cited

U.S. PATENT DOCUMENTS

| | | | |
|---|---|---|---|
| 8,157,852 B2 * | 4/2012 | Bloom | A61F 2/2412 623/1.11 |
| 8,157,860 B2 | 4/2012 | McNamara et al. | |
| 8,157,940 B2 | 4/2012 | Edwin et al. | |
| 8,158,041 B2 | 4/2012 | Colone | |
| 8,187,321 B2 | 5/2012 | Shanley et al. | |
| 8,202,313 B2 | 6/2012 | Shanley et al. | |
| 8,206,435 B2 | 6/2012 | Shanley et al. | |
| 8,235,916 B2 | 8/2012 | Whiting et al. | |
| 8,235,933 B2 | 8/2012 | Keren et al. | |
| 8,246,677 B2 | 8/2012 | Ryan | |
| 8,298,244 B2 | 10/2012 | Garcia et al. | |
| 8,303,511 B2 | 11/2012 | Eigler et al. | |
| 8,313,524 B2 | 11/2012 | Edwin et al. | |
| 8,328,751 B2 | 12/2012 | Keren et al. | |
| 8,337,650 B2 | 12/2012 | Edwin et al. | |
| 8,348,996 B2 | 1/2013 | Tuval et al. | |
| 8,398,708 B2 | 3/2013 | Meiri et al. | |
| 8,460,366 B2 | 6/2013 | Rowe | |
| 8,468,667 B2 | 6/2013 | Straubinger et al. | |
| 8,579,966 B2 | 11/2013 | Seguin et al. | |
| 8,597,225 B2 | 12/2013 | Kapadia | |
| 8,617,337 B2 | 12/2013 | Layne et al. | |
| 8,617,441 B2 | 12/2013 | Edwin et al. | |
| 8,652,284 B2 | 2/2014 | Bogert et al. | |
| 8,696,611 B2 | 4/2014 | Nitzan et al. | |
| 8,790,241 B2 | 7/2014 | Edwin et al. | |
| 8,882,798 B2 * | 11/2014 | Schwab | A61F 5/0036 606/205 |
| 8,911,489 B2 | 12/2014 | Ben-Muvhar | |
| 9,034,034 B2 | 5/2015 | Nitzan et al. | |
| 9,067,050 B2 | 6/2015 | Gallagher et al. | |
| 9,358,371 B2 | 6/2016 | McNamara et al. | |
| 9,393,115 B2 * | 7/2016 | Tabor | A61F 2/2412 |
| 9,456,812 B2 * | 10/2016 | Finch | A61B 17/0057 |
| 9,622,895 B2 * | 4/2017 | Cohen | A61F 2/95 |
| 9,629,715 B2 | 4/2017 | Nitzan et al. | |
| 9,681,948 B2 | 6/2017 | Levi et al. | |
| 9,707,382 B2 | 7/2017 | Nitzan et al. | |
| 9,713,696 B2 | 7/2017 | Yacoby et al. | |
| 9,980,815 B2 | 5/2018 | Nitzan et al. | |
| 10,076,403 B1 | 9/2018 | Eigler et al. | |
| 10,207,087 B2 | 2/2019 | Keren et al. | |
| 2002/0120277 A1 * | 8/2002 | Hauschild | A61B 17/221 606/108 |
| 2002/0165479 A1 | 11/2002 | Wilk | |
| 2002/0165606 A1 | 11/2002 | Wolf et al. | |
| 2002/0169371 A1 | 11/2002 | Gilderdale | |
| 2002/0169377 A1 | 11/2002 | Khairkhahan et al. | |
| 2002/0173742 A1 | 11/2002 | Keren et al. | |
| 2003/0100920 A1 | 5/2003 | Akin et al. | |
| 2003/0125798 A1 | 7/2003 | Martin | |
| 2003/0136417 A1 | 7/2003 | Fonseca et al. | |
| 2003/0176914 A1 | 9/2003 | Rabkin et al. | |
| 2003/0209835 A1 | 11/2003 | Chun et al. | |
| 2003/0216679 A1 | 11/2003 | Wolf et al. | |
| 2004/0010219 A1 | 1/2004 | McCusker et al. | |
| 2004/0016514 A1 | 1/2004 | Nien | |
| 2004/0077988 A1 | 4/2004 | Tweden et al. | |
| 2004/0088045 A1 | 5/2004 | Cox | |
| 2004/0093075 A1 | 5/2004 | Kuehne | |
| 2004/0102797 A1 | 5/2004 | Golden et al. | |
| 2004/0116999 A1 | 6/2004 | Ledergerber | |
| 2004/0138743 A1 | 7/2004 | Myers et al. | |
| 2004/0147869 A1 | 7/2004 | Wolf et al. | |
| 2004/0147871 A1 | 7/2004 | Burnett | |
| 2004/0147886 A1 | 7/2004 | Bonni | |
| 2004/0162514 A1 | 8/2004 | Alferness et al. | |
| 2004/0193261 A1 | 9/2004 | Berreklouw | |
| 2004/0210190 A1 | 10/2004 | Kohler et al. | |
| 2004/0210307 A1 | 10/2004 | Khairkhahan | |
| 2004/0225352 A1 | 11/2004 | Osborne et al. | |
| 2005/0003327 A1 | 1/2005 | Elian et al. | |
| 2005/0033351 A1 | 2/2005 | Newton | |
| 2005/0065589 A1 | 3/2005 | Schneider et al. | |
| 2005/0137682 A1 | 6/2005 | Justino | |
| 2005/0148925 A1 | 7/2005 | Rottenberg et al. | |
| 2005/0165344 A1 | 7/2005 | Dobak, III | |
| 2005/0182486 A1 | 8/2005 | Gabbay | |
| 2005/0283231 A1 | 12/2005 | Haug et al. | |
| 2006/0009800 A1 | 1/2006 | Christianson et al. | |
| 2006/0025857 A1 | 2/2006 | Bergheim et al. | |
| 2006/0111660 A1 | 5/2006 | Wolf et al. | |
| 2006/0116710 A1 | 6/2006 | Corcoran et al. | |
| 2006/0122647 A1 | 6/2006 | Callaghan et al. | |
| 2006/0167541 A1 | 7/2006 | Lattouf | |
| 2006/0212110 A1 | 9/2006 | Osborne et al. | |
| 2006/0256611 A1 | 11/2006 | Bednorz et al. | |
| 2006/0282157 A1 | 12/2006 | Hill et al. | |
| 2007/0010852 A1 | 1/2007 | Blaeser et al. | |
| 2007/0043435 A1 | 2/2007 | Seguin et al. | |
| 2007/0213813 A1 | 9/2007 | Von Segesser et al. | |
| 2007/0276413 A1 | 11/2007 | Nobles | |
| 2007/0276414 A1 | 11/2007 | Nobles | |
| 2007/0282157 A1 | 12/2007 | Rottenberg et al. | |
| 2007/0299384 A1 | 12/2007 | Faul et al. | |
| 2008/0086205 A1 | 4/2008 | Gordy et al. | |
| 2008/0177300 A1 | 7/2008 | Mas et al. | |
| 2008/0262602 A1 | 10/2008 | Wilk et al. | |
| 2009/0054976 A1 * | 2/2009 | Tuval | A61F 2/0095 623/2.11 |
| 2009/0125104 A1 | 5/2009 | Hoffman | |
| 2009/0276040 A1 | 11/2009 | Rowe et al. | |
| 2009/0319037 A1 | 12/2009 | Rowe et al. | |
| 2010/0004740 A1 | 1/2010 | Seguin et al. | |
| 2010/0057192 A1 | 3/2010 | Celermajer | |
| 2010/0081867 A1 * | 4/2010 | Fishier | A61B 17/00234 600/37 |
| 2010/0121434 A1 | 5/2010 | Paul et al. | |
| 2010/0179590 A1 | 7/2010 | Fortson et al. | |
| 2010/0191326 A1 | 7/2010 | Alkhatib | |
| 2010/0249909 A1 | 9/2010 | McNamara et al. | |
| 2010/0249910 A1 | 9/2010 | McNamara et al. | |
| 2010/0249915 A1 | 9/2010 | Zhang | |
| 2010/0256548 A1 | 10/2010 | McNamara et al. | |
| 2010/0256753 A1 | 10/2010 | McNamara et al. | |
| 2010/0298755 A1 | 11/2010 | McNamara et al. | |
| 2011/0022157 A1 | 1/2011 | Essinger et al. | |
| 2011/0054515 A1 | 3/2011 | Bridgeman et al. | |
| 2011/0071623 A1 | 3/2011 | Finch et al. | |
| 2011/0071624 A1 | 3/2011 | Finch et al. | |
| 2011/0152923 A1 | 6/2011 | Fox | |
| 2011/0218479 A1 | 9/2011 | Rottenberg et al. | |
| 2011/0218480 A1 | 9/2011 | Rottenberg et al. | |
| 2011/0218481 A1 | 9/2011 | Rottenberg et al. | |
| 2011/0257723 A1 | 10/2011 | McNamara | |
| 2011/0264203 A1 | 10/2011 | Dwork et al. | |
| 2011/0295182 A1 | 12/2011 | Finch et al. | |
| 2011/0295362 A1 | 12/2011 | Finch et al. | |
| 2011/0295366 A1 | 12/2011 | Finch et al. | |
| 2011/0306916 A1 | 12/2011 | Nitzan et al. | |
| 2012/0022633 A1 | 1/2012 | Olson et al. | |
| 2012/0071918 A1 | 3/2012 | Amin et al. | |
| 2012/0130301 A1 | 5/2012 | McNamara et al. | |
| 2012/0165928 A1 | 6/2012 | Nitzan et al. | |
| 2012/0179172 A1 | 7/2012 | Paul et al. | |
| 2012/0265296 A1 | 10/2012 | McNamara et al. | |
| 2012/0271398 A1 | 10/2012 | Essinger et al. | |
| 2013/0030521 A1 * | 1/2013 | Nitzan | A61B 17/0057 623/2.13 |
| 2013/0046373 A1 | 2/2013 | Cartledge et al. | |
| 2013/0138145 A1 | 5/2013 | Von Oepen | |
| 2013/0178783 A1 | 7/2013 | McNamara et al. | |
| 2013/0178784 A1 | 7/2013 | McNamara et al. | |
| 2013/0184634 A1 | 7/2013 | McNamara et al. | |
| 2013/0197423 A1 | 8/2013 | Keren et al. | |
| 2013/0197547 A1 | 8/2013 | Fukuoka et al. | |
| 2013/0197629 A1 | 8/2013 | Gainor et al. | |
| 2013/0204175 A1 | 8/2013 | Sugimoto | |
| 2013/0231737 A1 | 9/2013 | McNamara et al. | |
| 2013/0281988 A1 | 10/2013 | Magnin et al. | |
| 2014/0012368 A1 | 1/2014 | Sugimoto et al. | |
| 2014/0067037 A1 * | 3/2014 | Fargahi | A61F 2/966 623/1.12 |

(56) References Cited

U.S. PATENT DOCUMENTS

| | | |
|---|---|---|
| 2014/0094904 A1 | 4/2014 | Salahieh et al. |
| 2014/0128795 A1 | 5/2014 | Keren et al. |
| 2014/0128796 A1 | 5/2014 | Keren et al. |
| 2014/0163449 A1 | 6/2014 | Rottenberg et al. |
| 2014/0213959 A1 | 7/2014 | Nitzan et al. |
| 2014/0249621 A1 | 9/2014 | Eidenschink |
| 2014/0277045 A1 | 9/2014 | Fazio et al. |
| 2014/0277054 A1 | 9/2014 | McNamara et al. |
| 2014/0303710 A1 | 10/2014 | Zhang et al. |
| 2014/0350565 A1 | 11/2014 | Yacoby et al. |
| 2014/0350661 A1* | 11/2014 | Schaeffer ............... A61F 2/2436 623/1.24 |
| 2014/0350669 A1 | 11/2014 | Gillespie et al. |
| 2014/0357946 A1 | 12/2014 | Golden et al. |
| 2015/0039084 A1 | 2/2015 | Levi et al. |
| 2015/0066140 A1 | 3/2015 | Quadri et al. |
| 2015/0073539 A1 | 3/2015 | Geiger et al. |
| 2015/0127093 A1 | 5/2015 | Hosmer et al. |
| 2015/0142049 A1 | 5/2015 | Delgado et al. |
| 2015/0148896 A1 | 5/2015 | Karapetian et al. |
| 2015/0157455 A1 | 6/2015 | Hoang et al. |
| 2015/0173897 A1 | 6/2015 | Raanani et al. |
| 2015/0182334 A1 | 7/2015 | Bourang et al. |
| 2015/0190229 A1 | 7/2015 | Seguin |
| 2015/0201998 A1 | 7/2015 | Roy et al. |
| 2015/0209143 A1 | 7/2015 | Duffy et al. |
| 2015/0230924 A1 | 8/2015 | Miller et al. |
| 2015/0238314 A1* | 8/2015 | Bortlein ................ A61F 2/2427 623/2.11 |
| 2015/0245908 A1 | 9/2015 | Nitzan et al. |
| 2015/0272731 A1 | 10/2015 | Racchini et al. |
| 2015/0282790 A1 | 10/2015 | Quinn et al. |
| 2015/0282931 A1 | 10/2015 | Brunnett et al. |
| 2016/0157862 A1 | 6/2016 | Hernandez et al. |
| 2016/0206423 A1 | 7/2016 | O'Connor et al. |
| 2016/0213467 A1 | 7/2016 | Backus et al. |
| 2016/0220360 A1 | 8/2016 | Lin et al. |
| 2016/0220365 A1 | 8/2016 | Backus et al. |
| 2016/0262878 A1 | 9/2016 | Backus et al. |
| 2016/0262879 A1 | 9/2016 | Meiri et al. |
| 2016/0287386 A1 | 10/2016 | Alon et al. |
| 2016/0296325 A1 | 10/2016 | Edelman et al. |
| 2016/0361167 A1* | 12/2016 | Tuval .................... A61F 2/0095 |
| 2016/0361184 A1 | 12/2016 | Tabor et al. |

FOREIGN PATENT DOCUMENTS

| | | |
|---|---|---|
| WO | WO-99/60941 A1 | 12/1999 |
| WO | WO-00/44311 A2 | 8/2000 |
| WO | WO-02/071974 A2 | 9/2002 |
| WO | WO-03/053495 A2 | 7/2003 |
| WO | WO-2005/027752 A1 | 3/2005 |
| WO | WO-2005/074367 A1 | 8/2005 |
| WO | WO-2006/127765 | 11/2006 |
| WO | WO-2007/083288 A2 | 7/2007 |
| WO | WO-2008/055301 A1 | 5/2008 |
| WO | WO-2009/029261 A1 | 3/2009 |
| WO | WO-2010/128501 A1 | 11/2010 |
| WO | WO-2011/062858 A1 | 5/2011 |
| WO | WO-2013/096965 A1 | 6/2013 |
| WO | WO-2016/178171 A1 | 11/2016 |

OTHER PUBLICATIONS

Braunwald, Heart Disease, Chapter 6, p. 186.
Bridges, et al., The Society of Thoracic Surgeons Practice Guideline Series: Transmyocardial Laser Revascularization, Ann Thorac Surg., 77:1494-1502 (2004).
Bristow et al., "Improvement in cardiac myocyte function by biological effects of medical therapy: a new concept in the treatment of heart failure," European Heart Journal 16(Suppl.F): 20-31 (1995).
Case et al., "Relief of High Left-Atrial Pressure in Left-Ventricular Failure," Lancet, pp. 841-842 (Oct. 14, 1964).
Coats et al., "Controlled trial of physical training in chronic heart failure: Exercise performance, hemodynamics, ventilation and autonomic function," Circulation 85:2119-2131 (1992).
Davies et al., "Reduced contraction and altered frequency response of isolated ventricular myocytes from patients with heart failure," Circulation 92: 2540-2549 (1995).
Ennezat et al., "An unusual case of low-flow, low-gradient severe aortic stenosis: Left-to-right shunt due to atrial septal defect," Cardiology 113(2): 146-148 (2009).
Ewert et al., "Acute left heart failure after interventional occlusion of an atrial septal defect," Z Kardiol. 90(5): 362-366 (May 2001).
Ewert, et al., Masked Left Ventricular Restriction in Elderly Patients with Atrial Septal Defects: A Contraindication for Closure, Catherization and Cardiovascular Interventions, 52:177-180 (2001).
Geiran et al., "Changes in cardiac dynamics by opening an interventricular shunt in dogs," J. Surg. Res. 48(1): 6-12 (Jan. 1990).
Gelernter-Yaniv et al., "Transcatheter closure of left-to-right interatrial shunts to resolve hypoxemia," Conginit. Heart Dis. 31(1) 47-53 (Jan. 2008).
Gewillig et al., "Creation with a stent of an unrestrictive lasting atrial communication," Cardio. Young 12(4): 404-407 (2002).
International Search Report for PCT/IL2005/000131, 3 pages (dated Apr. 7, 2008).
International Search Report for PCT/IL2010/000354 dated Aug. 25, 2010 (1 pg).
International Search Report & Written Opinion dated Feb. 16, 2015 in Int'l PCT Patent Appl. Serial No. PCT/162014/001771.
Khositseth et al., Transcatheter Amplatzer Device Closure of Atrial Septal Defect and Patent Foramen Ovale in Patients With Presumed Paradoxical Embolism, Mayo Clinic Proc., 79:35-41 (2004).
Kramer et al., "Controlled study of captopril in chronic heart failure: A rest and exercise hemodynamic study," Circulation 67(4): 807-816 (1983).
Lai et al., "Bidirectional shunt through a residual atrial septal defect after percutaneous transvenous mitral commissurotomy," Cardiology 83(3): 205-207 (1993).
Lemmer et al., "Surgical implications of atrial septal defect complicating aortic balloon valvuloplasty," Ann Thorac. Surg. 48(2): 295-297 (Aug. 1989).
Merriam-Webster "Definition of 'Chamber'," OnLine Dictionary 2004, Abstract.
Park Blade Septostomy Catheter Instructions for Use, Cook Medical, 28 pages, Oct. 2015.
Park, et al., Blade Atrial Septostomy: Collaborative Study, Circulation, 66(2):258-266 (1982).
Roven et al., "Effect of Compromising Right Ventricular Function in Left Ventricular Failure by Means of Interatrial and Other Shunts," American Journal Cardiology, 24:209-219 (1969).
Salehian et al., Improvements in Cardiac Form and Function After Transcatheter Closure of Secundum Atrial Septal Defects, Journal of the American College of Cardiology, 45(4):499-504 (2005).
Schmitto et al., Chronic heart failure induced by multiple sequential coronary microembolization in sheep, The International Journal of Artificial Organs, 31(4):348-353 (2008).
Schubert et al., "Left ventricular conditioning in the elderly patient to prevent congestive heart failure after transcatheter closure of the atrial septal defect," Catheterization and Cardiovascular Interventions 64(3): 333-337 (2005).
Stormer et al., "Comparative study of in vitro flow characteristics between a human aortic valve and a designed aortic valve and six corresponding types of prosthetic heart valves," European Surgical Research 8(2): 117-131 (1976).
Stumper et al., "Modified technique of stent fenestration of the atrial septum," Heart 89:1227-1230 (2003).
Trainor et al., Comparative Pathology of an Implantable Left Atrial Pressure Sensor, ASAIO Journal, Clinical Cardiovascular/Cardiopulmonary Bypass, 59(5):486-92 (2013).
Zhou et al., Unidirectional Valve Patch for Repair of Cardiac Septal Defects With Pulmonary Hypertension, Annals of Thoracic Surgeons, 60:1245-1249 (1995).
Atrium Advanta V12, Balloon Expandable Covered Stent, Improving Patient Outcomes with An Endovascular Approach, Brochure—8 pages, Getinge (2017).

(56) References Cited

OTHER PUBLICATIONS

Communication Relating to Results of the Partial International Search dated Aug. 17, 2017 in Int'l PCT Patent Appl. Serial No. PCT/162017/053188.
Eigler, et al., Implantation and Recovery of Temporary Metallic Stents in Canine Coronary Arteries, JACC, 22(4):1207-1213 (1993).
Hasenfub et al., A Transcatheter Shunt Device for Heart Failure with Preserved Ejection Fraction (REDUCE LAP-HF): A Multicentre, Open-Label, Single-Arm, Phase 1 Trial, www.thelancet.com, 387:1298-1304 (2016).
International Search Report & Written Opinion dated May 29, 2018 in Int'l PCT Patent Appl. Serial No. PCTIB2018/051355.
Rossignol et al., Left-to-Right Atrial Shunting: New Hope for Heart Failure, www.thelancet.com, 387:1253-1255 (2016)

\* cited by examiner

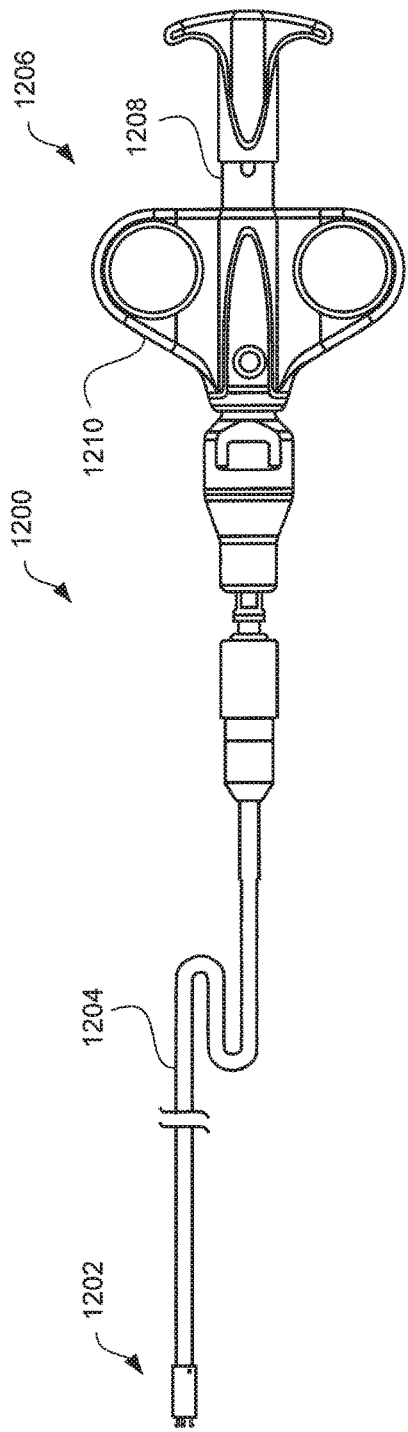 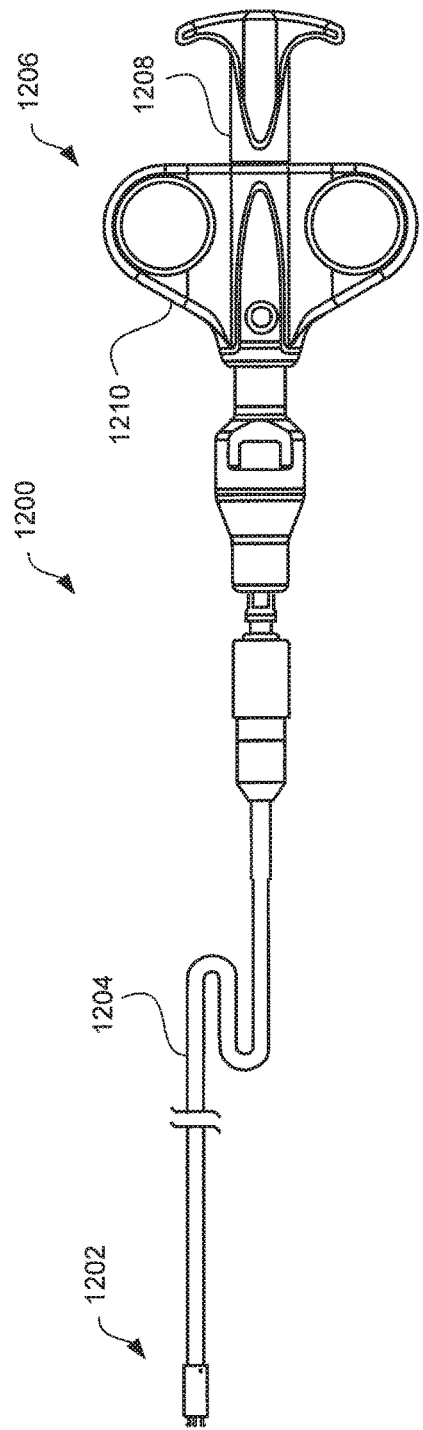
FIG. 12A
FIG. 12B

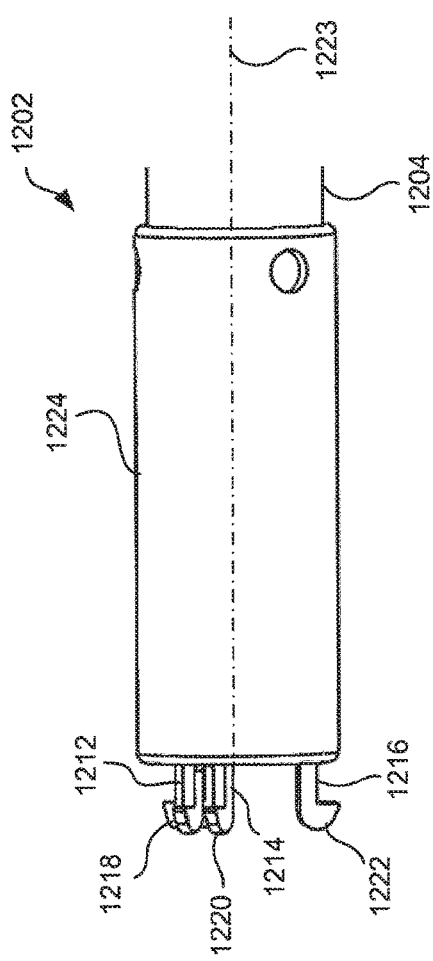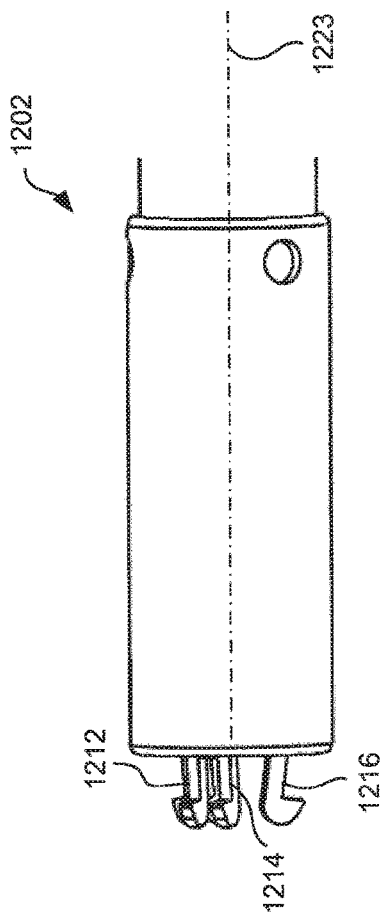
FIG. 13A
FIG. 13B

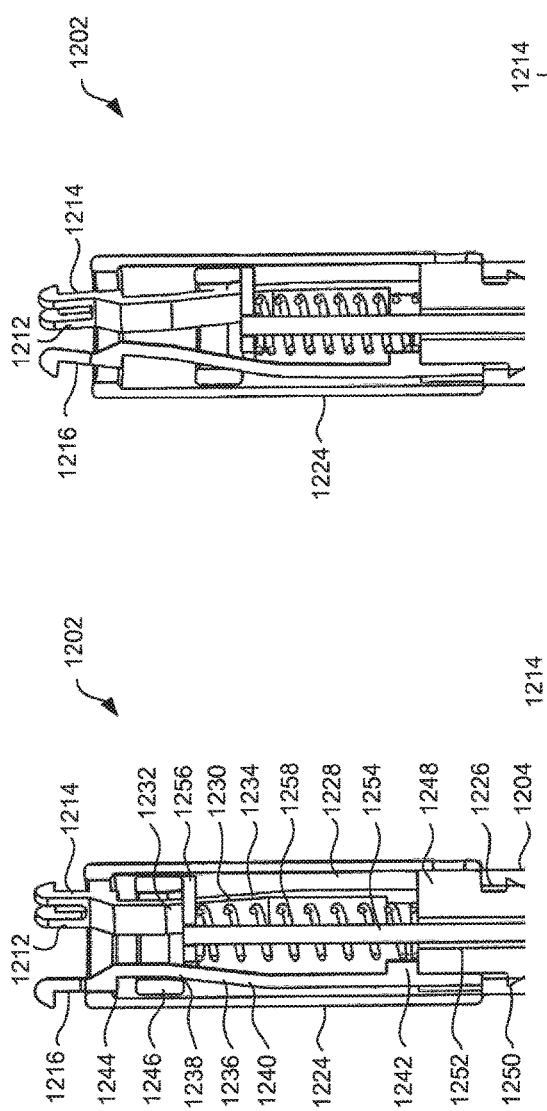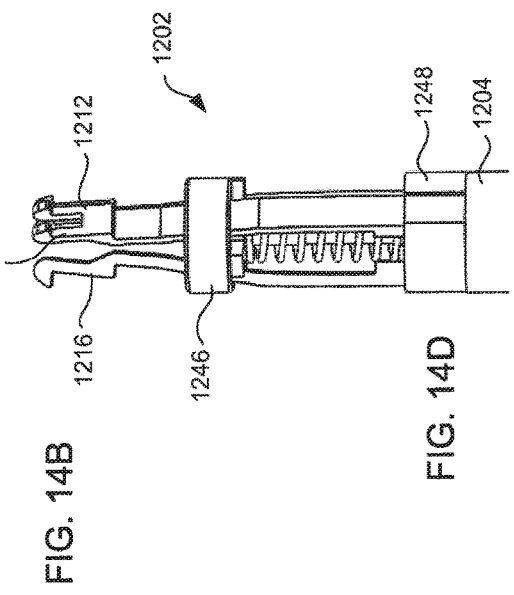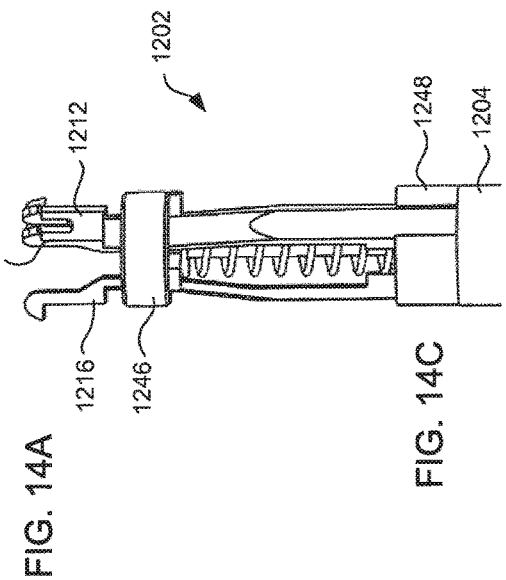

APPARATUS AND METHODS FOR DELIVERING DEVICES FOR REDUCING LEFT ATRIAL PRESSURE

I. CROSS-REFERENCE TO RELATED APPLICATIONS

This application is a continuation patent application of U.S. patent application Ser. No. 14/282,615, filed May 20, 2014, now U.S. Pat. No. 9,713,696, which claims the benefit of priority to U.S. Provisional Application Ser. No. 61/825,931, filed May 21, 2013, the contents of each of which are incorporated herein by reference in their entirety.

II. FIELD OF THE INVENTION

This application generally relates to devices and methods for reducing left atrial pressure, particularly in subjects with heart pathologies such as congestive heart failure (CHF) or myocardial infarction (MI), and apparatus for delivering such devices.

III. BACKGROUND OF THE INVENTION

Heart failure is the physiological state in which cardiac output is insufficient to meet the needs of the body and the lungs. CHF occurs when cardiac output is relatively low and the body becomes congested with fluid. There are many possible underlying causes of CHF, including myocardial infarction, coronary artery disease, valvular disease, and myocarditis. Chronic heart failure is associated with neurohormonal activation and alterations in autonomic control. Although these compensatory neurohormonal mechanisms provide valuable support for the heart under normal physiological circumstances, they also have a fundamental role in the development and subsequent progression of CHF. For example, one of the body's main compensatory mechanisms for reduced blood flow in CHF is to increase the amount of salt and water retained by the kidneys. Retaining salt and water, instead of excreting it into the urine, increases the volume of blood in the bloodstream and helps to maintain blood pressure. However, the larger volume of blood also stretches the heart muscle, enlarging the heart chambers, particularly the ventricles. At a certain amount of stretching, the heart's contractions become weakened, and the heart failure worsens. Another compensatory mechanism is vasoconstriction of the arterial system. This mechanism, like salt and water retention, raises the blood pressure to help maintain adequate perfusion.

In low ejection fraction (EF) heart failure, high pressures in the heart result from the body's attempt to maintain the high pressures needed for adequate peripheral perfusion. However, the heart weakens as a result of the high pressures, aggravating the disorder. Pressure in the left atrium may exceed 25 mmHg, at which stage, fluids from the blood flowing through the pulmonary circulatory system flow out of the interstitial spaces and into the alveoli, causing pulmonary edema and lung congestion.

Table 1 lists typical ranges of right atrial pressure (RAP), right ventricular pressure (RVP), left atrial pressure (LAP), left ventricular pressure (LVP), cardiac output (CO), and stroke volume (SV) for a normal heart and for a heart suffering from CHF. In a normal heart beating at around 70 beats/minute, the stroke volume needed to maintain normal cardiac output is about 60 to 100 milliliters. When the preload, after-load, and contractility of the heart are normal, the pressures required to achieve normal cardiac output are listed in Table 1. In a heart suffering from CHF, the hemodynamic parameters change (as shown in Table 1) to maximize peripheral perfusion.

TABLE 1

| Parameter | Normal Range | CHF Range |
| --- | --- | --- |
| RAP (mmHg) | 2-6 | 6-15 |
| RVP (mmHg) | 15-25 | 20-40 |
| LAP (mmHg) | 6-12 | 15-30 |
| LVP (mmHg) | 6-120 | 20-220 |
| CO (liters/minute) | 4-8 | 2-6 |
| SV (milliliters/beat) | 60-100 | 30-80 |

CHF is generally classified as either systolic heart failure (SHF) or diastolic heart failure (DHF). In SHF, the pumping action of the heart is reduced or weakened. A common clinical measurement is the ejection fraction, which is a function of the blood ejected out of the left ventricle (stroke volume), divided by the maximum volume remaining in the left ventricle at the end of diastole or relaxation phase. A normal ejection fraction is greater than 50%. Systolic heart failure has a decreased ejection fraction of less than 50%. A patient with SHF may usually have a larger left ventricle because of a phenomenon called cardiac remodeling that occurs secondarily to the higher ventricular pressures.

In DHF, the heart generally contracts normally, with a normal ejection fraction, but is stiffer, or less compliant, than a healthy heart would be when relaxing and filling with blood. This stiffness may impede blood from filling the heart, and produce backup into the lungs, which may result in pulmonary venous hypertension and lung edema. DHF is more common in patients older than 75 years, especially in women with high blood pressure.

Both variants of CHF have been treated using pharmacological approaches, which typically involve the use of vasodilators for reducing the workload of the heart by reducing systemic vascular resistance, as well as diuretics, which inhibit fluid accumulation and edema formation, and reduce cardiac filling pressure.

In more severe cases of CHF, assist devices such as mechanical pumps have been used to reduce the load on the heart by performing all or part of the pumping function normally done by the heart. Chronic left ventricular assist devices (LVAD), and cardiac transplantation, often are used as measures of last resort. However, such assist devices are typically intended to improve the pumping capacity of the heart, to increase cardiac output to levels compatible with normal life, and to sustain the patient until a donor heart for transplantation becomes available. Such mechanical devices enable propulsion of significant volumes of blood (liters/min), but are limited by a need for a power supply, relatively large pumps, and the risk of hemolysis, thrombus formation, and infection. Temporary assist devices, intra-aortic balloons, and pacing devices have also been used.

In addition to cardiac transplant, which is highly invasive and limited by the ability of donor hearts, surgical approaches such as dynamic cardiomyoplastic or the Batista partial left ventriculectomy may also be used in severe cases.

Various devices have been developed using stents or conduits to modify blood pressure and flow within a given vessel, or between chambers of the heart. For example, U.S. Pat. No. 6,120,534 to Ruiz is directed to an endoluminal stent for regulating the flow of fluids through a body vessel or organ, for example for regulating blood flow through the pulmonary artery to treat congenital heart defects. The stent may include an expandable mesh having lobed or conical portions joined by a constricted region, which limits flow through the stent. The mesh may comprise longitudinal struts connected by transverse sinusoidal or serpentine connecting members. Ruiz is silent on the treatment of CHF or the reduction of left atrial pressure.

U.S. Pat. No. 6,468,303 to Amplatz et al. discloses a collapsible medical device and associated method for shunting selected organs and vessels. Amplatz discloses that the device may be suitable to shunt a septal defect of a patient's heart, for example, by creating a shunt in the atrial septum of a neonate with hypoplastic left heart syndrome (HLHS). Amplatz discloses that increasing mixing of pulmonary and systemic venous blood improves oxygen saturation. Amplatz discloses that depending on the hemodynamics, the shunting passage can later be closed by an occluding device. Amplatz is silent on the treatment of CHF or the reduction of left atrial pressure, as well as on means for regulating the rate of blood flow through the device.

U.S. Patent Publication No. 2005/0165344 to Dobak, III discloses an apparatus for treating heart failure that includes a conduit positioned in a hole in the atrial septum of the heart, to allow flow from the left atrium into the right atrium. Dobak discloses that the shunting of blood will reduce left atrial pressures, thereby preventing pulmonary edema and progressive left ventricular dysfunction, and reducing LVEDP. Dobak discloses that the conduit may include a self-expandable tube with retention struts, such as metallic arms that exert a slight force on the atrial septum on both sides and pinch or clamp the valve to the septum, and a one-way valve member, such as a tilting disk, bileaflet design, or a flap valve formed of fixed animal pericardial tissue. However, Dobak states that a valved design may not be optimal due to a risk of blood stasis and thrombus formation on the valve, and that valves can also damage blood components due to turbulent flow effects. Dobak does not provide any specific guidance on how to avoid such problems.

In view of the foregoing, it would be desirable to provide devices for reducing left atrial pressure, and apparatus for delivering such devices to the atrial septum of the heart.

IV. SUMMARY OF THE INVENTION

The present invention overcomes the drawbacks of previously-known devices by providing apparatus for delivering a device for regulating blood pressure between a patient's left atrium and right atrium. The apparatus may include one or more latching legs, a release ring, a pull chord, a spring, and a catheter. The one or more latching legs may have a hook portion and may be configured to move from a first position, where the one or more latching legs extend radially outward, to a second position, where the one or more latching legs move radially inward to release the device. The pull chord may be configured to move the one or more latching legs from the first position to the second position. The catheter has a lumen and a center axis and the one or more latching legs and the pull chord may be at least partially disposed within the lumen. The hook portion of at least one of the one or more latching legs may hook outwardly away from the center axis to permit the latching legs to engage the device at the inner surface of the device.

At least one of the latching legs may include a ramp portion disposed proximal to the hook portion. The release ring may be coupled to the one or more latching legs and configured to contact an inner section of the ramp portion in the first position and to contact an outer section of the ramp portion in the second position. The pull chord may be coupled to the release ring such that actuation of the pull chord moves the release ring from the first position, where the one or more latching legs extend radially outward, to the second position, where the one or more latching legs move radially inward to release the device.

The apparatus may include a sheath and the catheter may be configured to be at least partially disposed within the sheath. The device may be configured to be disposed within the sheath in a contracted, delivery state. The one or more latching legs may be configured to move the device longitudinally forward and longitudinally backward through the sheath. Preferably, the apparatus is configured to deliver the device to an atrial septum of the patient.

In addition, the apparatus may include a handle coupled to the pull chord and disposed at a proximal end of the catheter, wherein the pull chord is actuated via the handle. A release ring base may be coupled to the release ring and the pull chord and the pull chord may move the release ring base to move the release ring from the first position the second position. A spring may be coupled to the release ring base, and the spring may be configured to bias the release ring towards the first position. In addition, the spring may be configured to limit travel of the release ring by reaching full compression. The apparatus also may include an annular member disposed proximal to release ring base and configured to maintain the spring between the release ring base and the annular member.

The one or more latching legs may include two latching legs that share a common ramp portion and a third latching leg having a separate ramp portion. The catheter may include a catheter end having an end lumen extending therethrough, and the one or more latching legs, the release ring, and the pull chord may be at least partially disposed within the end lumen.

In accordance with one aspect of the present invention, a method of delivering a device to a subject with heart pathology is provided. The method may include providing a delivery apparatus comprising one or more latching legs having a hook portion and a catheter having a lumen and a center axis, the one or more latching legs at least partially disposed within the lumen and the hook portion of the one or more latching legs configured to hook outwardly away from the center axis; coupling the hook portion to the device; positioning the device across a puncture through the fossa ovalis; and moving the one or more latching legs from a first position, where the one or more latching legs extend radially outward, to a second position, where the one or more latching legs move radially inward to decouple the hook portion from the device such that the device engages the atrial septum.

The method may include inserting the device in a sheath, partially retracting the sheath such that the device engages the left side of the atrial septum, and then fully retracting the sheath such that the device is partially disposed in the right atrium. The device may have first and second flared end regions and a neck region disposed therebetween, and optionally a tissue valve. The first flared end region may be disposed in, and engage, the atrial septum, and the second flared end region may be disposed in, and flank, the atrial septum.

The one or more latching legs may include a ramp portion disposed proximal to the hook portion and the delivery apparatus further comprises a release ring coupled to the one or more latching legs. In such an embodiment, moving the one or more latching legs further includes moving the release ring, via a pull chord, from the first position, where the release ring contacts an inner section of the ramp portion, to the second position, where the release ring contacts an outer section of the ramp portion.

Positioning the device may include positioning the device across the puncture through the fossa ovalis such that the neck region is positioned in the puncture. The method may include identifying the middle of the fossa ovalis of the atrial septum by pressing a needle against the fossa ovalis to partially tent the fossa ovalis, and puncturing the middle of the fossa ovalis with the needle. The puncture may be through the middle of the fossa ovalis and the device may be deployed away from the limbus, atrial wall, and the ridge between the inferior vena cava and coronary sinus.

In accordance with another aspect of the present invention, a method of delivering a device to a subject with heart pathology is provided. The method may include providing a delivery apparatus comprising one or more latching legs having a hook portion and a catheter having a lumen and a center axis, the one or more latching legs at least partially disposed within the lumen; coupling the hook portion to the device; positioning the device across a puncture through the fossa ovalis at a non-perpendicular angle between the center axis of the catheter and an outer wall of the atrial septum; and moving the one or more latching legs from a first position, where the one or more latching legs extend radially outward, to a second position, where the one or more latching legs move radially inward to decouple the hook portion from the device such that the device engages the atrial septum.

Embodiments of the present invention also provide hourglass-shaped devices for reducing left atrial pressure, and methods of making and using the same. As elaborated further herein, such reductions in left atrial pressure may increase cardiac output, relieve pulmonary congestion, and lower pulmonary artery pressure, among other benefits. The inventive devices are configured for implantation through the atrial septum, and particularly through the middle of the fossa ovalis, away from the surrounding limbus, inferior vena cava (IVC), and atrial wall. The devices are configured to provide one-way blood flow from the left atrium to the right atrium when the pressure in the left atrium exceeds the pressure in the right atrium, and thus decompress the left atrium. Such a lowering of left atrial pressure may offset abnormal hemodynamics associated with CHF, for example, to reduce congestion as well as the occurrence of acute cardiogenic pulmonary edema (ACPE), which is a severe manifestation of CHF in which fluid leaks from pulmonary capillaries into the interstitium and alveoli of the lung. In particular, lowering the left atrial pressure may improve the cardiac function by:

(1) Decreasing the overall pulmonary circulation pressure, thus decreasing the afterload on the heart, (2) Increasing cardiac output by reducing left ventricular end systolic dimensions, and (3) Reducing the left ventricular end-diastolic pressure (LVEDP) and pulmonary artery pressure (PAP), which in turn may enable the heart to work more efficiently and over time increase cardiac output. For example, the oxygen uptake of the myocardium may be reduced, creating a more efficient working point for the myocardium.

As described in further detail below, the devices provided herein comprise an hourglass or "diabolo" shaped stent encapsulated with a biocompatible material, and optionally secured (e.g., sutured) to a tissue valve. The stent, which may be formed of shape memory material, for example a shape memory metal such as NiTi, comprises a neck region disposed between two flared end regions. The tissue valve is coupled to a flared end region configured for implantation in the right atrium. Specifically, the device may be implanted by forming a puncture through the atrial septum, particularly through the fossa ovalis, and then percutaneously inserting the device therethrough such that the neck lodges in the puncture, the flared end to which the tissue valve is coupled engages the right side of the atrial septum, and the other flared end flanks the left side of the atrial septum (e.g., is spaced apart from and does not contact the left side of the atrial septum). Placement in the middle of the fossa ovalis is useful because the engagement of the right-side flared end with the atrial septum enhances the stability of the valve. The neck region and the flared end region for placement in the left atrium may each be covered with a biocompatible polymer, such as expanded polytetrafluoroethylene (ePTFE), polyurethane, DACRON (polyethylene terephthalate), silicone, polycarbonate urethane, or pericardial tissue from an equine, bovine, or porcine source, which is optionally treated so as to promote a limited amount of tissue ingrowth, e.g., of epithelial tissue or a neointima layer. The tissue valve is connected to the biocompatible polymer in the right-side flared end region, close to the neck region, and is preferably a tricuspid, bicuspid, or duckbill valve configured to allow blood to flow from the left atrium to the right atrium when the pressure in the left atrium exceeds that in the right atrium, but prevent flow from the right atrium to the left atrium. In preferred embodiments, the device is effective to maintain the pressure differential between the left atrium and right atrium to 15 mmHg or less.

Under one aspect of the present invention, a device for regulating blood pressure between a patient's left atrium and right atrium comprises an hourglass-shaped stent comprising a neck and first and second flared end regions, the neck disposed between the first and second end regions and configured to engage the fossa ovalis of the patient's atrial septum; and optionally a one-way tissue valve coupled to the first flared end region and configured to shunt blood from the left atrium to the right atrium when blood pressure in the left atrium exceeds blood pressure in the right atrium. In accordance with one aspect of the invention, moving portions of the valve are disposed in the right atrium, joined to but spaced apart from the neck region.

The hourglass-shaped stent may include a shape memory material (e.g., metal) coated with a biocompatible polymer from a portion of the first flared end region, through the neck region, and through the second flared end region, and the tissue valve may extend between the first flared end region and the biocompatible polymer. Providing the tissue valve in the side of the device to be implanted in the right atrium (that is, in the first flared end region) may inhibit thrombus formation and tissue ingrowth by providing that the tissue valve, as well as the region where the tissue valve is secured (e.g., sutured) to the biocompatible polymer, is continuously flushed with blood flowing through the right atrium. By comparison, if the tissue valve was instead secured (e.g., sutured) to the biocompatible polymer in the neck region, then the interface between the two would contact the tissue of the fossa ovalis, which potentially would encourage excessive tissue ingrowth, create leakages, and cause inflammation. Moreover, tissue ingrowth into the neck region would cause a step in the flow of blood in the narrowest part of the device, where flow is fastest, which would increase shear stresses and cause coagulation. Instead providing the tissue valve entirely within the right atrial side of the device inhibits contact between the tissue valve and the tissue of the atrial septum and fossa ovalis. Further, any tissue that ingrows into the valve will not substantially affect blood flow through the device, because the valve is located in a portion of the device having a significantly larger diameter than the neck region. Moreover, if the biocompatible tissue were instead to continue on the portions of the frame positioned over the tissue valve, it may create locations of blood stasis between the leaflets of the tissue valve and the biocompatible material. Having the valve entirely on the right atrial side and without biocompatible material on the overlying frame enables continuous flushing of the external sides of the tissue valve with blood circulating in the right atrium.

The biocompatible material preferably promotes limited (or inhibits excessive) tissue ingrowth into the valve, the tissue ingrowth including an endothelial layer or neointima layer inhibiting thrombogenicity of the device. The endothelial or neointima layer may grow to a thickness of 0.2 mm or less, so as to render the material inert and inhibit hyperplasia.

The hourglass-shaped stent may include a plurality of sinusoidal rings interconnected by longitudinally extending struts. In some embodiments, when the shunt is deployed across the patient's atrial septum, the first flared end region protrudes 5.5 to 7.5 mm into the right atrium. The second flared end region may protrude 2.5 to 7 mm into the left atrium. The neck may have a diameter of 4.5 to 5.5 mm. The first flared end region may have a diameter between 9 and 13 mm, and the second flared end region may have a diameter between 8 and 15 mm. The first and second flared end regions each may flare by about 50 to 120 degrees. For example, in one embodiment, the first flared end region flares by about 80 degrees, that is, the steepest part of the outer surface of the first flared end region is at an angle of approximately 40 degrees relative to a central longitudinal axis of the device. The second flared end region may flare by about 30-70 degrees, where the steepest part of the outer surface of the second flared end region may be at an angle of approximately 35 degrees relative to the central longitudinal axis of the device. The second flare may be have a tapered shape starting with a wider angle in the range of about 50-70 degrees and ending with a narrow angle in the range of about 30-40 degrees.

The inlet of the tissue valve may be about 1-3 mm from a narrowest portion of the neck region, and the outlet of the tissue valve may be about 5-8 mm from the narrowest portion of the neck region. The tissue valve may comprise a sheet of tissue having a flattened length of about 10-16 mm, and the sheet of tissue may be folded and sutured so as to define two or more leaflets each having a length of about 5-8 mm. For example, the tissue sheet may have a flattened length of no greater than 18 mm, for example, a length of 10-16 mm, or 12-14 mm, or 14-18 mm, and may be folded and sutured to define two or more leaflets each having a length of, for example, 9 mm or less, or 8 mm or less, or 7 mm or less, or 6 mm or less, or even 5 mm or less, e.g., 5-8 mm. The tissue sheet may have a flattened height no greater than 10 mm, for example, a height of 2-10 mm, or 4-10 mm, or 4-8 mm, or 6-8 mm, or 4-6 mm. The tissue sheet may have a flattened area of no greater than 150 square mm, for example, 60-150 square mm, or 80-120 square mm, or 100-140 square mm, or 60-100 square mm.

The hourglass-shaped stent may be configured to transition between a collapsed state suitable for percutaneous delivery and an expanded state when deployed across the patient's fossa ovalis. The stent may have an hourglass configuration in the expanded state. The hourglass configuration may be asymmetric. The stent may be configured for implantation through the middle of the fossa ovalis, away from the surrounding limbus, inferior vena cava, and atrial wall. The hourglass-shaped stent may be designed in such way that when collapsed into a sheath, the neck of the stent maintains a diameter smaller than the sheath inner diameter. The sheath may have a tapered tip with locally reduced diameter at its tip. The neck of the stent is configured to self-position itself within the sheath tip when the stent is partially deployed. Additionally, when the stent is partially deployed, a relatively high force is required to further advance the stent into the left atrium. Such additional force provides confirmation to the clinician that the stent is partially deployed, reduces the chance of total deployment in the left atrium, and reduces the risk that emboli will travel into the left atrium during full deployment.

The one-way tissue valve may have two or more leaflets, e.g., may have a tricuspid or bicuspid design. The one-way tissue valve may comprise pericardial tissue, which in one embodiment may consist primarily of the mesothelial and loose connective tissue layers, and substantially no dense fibrous layer. Note that the dimensions of the hourglass-shaped device may be significantly smaller than those of replacement aortic valves, which may for example have a diameter of 23 mm and require the use of larger, thicker valve leaflets to maintain the higher stresses generated by the combination of higher pressures and larger diameters. By comparison, the inventive device has much smaller dimensions, allowing the use of thinner tissue (e.g., about one third the thickness of tissue used in a replacement aortic valve), for example, pericardial tissue in which the external dense fibrous layer is delaminated and the mesothelial and loose connective tissue is retained.

Under another aspect of the present invention, a device for regulating blood pressure between a patient's left atrium and right atrium includes a stent comprising a neck region and first and second flared end regions, the neck region disposed between the first and second end regions and configured to engage the fossa ovalis of the patient's atrial septum; a biocompatible material disposed on the stent in the neck and the second flared end region and a portion of the first flared end region; and optionally a one-way tissue valve configured to shunt blood from the left atrium to the right atrium when blood pressure in the left atrium exceeds blood pressure in the right atrium, the valve having an outlet coupled to the first flared end region and an inlet coupled to an edge of the biocompatible material, the valve and the biocompatible material defining a continuous sheath that inhibits excessive tissue ingrowth into the valve and channels blood flow through the valve. In one embodiment, the edge of the biocompatible material is about 1-3 mm, e.g., 2 mm, from a narrowest portion of the neck region.

Under another aspect, a method of treating a subject with heart pathology comprises: providing a device having first and second flared end regions and a neck region disposed therebetween, and a tissue valve coupled to the first flared end region; deploying the device across a puncture through the subject's fossa ovalis such that the neck region is positioned in the puncture, the first flared end region is disposed in, and engages, the atrial septum, and the second flared end region is disposed in, and flanks, the atrial septum; and reducing left atrial pressure and left ventricular end diastolic pressure by shunting blood from the left atrium to the right atrium through the device when the left atrial pressure exceeds the right atrial pressure.

Subjects with a variety of heart pathologies may be treated with, and may benefit from, the inventive device. For example, subjects with myocardial infarction may be treated, for example by deploying the device during a period immediately following the myocardial infarction, e.g., within six months after the myocardial infarction, or within two weeks following the myocardial infarction. Other heart pathologies that may be treated include heart failure and pulmonary congestion. Reducing the left atrial pressure and left ventricular end diastolic pressure may provide a variety of benefits, including but not limited to increasing cardiac output; decreasing pulmonary congestion; decreasing pulmonary artery pressure; increasing ejection fraction; increasing fractional shortening; and decreasing left ventricle internal diameter in systole. Means may be provided for measuring such parameters.

Such methods may include identifying the middle of the fossa ovalis of the atrial septum by pressing a needle against the fossa ovalis to partially tent the fossa ovalis; and puncturing the middle of the fossa ovalis with the needle.

Under yet another aspect of the present invention, a method of making a device comprises: providing a tube of shape-memory metal; expanding the tube on a mandrel to define first and second flared end regions and a neck therebetween, and heating the expanded tube to set the shape; coating the neck and second flared end region with a biocompatible material; providing a valve of animal pericardial tissue having leaflets fixed in a normally closed position; and securing an inlet of the valve to the first flared end region and to the biocompatible polymer at the neck region. The tube may be laser cut and may include a plurality of sinusoidal rings connected by longitudinally extending struts, and the valve may be sutured to the struts and to the biocompatible material to form a passage for blood.

V. BRIEF DESCRIPTION OF THE DRAWINGS

FIGS. 1A-1D illustrate perspective views of an hourglass-shaped device having a tricuspid valve, according to some embodiments of the present invention.

FIG. 2A schematically illustrates a plan view of the right atrial side of the atrial septum, including a site for implanting an hourglass-shaped device through the middle of the fossa ovalis.

FIG. 2B schematically illustrates a cross-sectional view of the hourglass-shaped device of FIGS. 1A-1D positioned in the fossa ovalis of the atrial septum, according to some embodiments of the present invention.

Figure 4:
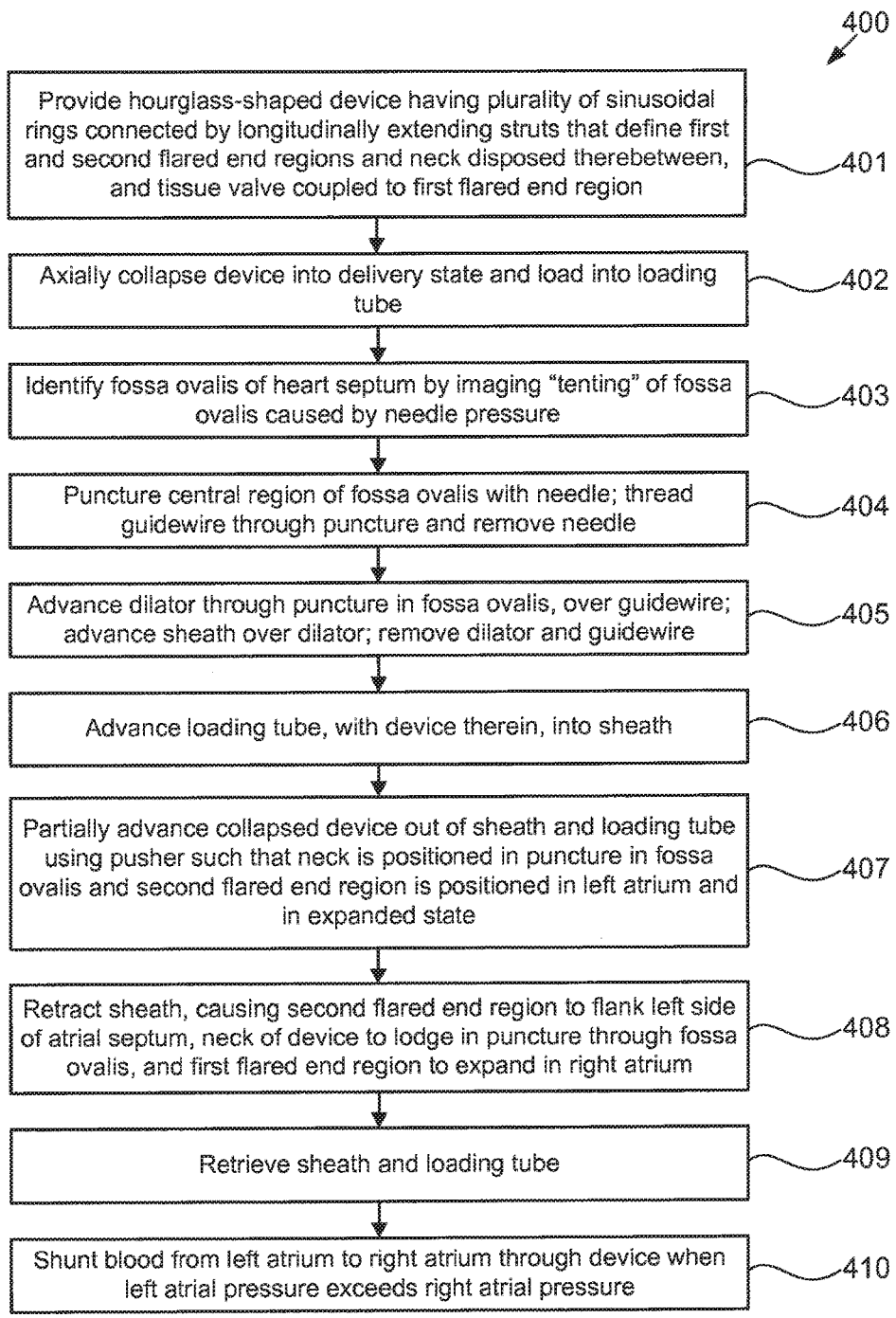
FIG. 4 is a flow chart of steps in a method of percutaneously implanting an hourglass-shaped device in a puncture through the fossa ovalis, according to some embodiments of the present invention.

FIGS. 5A-5D schematically illustrate steps taken during the method of FIG. 4, according to some embodiments of the present invention.

Figure 6A:
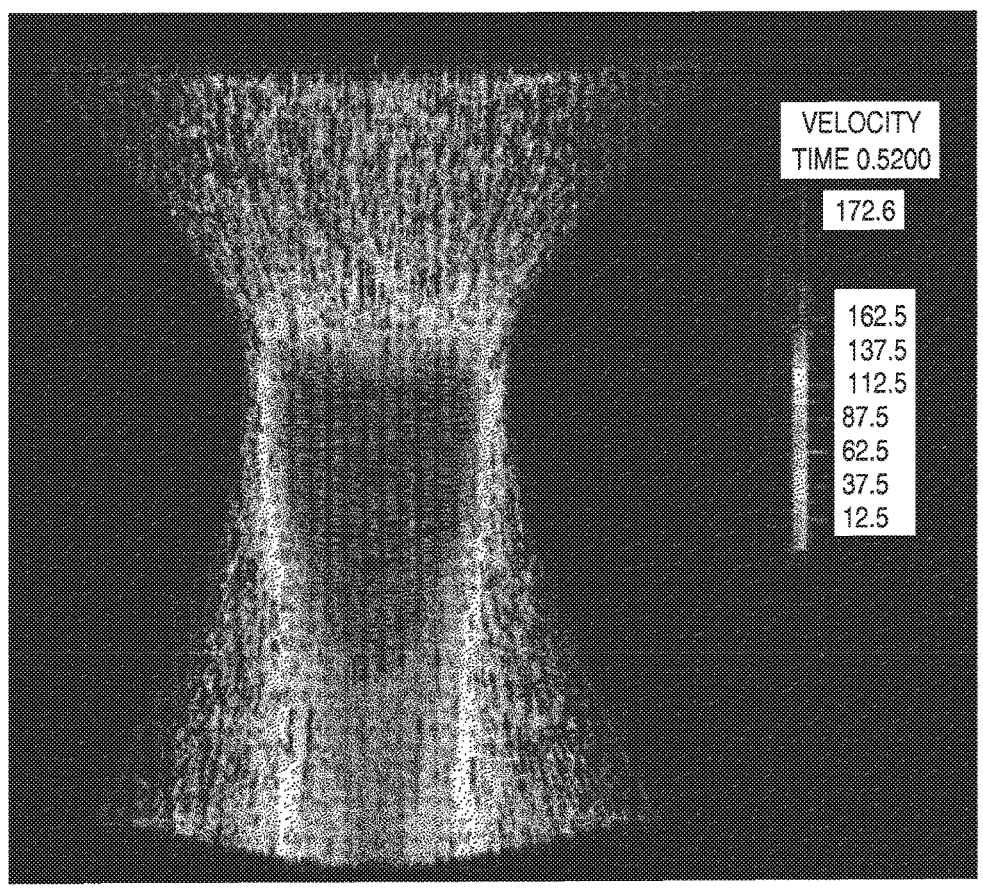

FIG. 6A is an image from a computational fluid dynamic model of flow through an hourglass-shaped device in the open configuration.

Figure 6B:
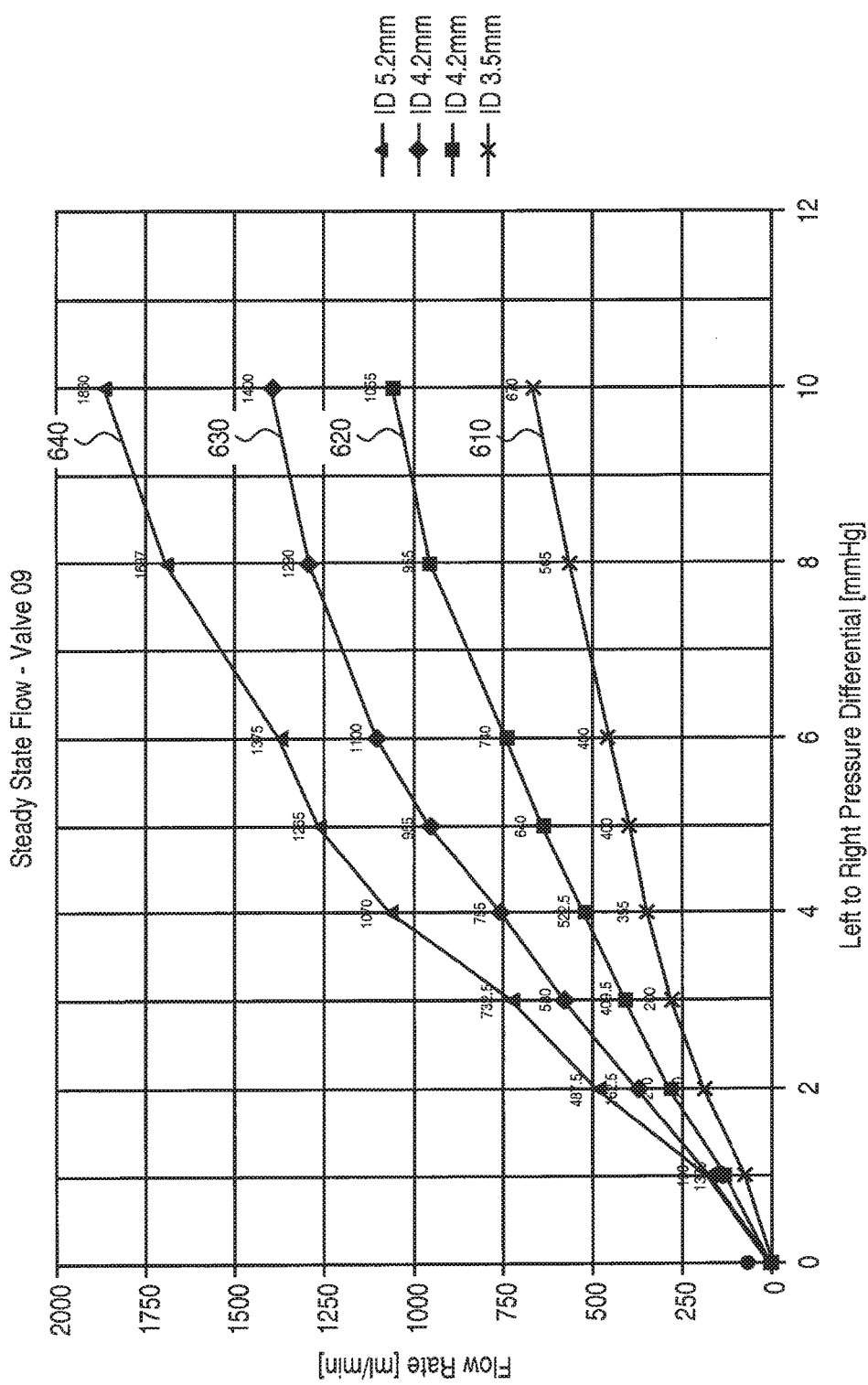

FIG. 6B is a plot showing the relationship between the left-to-right atrial pressure differential and the flow rate through the valve for hourglass-shaped devices having different valve diameters, according to some embodiments of the present invention.

Figure 7:
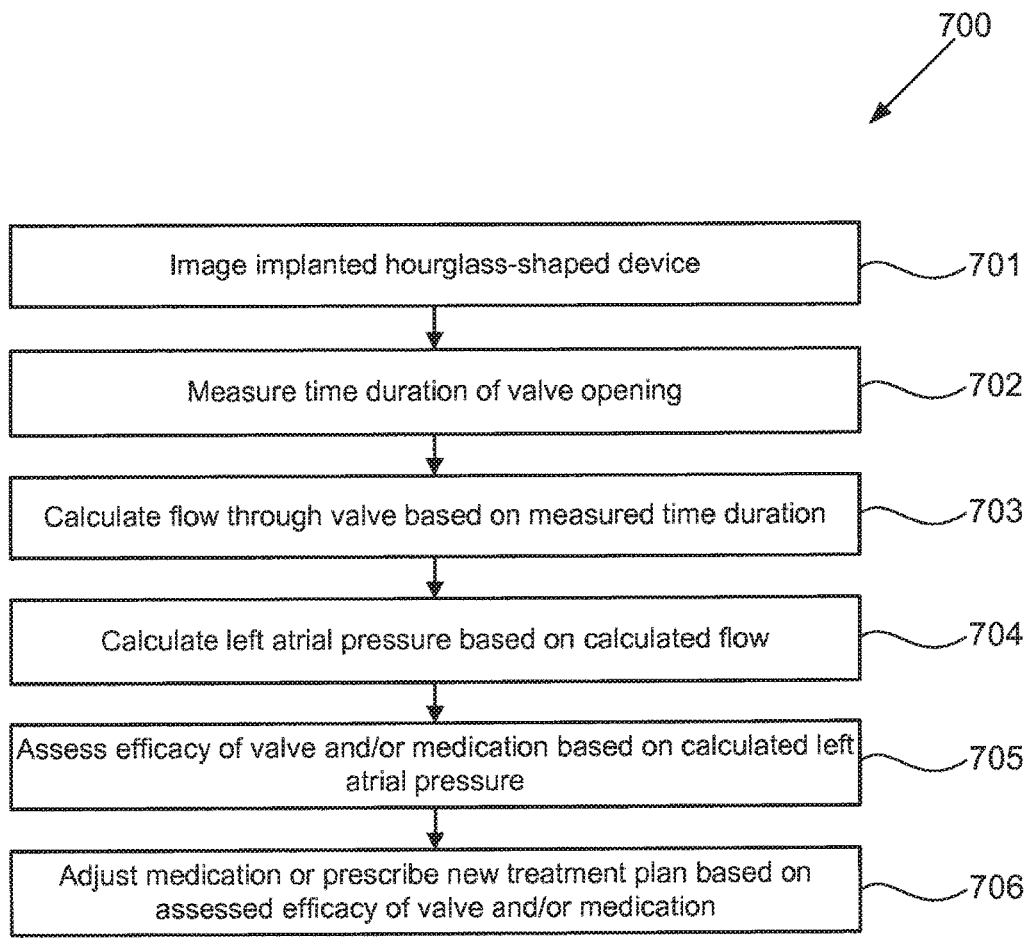

FIG. 7 is a flow chart of steps in a method of noninvasively determining left atrial pressure using an hourglass-shaped device, and adjusting a treatment plan based on same, according to some embodiments of the present invention.

Figure 8A:
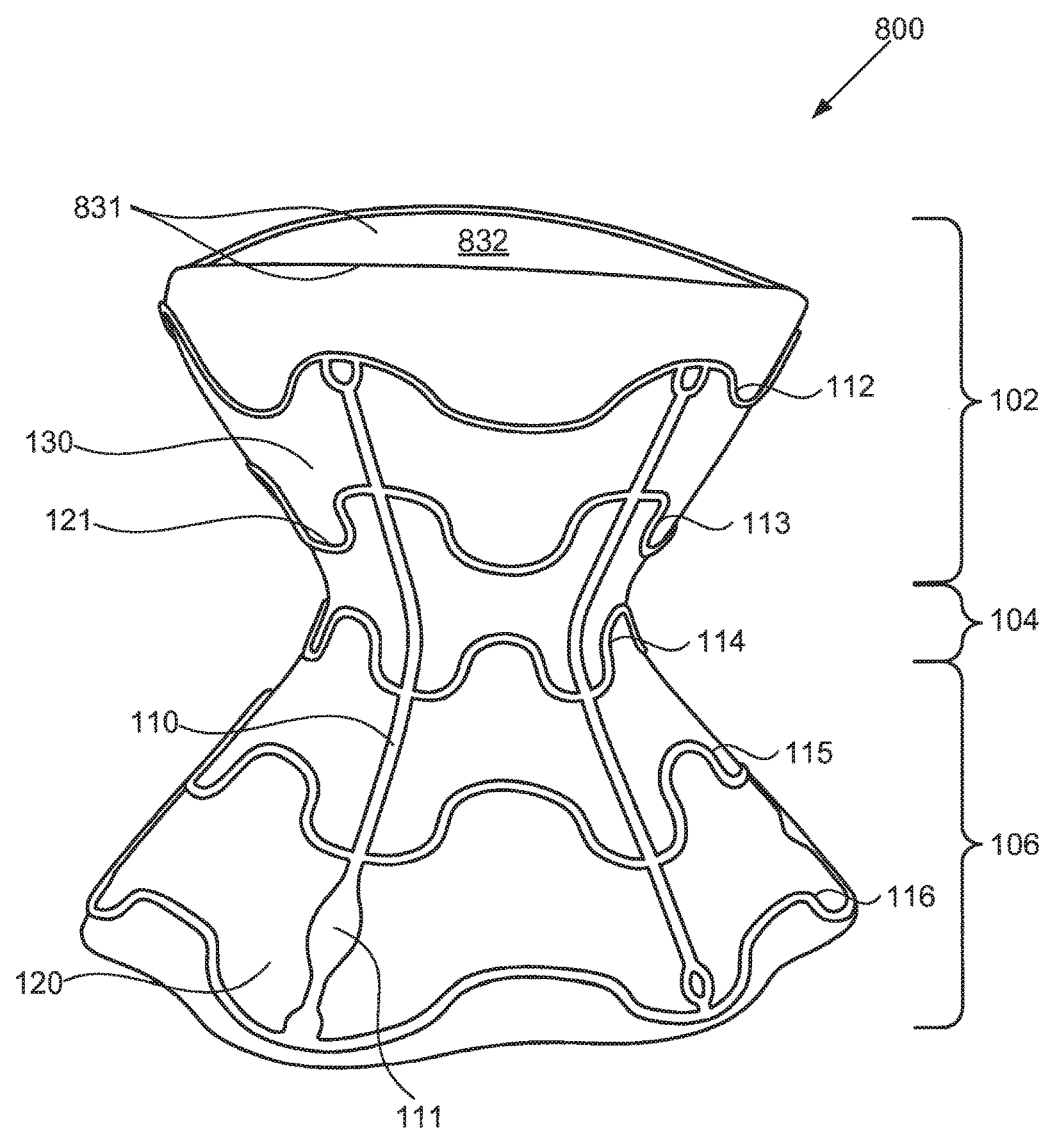
Figure 8B:
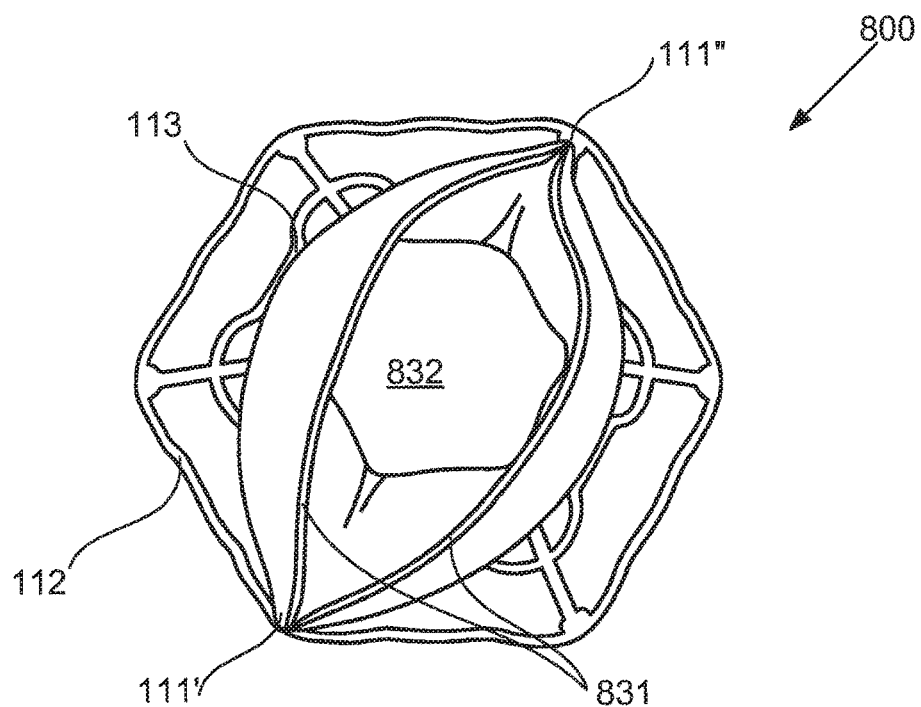
Figure 8C:
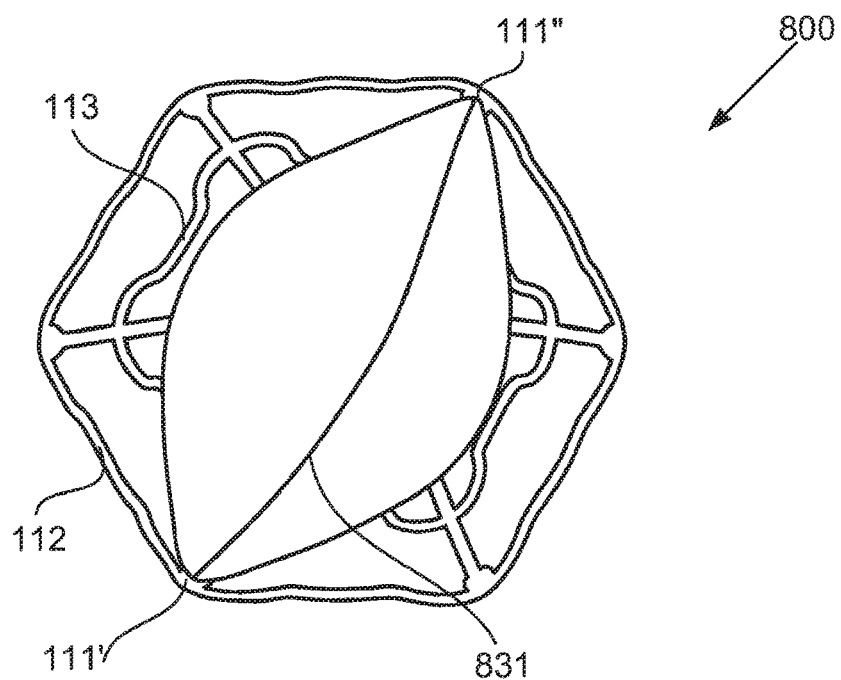

FIGS. 8A-8C illustrate perspective views of an alternative hourglass-shaped device, according to some embodiments of the present invention.

Figure 9:
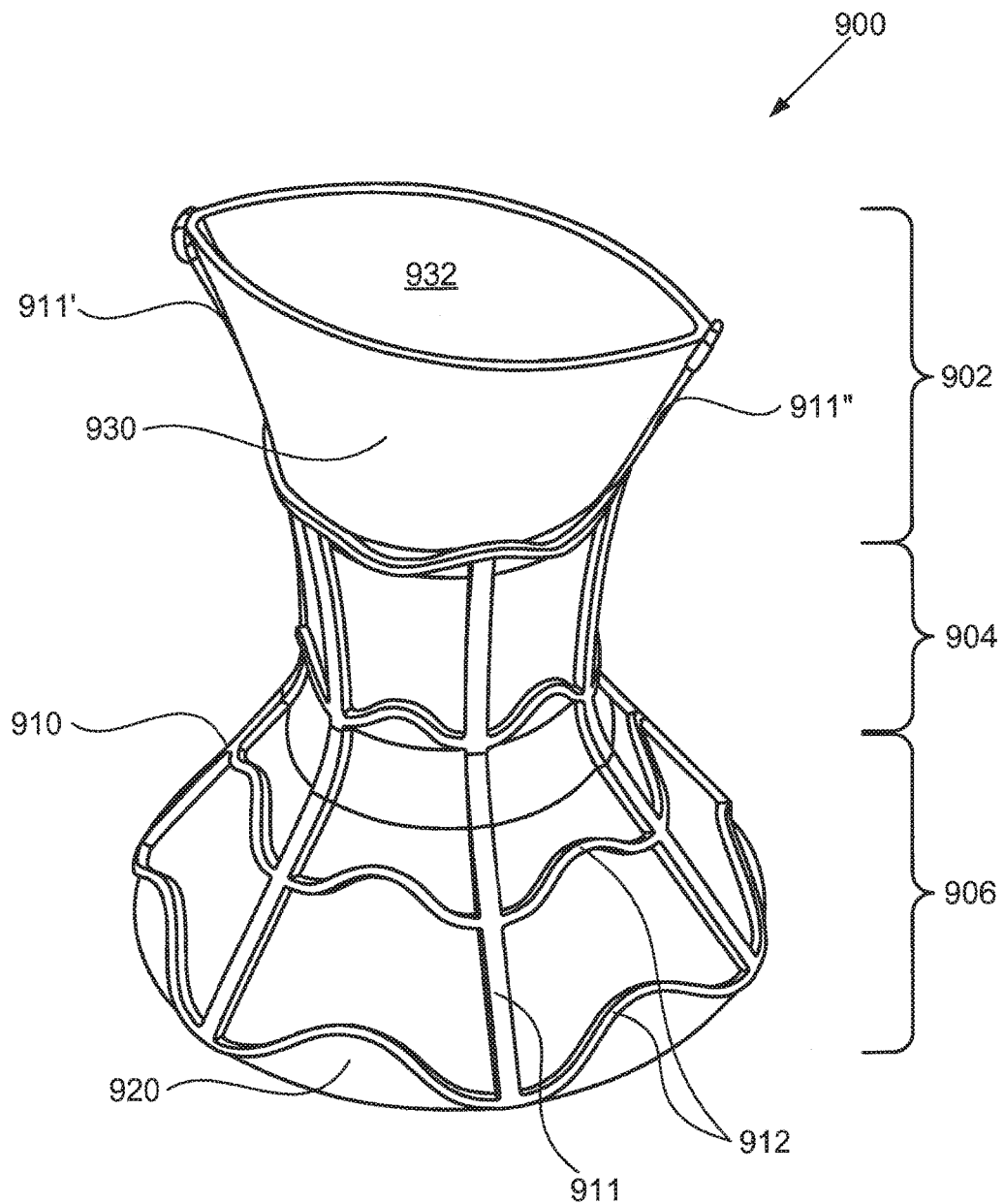

FIG. 9 is a perspective view of a further alternative hourglass-shaped device, according to some embodiments of the present invention.

FIGS. 10A-10D are plots respectively showing the left atrial pressure, right atrial pressure, ejection fraction, and pulmonary artery pressure in animals into which an exemplary hourglass-shaped device was implanted, as well as control animals, during a twelve-week study.

Figure 11A:
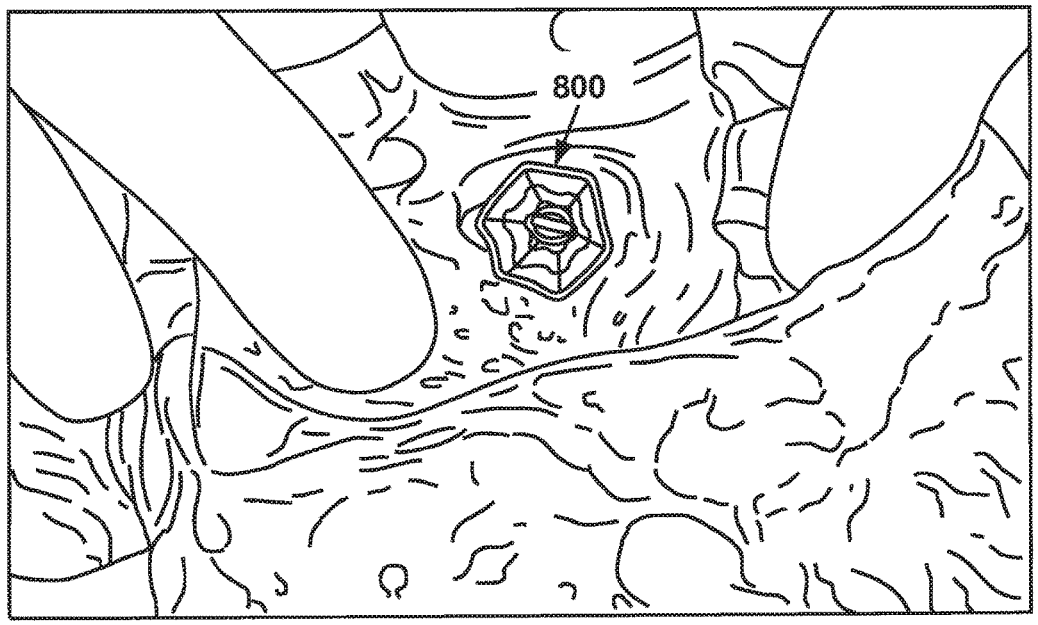
Figure 11B:

FIGS. 11A-11B are photographic images showing an hourglass-shaped device following explantation from an animal after being implanted for 12 weeks.

Figure 11C:
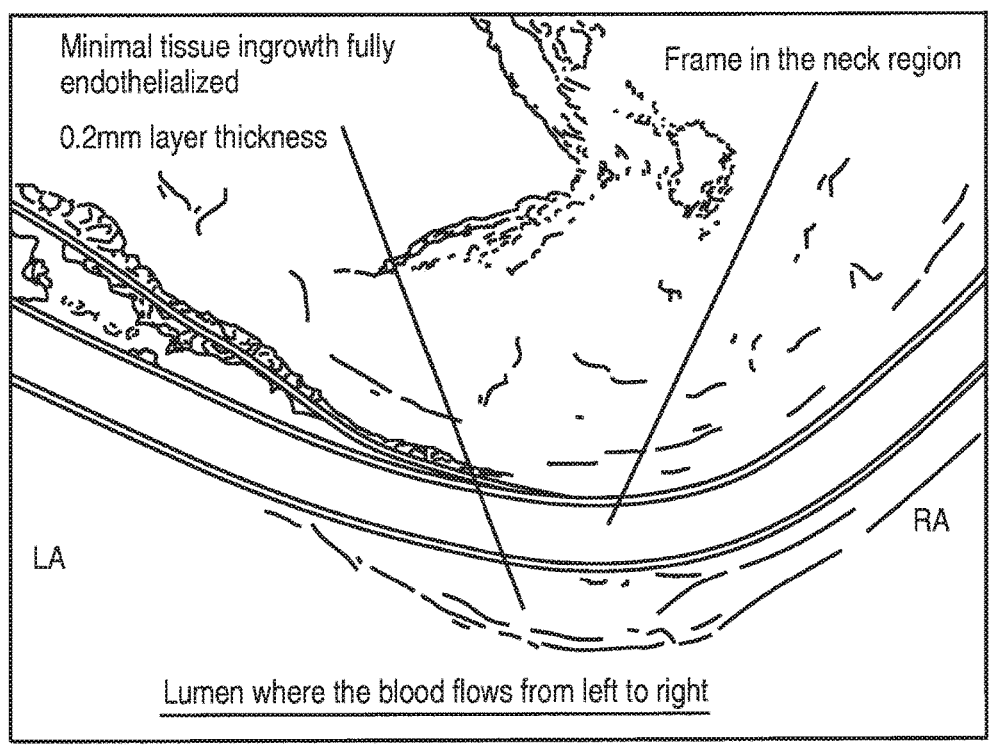

FIG. 11C is a microscope image of a cross-section of an hourglass-shaped device following explantation from an animal after being implanted for 12 weeks.

FIGS. 12A and 12B illustrate an exemplary apparatus for delivering devices in accordance with the present invention, wherein the exemplary apparatus is in the engaged position in FIG. 12A and the disengaged position in FIG. 12B.

FIGS. 13A and 13B, respectively, illustrate the distal end of the exemplary apparatus in the engaged position shown in FIG. 12A and the disengaged position shown in FIG. 12B.

FIGS. 14A to 14D illustrate the inner components at the distal end of the exemplary apparatus, wherein FIGS. 14A and 14C show the components in the engaged position and FIGS. 14B and 14D show the components in the disengaged position.

Figure 15B:
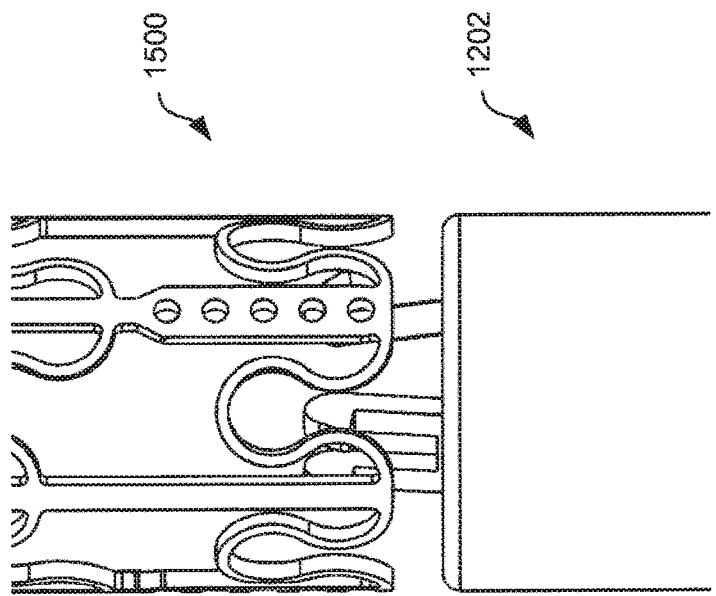
Figure 15A:
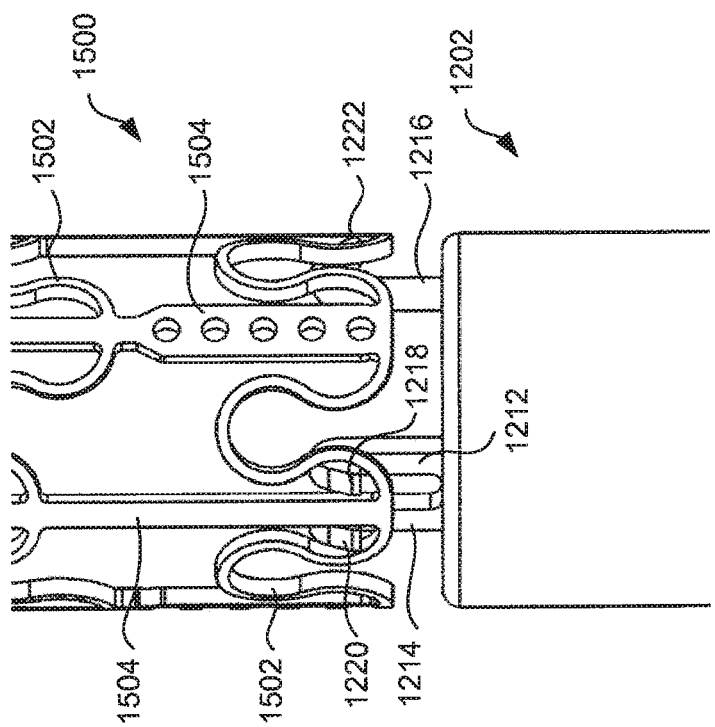

FIG. 15A illustrates the distal end of an exemplary delivery apparatus engaged to an exemplary device, partially shown, in accordance with the present invention and FIG. 15B illustrates the exemplary delivery apparatus disengaged from the exemplary device.

Figure 16:
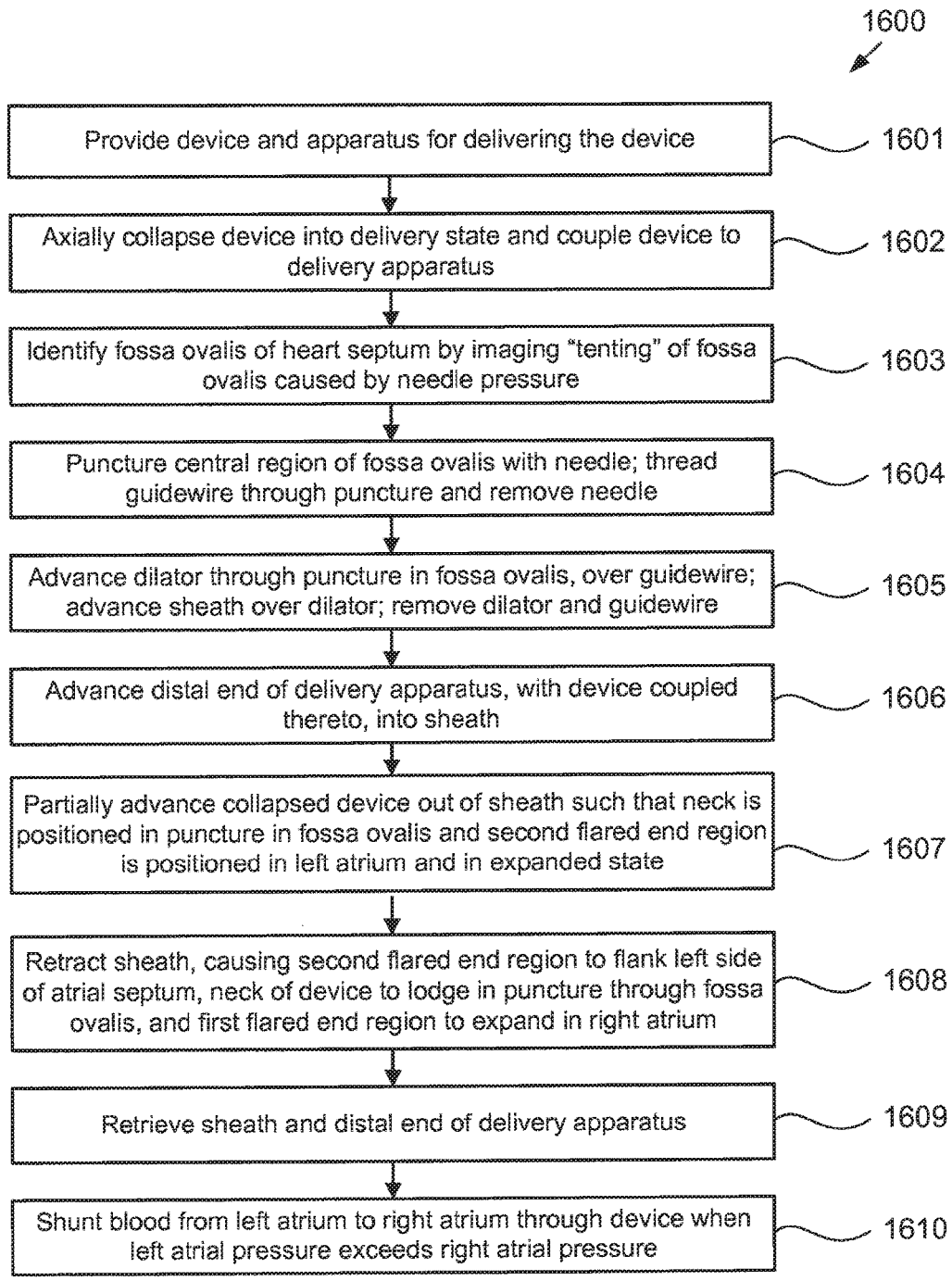

FIG. 16 is a flow chart of steps in a method of percutaneously implanting an hourglass-shaped device in a puncture through the fossa ovalis using exemplary delivery apparatus, according to some embodiments of the present invention.

Figure 17A:
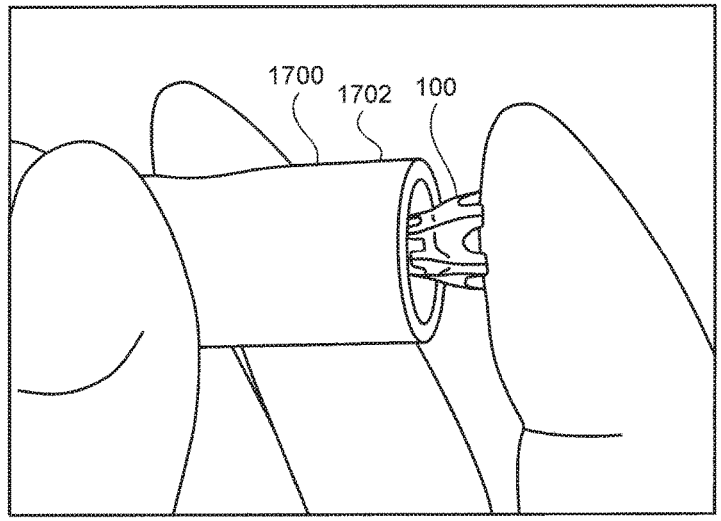
Figure 17B:
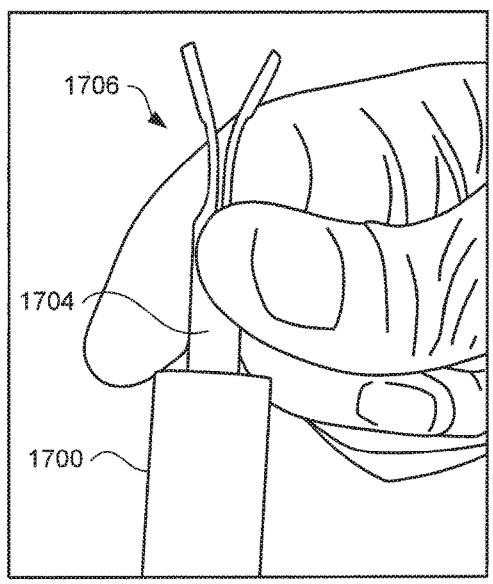
Figure 17C:
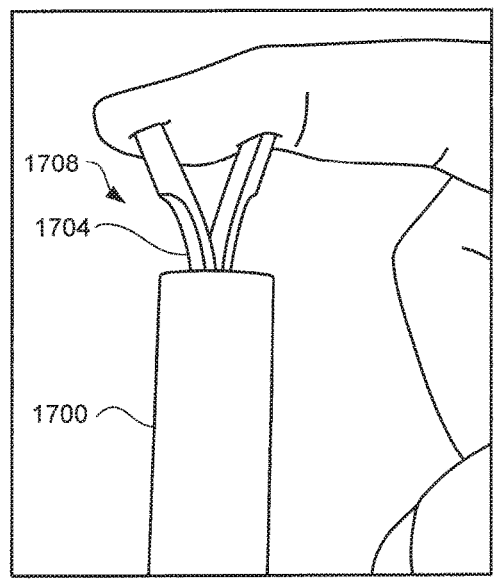
Figure 17D:
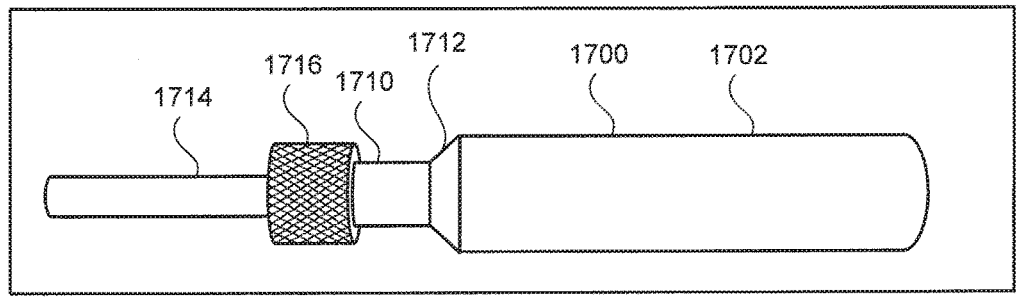
Figure 17E:
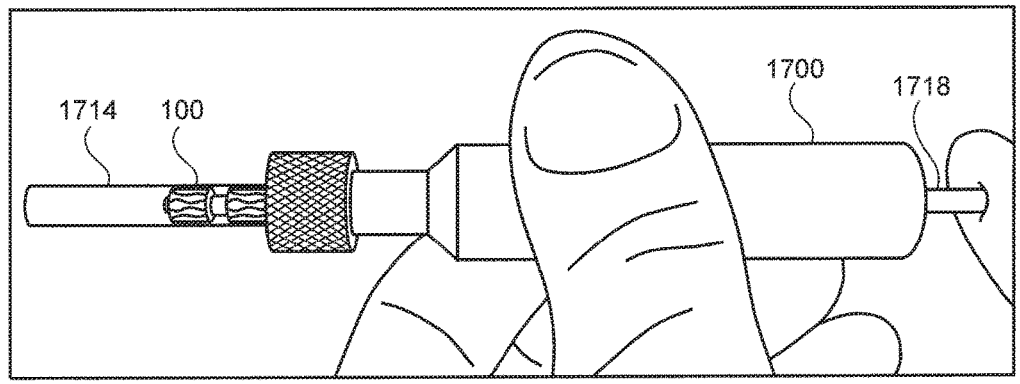
Figure 17F:
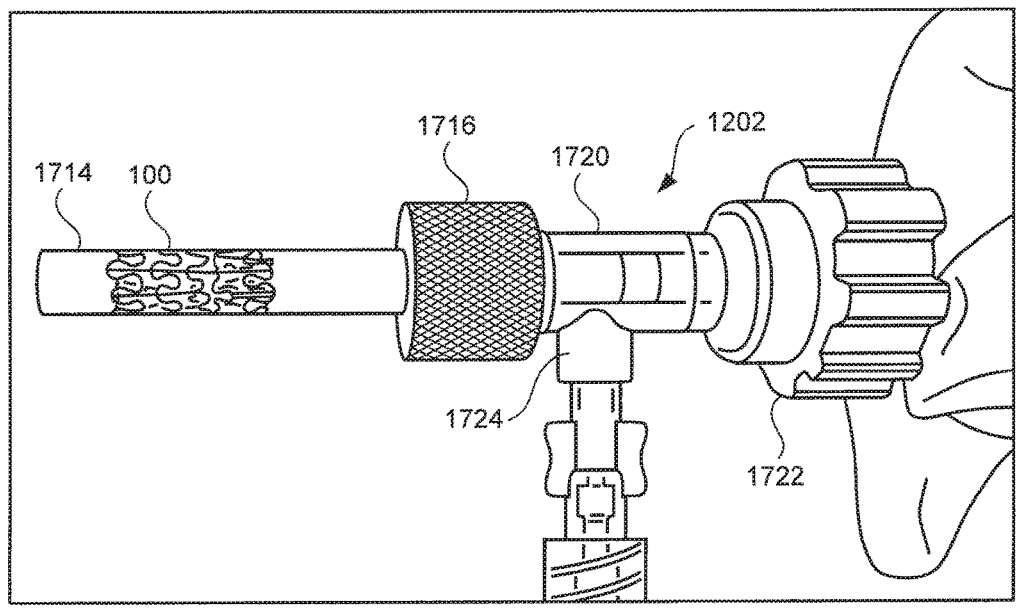
Figure 17G:
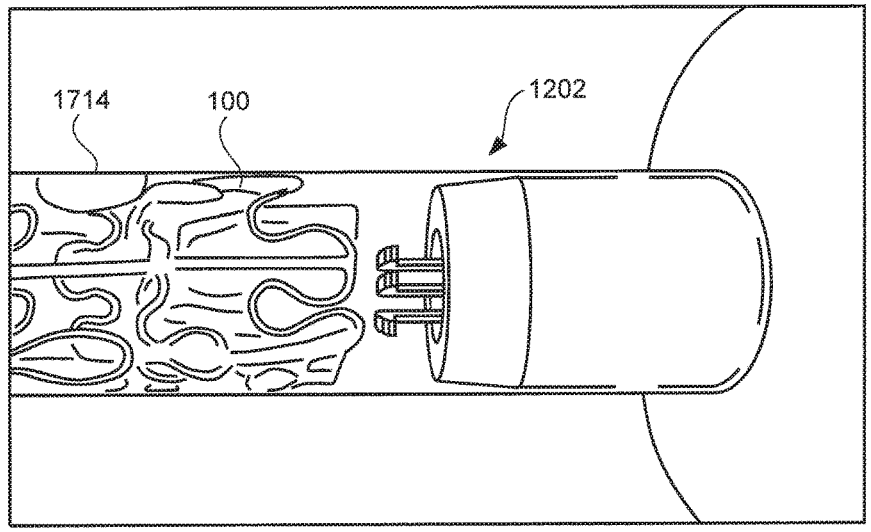
Figure 17H:
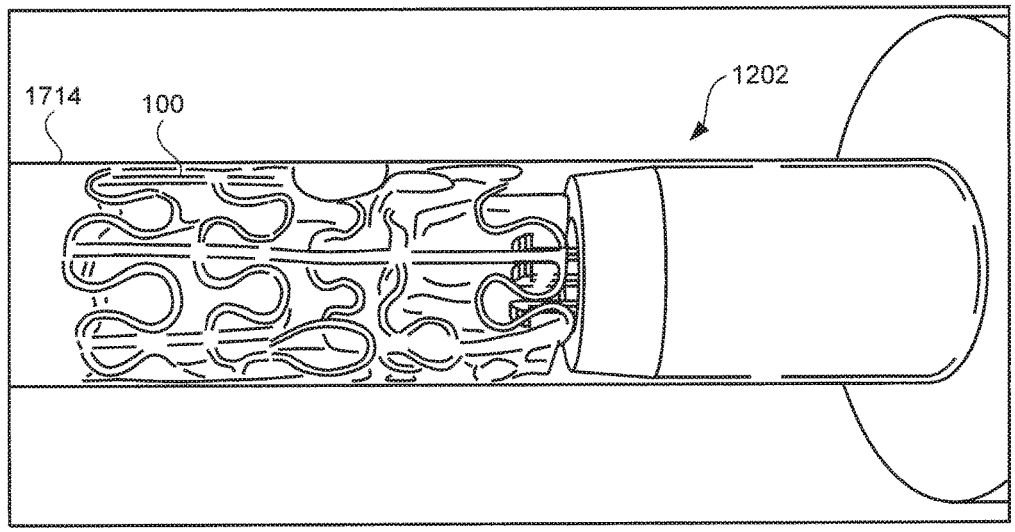
Figure 17I:
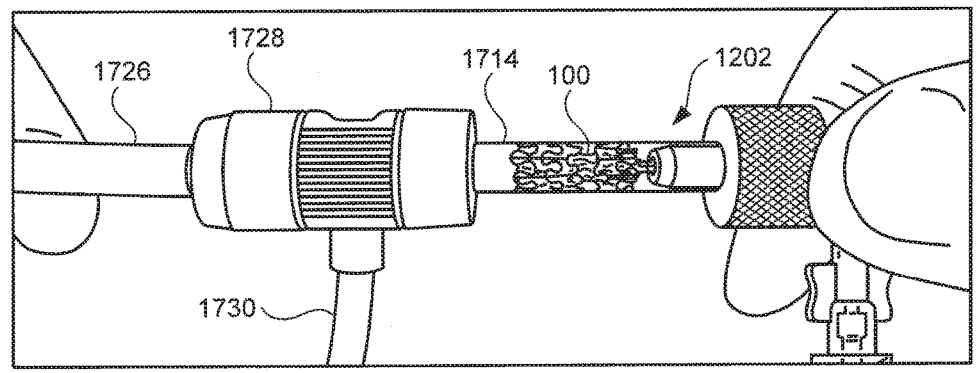
Figure 17J:
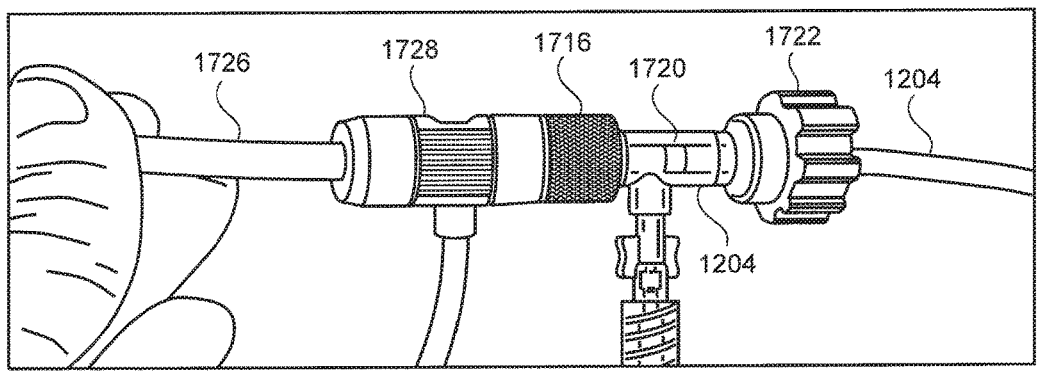
Figure 17K:
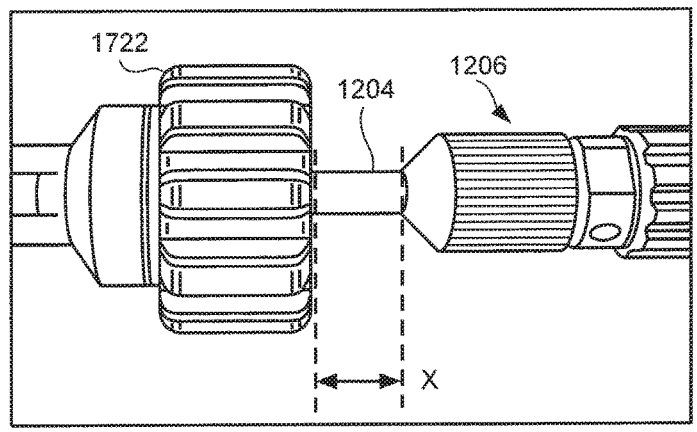
Figure 17L:
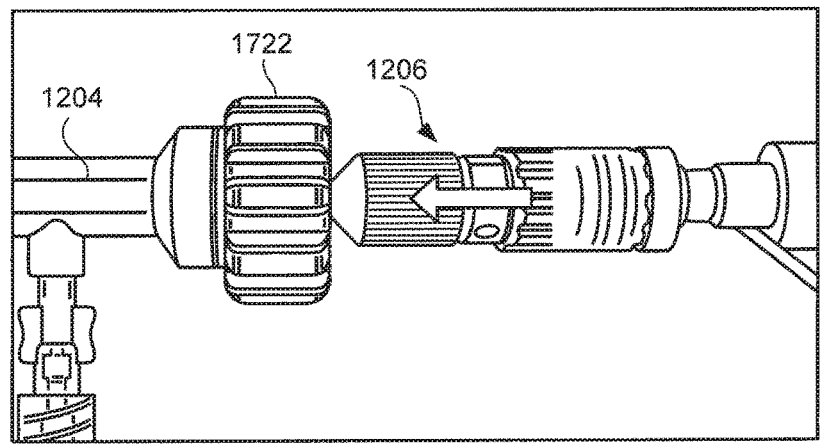
Figure 17M:
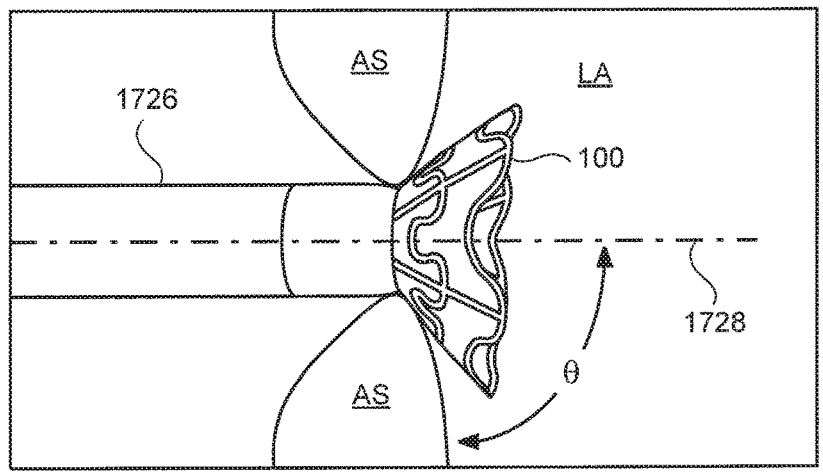
Figure 17N:
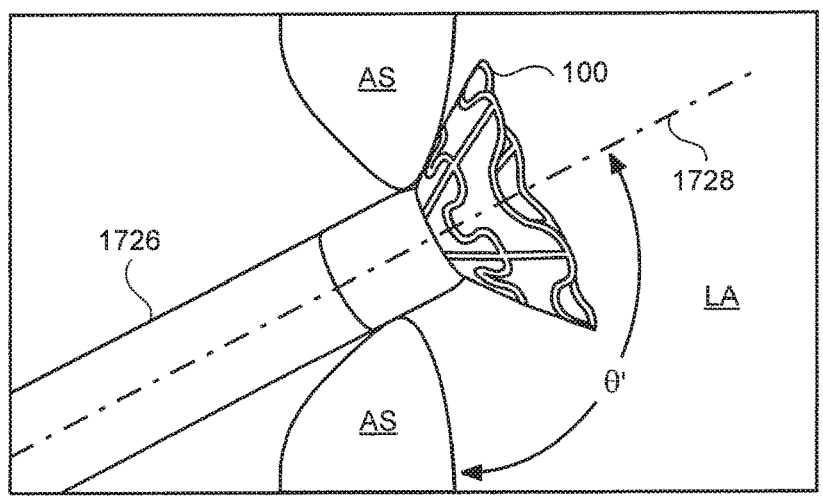
Figure 17O:
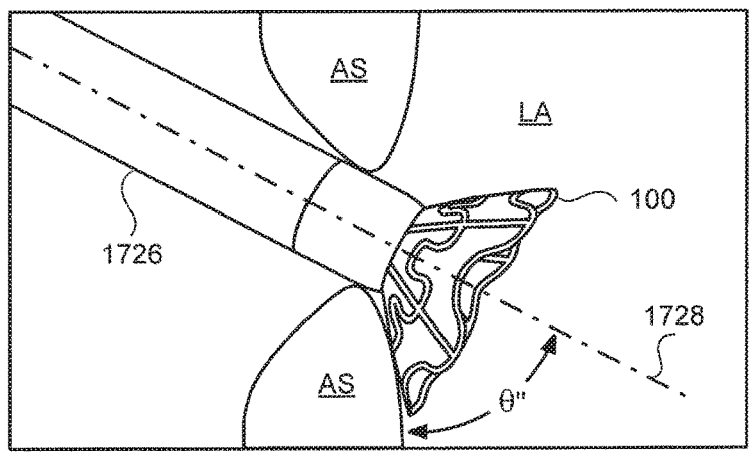
Figure 17P:
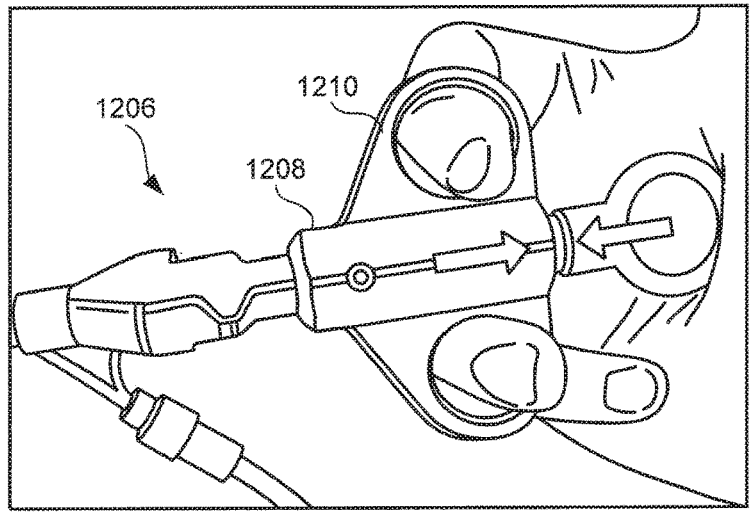
Figure 17Q:
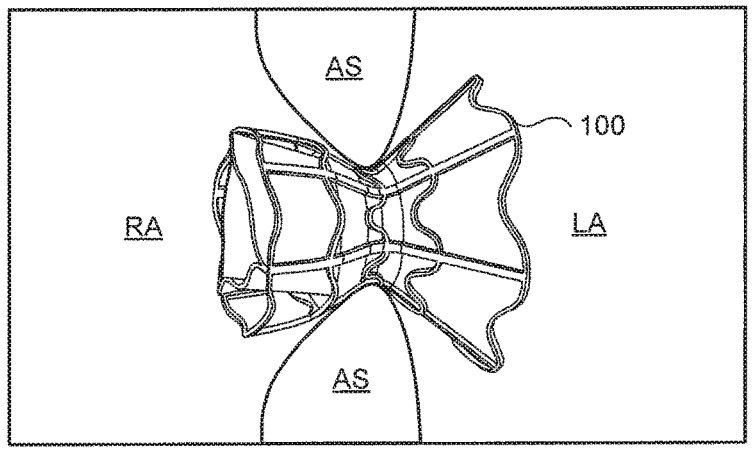

FIGS. 17A-17Q schematically illustrate steps taken during the method of FIG. 16, according to some embodiments of the present invention

VI. DETAILED DESCRIPTION OF THE INVENTION

Embodiments of the present invention are directed to devices that reduce left atrial pressure, and thus may be useful in treating subjects suffering from congestive heart failure (CHF) or other disorders associated with elevated left atrial pressure. Specifically, the inventive device includes an hourglass or "diabolo" shaped stent, preferably formed of a shape memory metal, and, optionally, a biocompatible valve coupled thereto. The stent is configured to lodge securely in the atrial septum, preferably the fossa ovalis, and to allow blood flow from the left atrium to the right atrium, preferably through the fossa ovalis, and the valve may be used to allow one-way blood flow when blood pressure in the left atrium exceeds that on the right. Usefully, the inventive devices are configured so as to reduce blood pressure in the left atrium even when the pressure differential therebetween is relatively low; to provide a smooth flow path with a large opening, thus inhibiting turbulence and high shear stresses that would otherwise promote thrombus formation; to seal securely with rapid valve closure when the left and right atrial pressures equalize or the right atrial pressure exceeds left atrial pressure; and to have a relatively small implantation footprint so as to inhibit tissue overgrowth and inflammatory response.

First, a preferred embodiment of the inventive hourglass-shaped device will be described, and then methods of making, implanting, and using the same will be described. Then, the hemodynamic flow characteristics of some illustrative devices will be described, as well as a method for using an hourglass-shaped device to noninvasively determine left atrial pressure based on images of blood flowing through the implanted device. Some alternative embodiments will then be described. An Example will be provided that describes a study performed on several animals into which an exemplary device was implanted, as compared to a group of control animals. Apparatus for delivering the devices of the present invention also will be described.

FIGS. 1A-1D illustrate perspective views of an illustrative embodiment of the inventive device. First, with reference to FIG. 1A, device 100 includes an hourglass-shaped stent 110 and optional tissue valve 130, illustratively, a tricuspid valve including three coapting leaflets. Device 100 has three general regions: first flared or funnel-shaped end region 102, second flared or funnel-shaped end region 106, and neck region 104 disposed between the first and second flared end regions. Neck region 104 is configured to lodge in a puncture formed in the atrial septum, preferably in the fossa ovalis, using methods described in greater detail below. First flared end region 102 is configured to engage the right side of the atrial septum, and second flared end region 106 is configured to flank the left side of the atrial septum, when implanted. The particular dimensions and configurations of neck region 104 and first and second flared end regions 102, 106 may be selected so as to inhibit the formation of eddy currents when implanted, and thus inhibit thrombus formation; to inhibit tissue ingrowth in selected regions; to promote tissue ingrowth in other selected regions; and to provide a desirable rate of blood flow between the left and right atria.

Figure 1A:
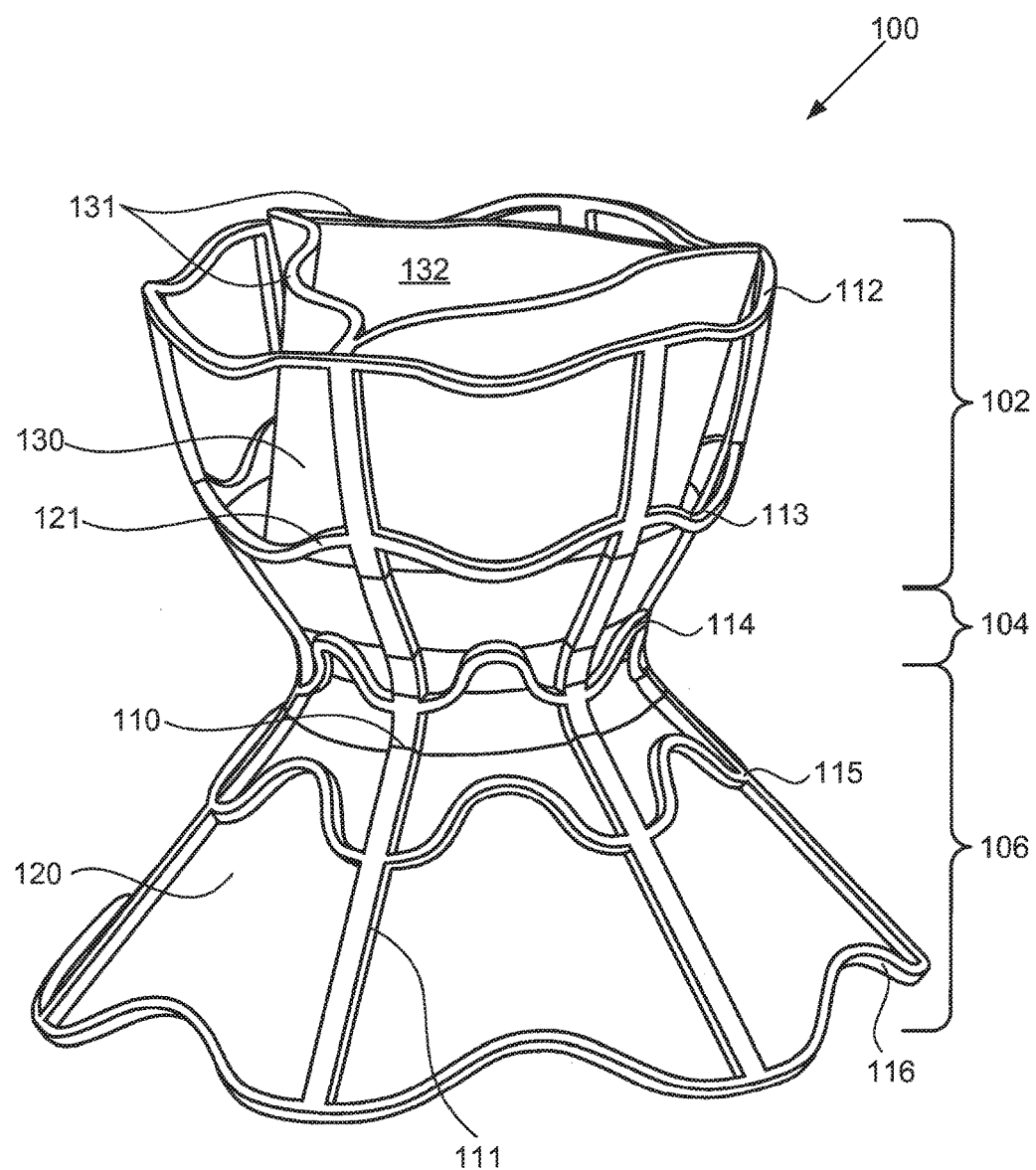

Hourglass-shaped stent 110 is preferably formed of a shape memory metal, e.g., NITINOL, or any other suitable material known in the art. Stent 110 includes a plurality of sinusoidal rings 112-116 interconnected by longitudinally extending struts 111. Rings 112-116 and struts 111 may be of unitary construction, that is, entire stent 110 may be laser cut from a tube of shape memory metal. As can be seen in FIG. 1A, neck region 104 and second flared end region 106 are covered with biocompatible material 120, for example a sheet of a polymer such as expanded polytetrafluoroethylene (ePTFE), silicone, polycarbonate urethane, DACRON (polyethylene terephthalate), or polyurethane, or of a natural material such as pericardial tissue, e.g., from an equine, bovine, or porcine source. Specifically, the region extending approximately from sinusoidal ring 113 to sinusoidal ring 116 is covered with biocompatible material 120. Material 120 preferably is generally smooth so as to inhibit thrombus formation, and optionally may be impregnated with carbon so as to promote tissue ingrowth. Preferably, portions of stent 110 associated with first flared end region 102 are not covered with the biocompatible material, but are left as bare metal, so as to inhibit the formation of stagnant flow regions in the right atrium that otherwise and to provide substantially free blood flow around leaflets 131, so as to inhibit significant tissue growth on leaflets 131. The bare metal regions of stent 110, as well as any other regions of the stent, optionally may be electropolished or otherwise treated so as to inhibit thrombus formation, using any suitable method known in the art.

An inlet end of tissue valve 130 is coupled to stent 110 in first flared end region 102. In the illustrated embodiment, tissue valve 130 is a tricuspid valve that includes first, second, and third leaflets 131 defining valve opening 132. Other embodiments, illustrated further below, may include a bicuspid or duckbill valve, or other suitable valve construction. However, it is believed that tricuspid valves may provide enhanced leaflet coaptation as compared to other valve types, such that even if the tissue valve stiffens as a result of tissue ingrowth following implantation, there may still be sufficient leaflet material to provide coaptation with the other leaflets and close the valve. Preferably, tissue valve 130 opens at a pressure of less than 1 mm Hg, closes at a pressure gradient of between 0-0.5 mm Hg, and remains closed at relatively high back pressures, for example at back pressures of at least 40 mm Hg. Tissue valve 130 may be formed using any natural or synthetic biocompatible material, including but not limited to pericardial tissue, e.g., bovine, equine, or porcine tissue, or a suitable polymer. Pericardial tissue, and in particular bovine pericardial tissue, is preferred because of its strength and durability. The pericardial tissue may be thinned to enhance compliance, for example as described in greater detail below, and may be fixed using any suitable method, for example, using glutaraldehyde or other biocompatible fixative.

Figure 1B:
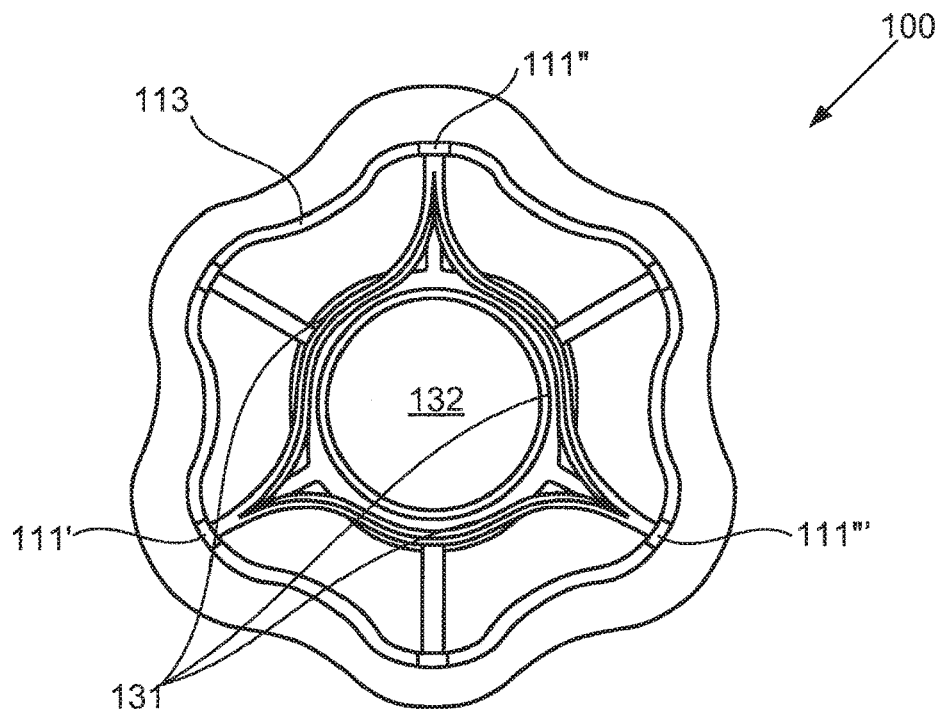

As shown in FIG. 1B, tissue valve 130 is coupled, e.g., sutured, to first, second, and third longitudinally extending struts 111', 111", and 111''' in the region extending between first (uppermost) sinusoidal ring 112 and second sinusoidal ring 113. Referring to FIGS. 1A and 1D, tissue valve 130 is also coupled to the upper edge of biocompatible material 120, at or near sinusoidal ring 113, for example along line 121 as shown. As such, tissue valve 130 and biocompatible material 120 together provide a smooth profile to guide blood flow from the left atrium to the right atrium, that is, from the second flared end region 106, through neck region 104, and through first flared end region 102. In accordance with one aspect of the invention, the inlet to tissue valve 130 is anchored to neck region 104, such that leaflets 131 extend into the right atrium. In this manner, any eccentricities that may arise from the out-of-roundness of the puncture through the fossa ovalis during implantation will not be transferred to the free ends of leaflets 131, thus reducing the risk that any eccentricity of the stent in neck region 104 could disturb proper coaptation of the valve leaflets.

Figure 1C:
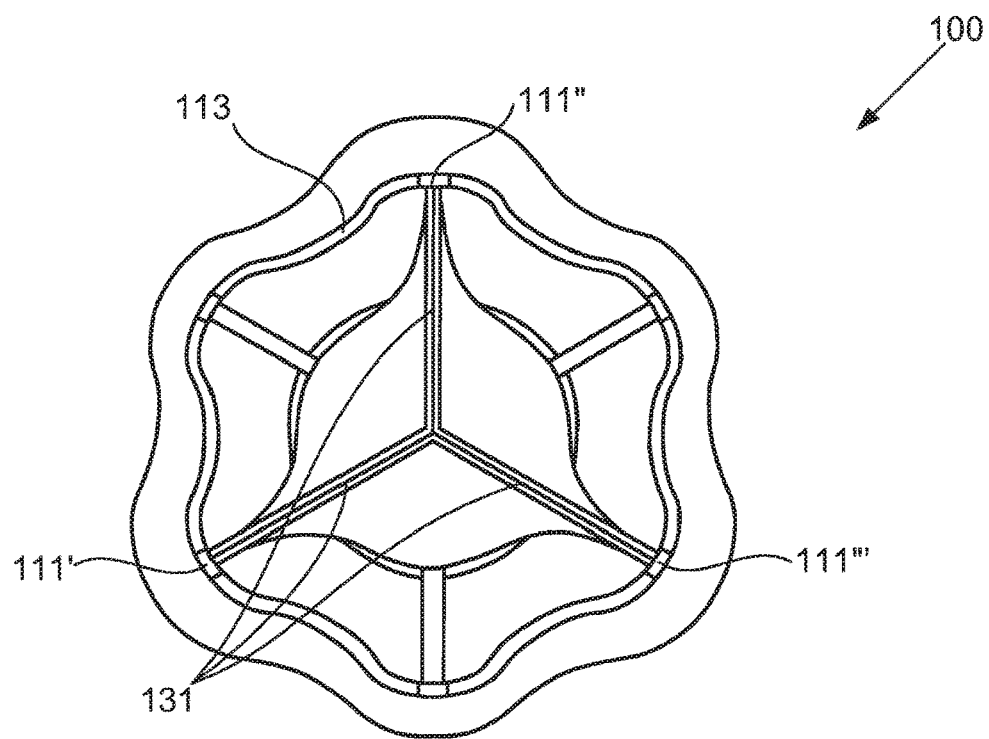
Figure 1D:
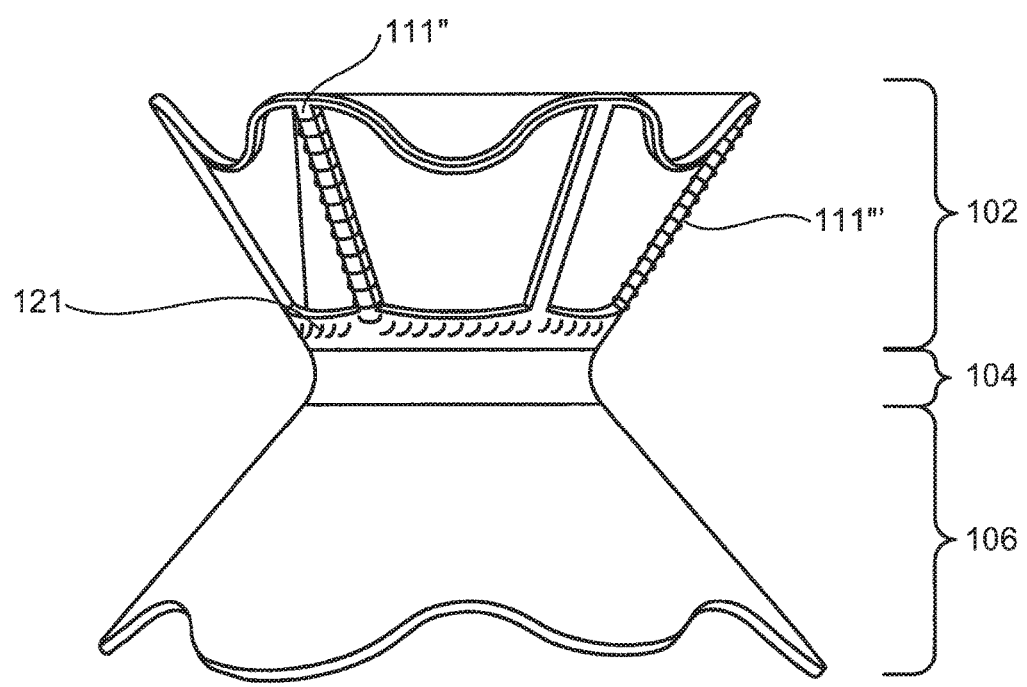

FIGS. 1A and 1B illustrate device 100 when tissue valve 130 is in an open configuration, in which leaflets 131 are in an open position to permit flow, and FIG. 1C illustrates device 100 when tissue valve 130 is in a closed configuration, in which leaflets 131 are in a closed position to inhibit flow. Tissue valve 130 is configured to open when the pressure at second flared end region 106 exceeds that at first flared end region 102. Preferably, however, tissue valve 130 is configured to close and therefore inhibit flow in the opposite direction, i.e., to inhibit flow from first flared end region 102, through neck region 104, and through second flared end region 104, when the pressure at the first flared end region exceeds that of the second. Among other things, such a feature is expected to inhibit passage of thrombus from the right atrium to the left atrium, which could cause stroke or death. Moreover, allowing flow of blood with low oxygenation from right to left would further aggravate CHF. Further, tissue valve 130 preferably is configured to close and therefore inhibit flow in either direction when the pressures at the first and second flared end regions are approximately equal. Preferably, tissue valve 130 is sized and has dynamic characteristics selected to maintain a pressure differential between the left and right atria of 15 mm Hg or less.

To achieve such flow effects, as well as reduce complexity of device fabrication, tissue valve 130 preferably is a tricuspid valve, as is illustrated in FIGS. 1A-1D, but alternatively may be a bicuspid valve, for example a duckbill valve, or a mitral valve, as described here after with respect to FIGS. 8A-8C and 9. For example, as described in greater detail below with respect to FIGS. 3A-3E, tissue valve 130 may be formed of a single piece of thinned animal pericardial tissue that is sutured along at least one edge to form an open-ended conical or ovoid tube, and then three-dimensionally fixed to assume a normally closed position. The inlet or bottom (narrower) end of the tube may be coupled, e.g., sutured, to biocompatible material 120 at or near sinusoidal ring 113, and the sides of the tube optionally may be sutured to struts 111', 111", and 111''', as illustrated in FIG. 1D (strut 111' not shown in FIG. 1D). In one embodiment, the bottom end of the tube is sutured to biocompatible material 120 along substantially straight line 121 that is approximately 2-3 mm to the right of the narrowest portion of neck region 104. Without wishing to be bound by theory, it is believed that such a location for line 121 may be sufficiently large as to inhibit tissue from atrial septum 210 from growing into tissue valve 130. In another embodiment (not illustrated), the bottom end of tissue valve 130 is secured, e.g., sutured to biocompatible material 120 along a curve that follows the shape of sinusoidal ring 113. During use, the outlet or upper (wider) end of the tube may open and close based on the pressure differential between the inlet and outlet ends, that is, between the left and right atria when implanted. Other suitable valve configurations may include bicuspid valves, duckbill valves, sleeve (windsock) valves, flap valves, and the like.

As noted above, hourglass-shaped device 100 preferably is configured for implantation through the fossa ovalis of the atrial septum, particularly through the middle of the fossa ovalis. As known to those skilled in the art, the fossa ovalis is a thinned portion of the atrial septum caused during fetal development of the heart, which appears as an indent in the right side of the atrial septum and is surrounded by a thicker portion of the atrial septum. While the atrial septum itself may be several millimeters thick and muscular, the fossa ovalis may be only approximately one millimeter thick, and is formed primarily of fibrous tissue. Advantageously, because the fossa ovalis comprises predominantly fibrous tissue, that region of the atrial septum is not expected to undergo significant tension or contraction during the cardiac cycle, and thus should not impose significant radial stresses on stent 110 that could lead to stress-induce cracking. In addition, the composition of the fossa ovalis as primarily fibrous tissue is expected to avoid excessive endothelialization after implantation.

Figure 2A:
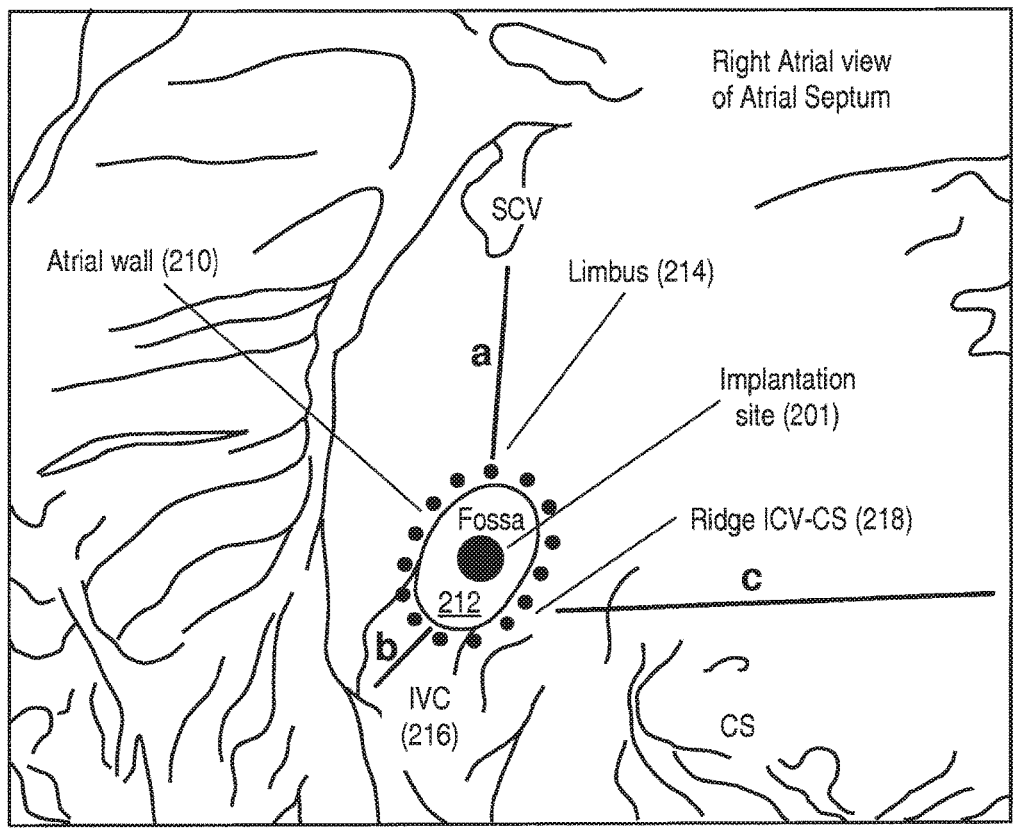
Figure 2B:
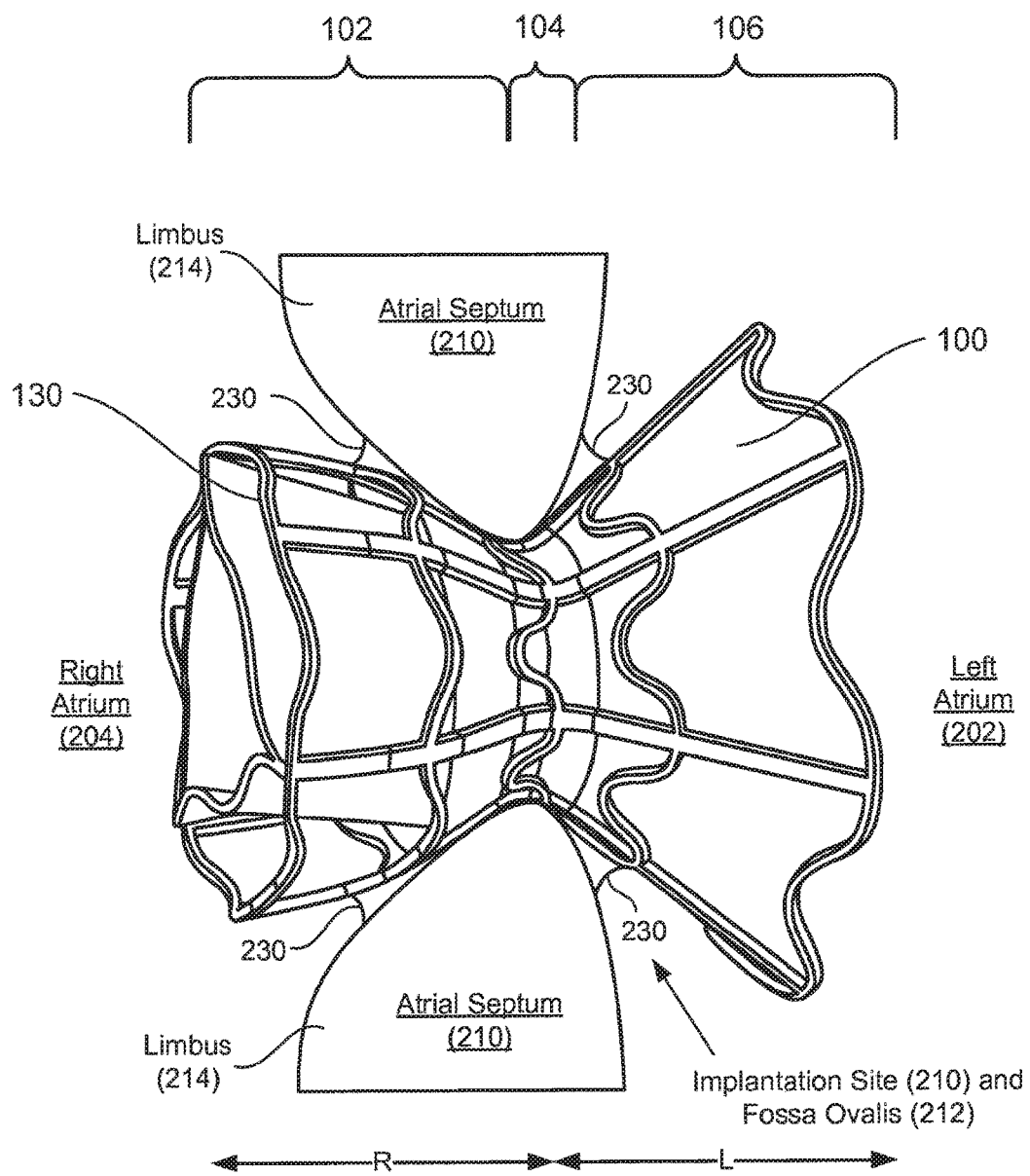

In some embodiments of the present invention, hourglass-shaped device 100 is asymmetrically shaped to take advantage of the natural features of atrial septum 210 near the fossa ovalis, and to provide suitable flow characteristics. FIG. 2A illustrates a plan view of the right atrial side of the atrial septum 210, including an implantation site 201 through the fossa ovalis 212. Preferably, the implantation site 201 is through the middle of the fossa ovalis 212, so that the device may be implanted at a spaced distance from the surrounding limbus 214, inferior vena cava (IVC) 216, and atrial wall 210. For example, as illustrated in FIG. 2B, first flared end region 102 is configured to be implanted in right atrium 204 and may be tapered so as to have a more cylindrical shape than does second flared end region 106, which is configured to be implanted in left atrium 202. The more cylindrical shape of first flared end region 102 may enhance opening and closing of tissue valve 130, while reducing risk of the tissue valve falling back towards stent 110; may increase the proportion of tissue valve 130 that moves during each open-close cycle, and thus inhibit tissue growth on the valve; and may reduce or inhibit contact between first flared end region 102 and the limbus 214 of the fossa ovalis 212, that is, between first flared end region 102 and the prominent margin of the fossa ovalis, while still anchoring device 100 across atrial septum 210. The more cylindrical shape of first flared end region 102 further may reduce or inhibit contact between first flared end region 102 and the right atrial wall, as well as the ridge 218 separating the coronary sinus from the inferior vena cava (IVC) (shown in FIG. 2A but not FIG. 2B). Additionally, in some embodiments the first flared end region 102 substantially does not extend beyond the indent of the fossa ovalis in the right atrium, and therefore substantially does not restrict blood flow from the IVC 216.

In accordance with one aspect of the invention, device 100 preferably is configured so as to avoid imposing significant mechanical forces on atrial septum 210 or atria 202, 204, allowing the septum to naturally deform as the heart beats. For example, muscular areas of septum 210 may change by over 20% between systole and diastole. It is believed that any significant mechanical constraints on the motion of atrial septum 210 in such areas would lead to the development of relatively large forces acting on the septum and/or on atrial tissue that contacts device 100, which potentially would otherwise cause the tissue to have an inflammatory response and hyperplasia, and possibly cause device 100 to eventually lose patency. However, by configuring device 100 so that neck region may be implanted entirely or predominantly in the fibrous tissue of the fossa ovalis 212, the hourglass shape of device 100 is expected to be sufficiently stable so as to be retained in the septum, while reducing mechanical loads on the surrounding atrial septum tissue 210. As noted elsewhere herein, tissue ingrowth from atrial septum 210 in regions 230 may further enhance binding of device 100 to the septum.

Also, for example, as illustrated in FIG. 2B, neck region 104 of device 100 is significantly narrower than flared end regions 102, 106, facilitating device 100 to "self-locate" in a puncture through atrial septum 210, particularly when implanted through the fossa ovalis. In some embodiments, neck region 104 may have a diameter suitable for implantation in the fossa ovalis, e.g., that is smaller than the fossa ovalis, and that also is selected to inhibit blood flow rates exceeding a predetermined threshold. For example, the smallest diameter of neck 104 may be between about 3 and 8 mm, e.g., between about 5 mm and 7 mm, preferably between about 5.5 mm and 6.5 mm. For example, it is believed that diameters of less than about 4.5 mm may in some circumstances not allow sufficient blood flow through the device to decompress the left atrium, and may reduce long-term patency of device 100, while diameters of greater than about 5.5 mm may allow too much blood flow. For example, flow rates of greater than 2 liters/minute, or even greater than 1.0 liters/minute are believed to potentially lead to right heart failure.

In some embodiments, the length of first flared end region 102 also may be selected to protrude into the right atrium by a distance R between the narrowest portion of neck region 104 and the end of first flared region 102 may be approximately 5.0 to 9.0 mm, for example about 5.5 to about 7.5 mm, or about 6 to about 7 mm, so as not to significantly protrude above the limbus of fossa ovalis 212. Second flared end region 106 preferably does not significantly engage the left side of atrial septum 210, and distance L may be between 2.0 and 8.0 mm, for example about 4 to 7 mm, or about 6.0 mm. It is believed that configuring first and second flared end regions 102, 106 so as to extend by as short a distance as possible into the right and left atria, respectively, while still maintaining satisfactory flow characteristics and stabilization in atrial septum 210, may reduce blockage of flow from the inferior vena cava (IVC) in the right atrium and from the pulmonary veins in the left atrium. In one illustrative embodiment, distance R is about 6.5 mm and distance L is about 6.0 mm. In some embodiments, the overall dimensions of device 100 may be 8-20 mm long (L+R, in FIG. 2B), e.g., about 10-15 mm, e.g., about 11-14 mm, e.g., about 12.5 mm.

The diameters of the first and second flared end regions further may be selected to stabilize device 100 in the puncture through atrial septum 210, e.g., in the puncture through fossa ovalis 212. For example, first flared end region 102 may have a diameter of 8-15 mm at its widest point, e.g., about 10-13 mm or about 11.4 mm; and second flared end region 106 may have a diameter of 10-20 mm at its widest point, e.g., about 13-16 mm or about 14.4 mm. The largest diameter of first flared end region 102 may be selected so as to avoid mechanically loading the limbus of the fossa ovalis 212, which might otherwise cause inflammation. The largest diameter of second flared end region 106 may be selected so as to provide a sufficient angle between first and second flared end regions 102, 106 to stabilize device 100 in the atrial septum, while limiting the extent to which second flared end region 106 protrudes into the left atrium (e.g., inhibiting interference with flow from the pulmonary veins), and providing sufficient blood flow from the left atrium through neck region 104. In one embodiment, the angle between the first and second flared end regions is about 70-140 degrees, e.g., about 90 to 130 degrees, e.g., about 100 degrees. Such an angle may stabilize device 100 across the fossa ovalis, while inhibiting excessive contact between the device and the atrial septum. Such excessive contact might cause inflammation because of the expansion and contraction of the atrial septum during the cardiac cycle, particularly between diastole and systole. In one embodiment, the first flared end region subtends an angle of approximately 80 degrees, that is, the steepest part of the outer surface of the first flared end region is at an angle of approximately 40 degrees relative to a central longitudinal axis of the device. The second flared end region may flare by about 30-70 degrees, where the steepest part of the outer surface of the second flared end region may be at an angle of approximately 35 degrees relative to the central longitudinal axis of the device. The second flare may be have a tapered shape starting with a wider angle in the range of about 50-70 degrees and end with a narrow angle in the range of about 30-40 degrees.

Tissue valve 130 is preferably configured such that when closed, leaflets 131 define approximately straight lines resulting from tension exerted by stent 110 across valve opening 132, as illustrated in FIG. 1C. Additionally, the transition between tissue valve 130 and biocompatible material 120 preferably is smooth, so as to reduce turbulence and the possibility of flow stagnation, which would increase coagulation and the possibility of blockage and excessive tissue ingrowth. As pressure differentials develop across tissue valve 130 (e.g., between the left and right atria), blood flow preferably follows a vector that is substantially perpendicular to the tension forces exerted by stent 110, and as such, the equilibrium of forces is disrupted and leaflets 131 start to open. As the leaflets open, the direction of tension forces exerted by stent 110 change, enabling an equilibrium of forces and support of continuous flow. An equilibrium position for each pressure differential is controlled by the geometry of tissue valve 130 and the elastic behavior of stent 110. When a negative pressure differential (right atrial pressure greater than left atrial pressure) develops, valve leaflets 131 are coapt, closing the tissue valve and the prevention of right to left backflow.

When device 100 is implanted across the atrial septum, as illustrated in FIG. 2B, left atrial pressures may be regulated in patients having congestive heart failure (CHF). For example, device 100 may reduce pressure in the left atrium by about 2-5 mmHg immediately following implantation. Such a pressure reduction may lead to a long-term benefit in the patient, because a process then begins by which the lowered left atrial pressure reduces the transpulmonary gradient, which reduces the pulmonary artery pressure. However, the right atrial pressure is not significantly increased because the right atrium has a relatively high compliance. Furthermore, the pulmonary capillaries may self-regulate to accept high blood volume if needed, without increasing pressure. When the left atrial pressure is high, the pulmonary capillaries constrict to maintain the transpulmonary gradient, but as the left atrial pressure decreases, and there is more blood coming from the right atrium, there are actually higher flow rates at lower pressures passing through the pulmonary circulation. After a period of between a few hours and a week following implantation of device 100, the pulmonary circulation has been observed to function at lower pressures, while the systemic circulation maintains higher pressures and thus adequate perfusion. The resulting lower pulmonary pressures, and lower left ventricle end diastolic pressure (LVEDP) decrease the after load by working at lower pressures, resulting in less oxygen demand and less resistance to flow. Such small decreases in afterload may dramatically increase the cardiac output (CO) in heart failure, resulting in increased ejection fraction (EF). Moreover, because of the release in the afterload and in the pressures of the pulmonary circulation, the right atrial pressure decreases over time as well. Following myocardial infarction, the effect is even more pronounced, because the period after the infarction is very important for the remodeling of the heart. Specifically, when the heart remodels at lower pressures, the outcome is better.

In the region of contact between device 100 and atrial septum 210, preferably there is limited tissue growth. The connective tissue of atrial septum 210 is non-living material, so substantially no nourishing of cells occurs between the septum and device 100. However, local stagnation in flow may lead to limited cell accumulation and tissue growth where device 100 contacts atrial septum 210, for example in regions designated 230 in FIG. 2B. Such tissue growth in regions 230 may anchor device 210 across atrial septum 210. Additional, such tissue growth may cause the flow between the external surface of device 100 and atrial septum 210 to become smoother and more continuous, thus reducing or inhibiting further cell accumulation and tissue growth in regions 230. As noted above, first flared end region 102 of stent 110, e.g., between the line along which tissue valve 130 is coupled to biocompatible material 120 and first sinusoidal ring 112 preferably is bare metal. This configuration is expected to inhibit formation of stagnation points in blood flow in right atrium 204, that otherwise may lead to tissue growth on the external surfaces of leaflets 131 of tissue valve 130.

A method 300 of making device 100 illustrated in FIGS. 1A-1D and FIG. 2B will now be described with respect to FIGS. 3A-3E.

Figure 3A:
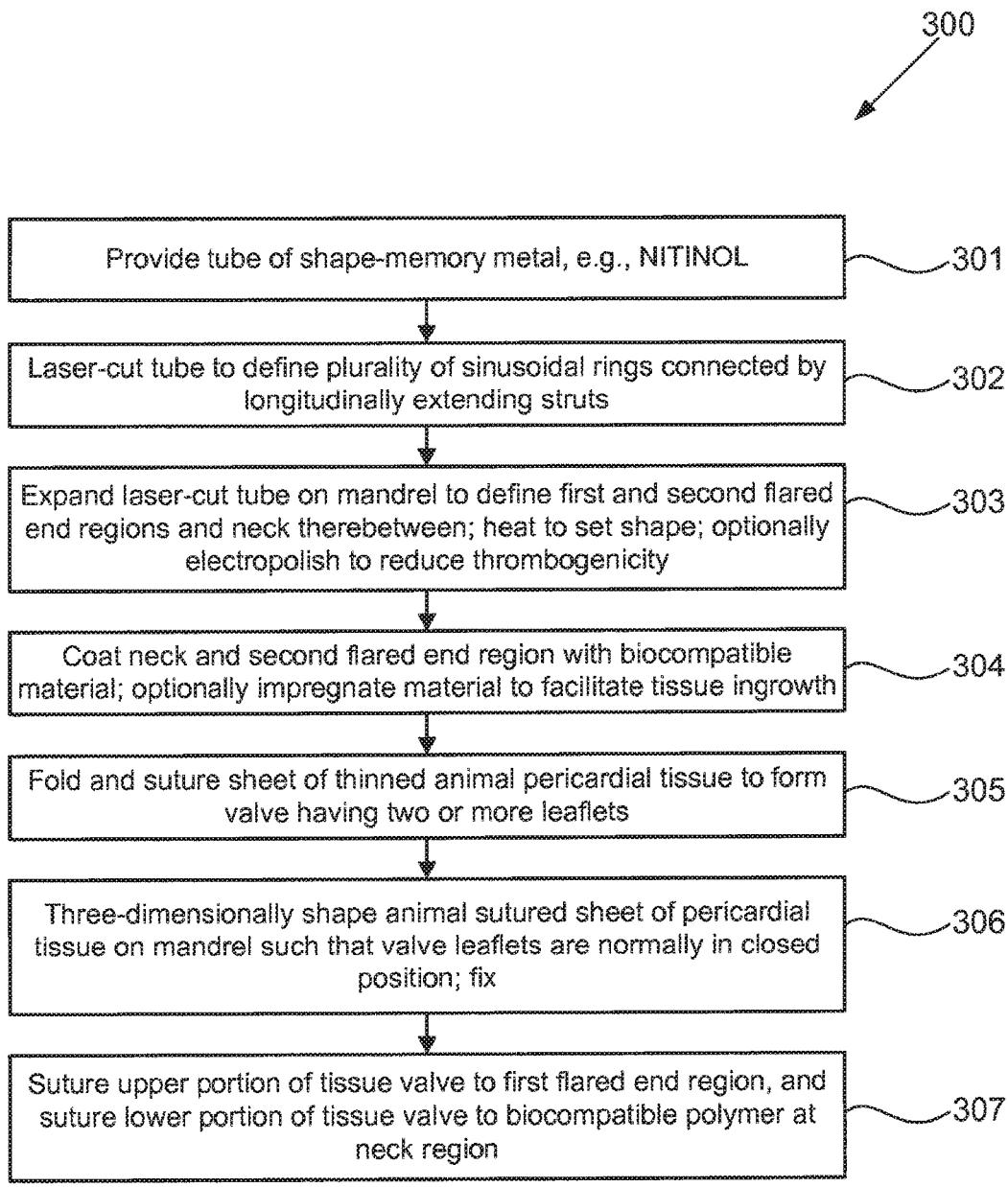
FIG. 3A is a flow chart of steps in a method of making an hourglass-shaped device, according to some embodiments of the present invention.

First, a tube of shape-memory material, e.g., a shape-memory metal such as nickel titanium (NiTi), also known as NITINOL, is provided (step 301 of FIG. 3A). Other suitable materials known in the art of deformable stents for percutaneous implantation may alternatively be used, e.g., other shape memory alloys, polymers, and the like. In one embodiment, the tube has a thickness of 0.25 mm.

Then, the tube is laser-cut to define a plurality of sinusoidal rings connected by longitudinally extending struts (step 302). For example, struts 111 and sinusoidal rings 112-116 illustrated in FIG. 1A may be defined using laser cutting a single tube of shape-memory metal, and thus may form an integral piece of unitary construction. Alternatively, struts 111 and sinusoidal rings 112-116 may be separately defined from different pieces of shape-memory metal and subsequently coupled together.

Referring again to FIG. 3A, the laser-cut tube then is expanded on a mandrel to define first and second flared end regions and a neck therebetween, e.g., to define first end region 102, second end region 106, and neck region 104 as illustrated in FIG. 1A; the expanded tube then may be heated to set the shape of stent 110 (step 303). In one example, the tube is formed of NITINOL, shaped using a shape mandrel, and placed into an oven for 11 minutes at 530 C to set the shape. Optionally, the stent thus defined also may be electropolished to reduce thrombogenicity, or otherwise suitably treated. Such electropolishing may alternatively be performed at a different time, e.g., before shaping using the mandrel.

As shown in FIG. 3A, the neck and second flared end region of the stent then may be coated with a biocompatible material (step 304). Examples of suitable biocompatible materials include expanded polytetrafluoroethylene (ePTFE), polyurethane, DACRON (polyethylene terephthalate), silicone, polycarbonate urethane, and animal pericardial tissue, e.g., from an equine, bovine, or porcine source. In one embodiment, the stent is coated with the biocompatible material by covering the inner surface of the stent with a first sheet of ePTFE, and covering the outer surface of the stent with a second sheet of ePTFE. The first and second sheets first may be temporarily secured together to facilitate the general arrangement, e.g., using an adhesive, suture, or weld, and then may be securely bonded together using sintering to form a strong, smooth, substantially continuous coating that covers the inner and outer surfaces of the stent. Portions of the coating then may be removed as desired from selected portions of the stent, for example using laser-cutting or mechanical cutting. For example, as shown in FIG. 1A, biocompatible material 120 may cover stent 110 between sinusoidal ring 113 and sinusoidal ring 116, i.e., may cover neck region 104 and second flared end region 106, but may be removed between sinusoidal ring 113 and sinusoidal ring 112, i.e., may be removed from (or not applied to) first flared end region 102.

The biocompatible material facilitates funneling of blood from the left atrium to the right atrium by facilitating the formation of a pressure gradient across tissue valve 130, as well as providing a substantially smooth hemodynamic profile on both the inner and outer surfaces of device 100. Advantageously, this configuration is expected to inhibit the formation of eddy currents that otherwise may cause emboli to form, and facilitates smooth attachment of the device to the atrial septum, e.g., fossa ovalis. Biocompatible material 120 preferably is configured so as to direct blood flow from the left atrium, through neck region 104 and toward tissue valve leaflets 131. Biocompatible material 120 preferably also is configured so as to inhibit tissue growth from atrial septum 210 and surrounding tissue into device 100 and particularly toward tissue valve leaflets 131. In some embodiments, the biocompatible material 120 has a porosity that is preselected to allow limited cell growth on its surface; the cells that grow on such a surface preferably are endothelial cells that are exposed to blood and inhibit blood from coagulating on the biocompatible material. After such cells grow on the biocompatible material 120, the material preferably is substantially inert and thus not rejected by the body. Optionally, the biocompatible material may be impregnated with a second material that facilitates tissue ingrowth, e.g., carbon. Such impregnation may be performed before or after applying the biocompatible material to the stent.

Figure 3B:
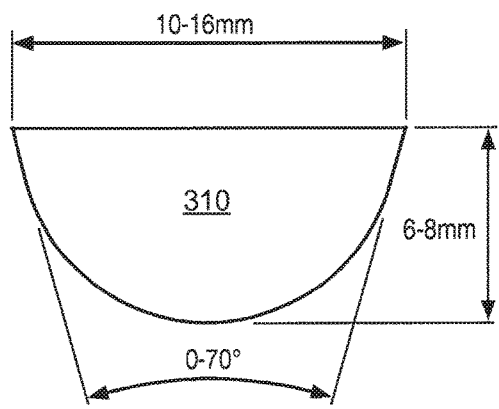
FIGS. 3B-3E illustrate plan views of sheets of material for use in preparing tissue valves, according to some embodiments of the present invention.
Figure 3C:
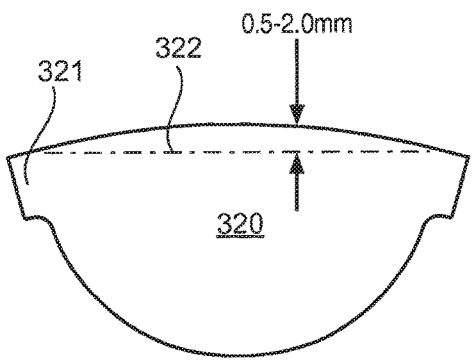
Figure 3D:
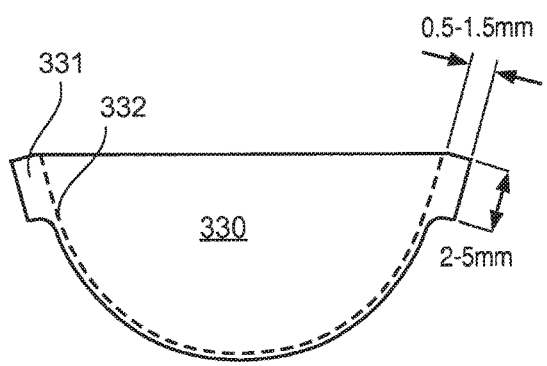
Figure 3E:
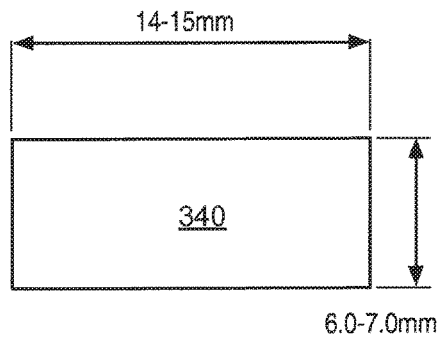

Then, as shown in FIG. 3A, a valve having two or more leaflets, such as a tricuspid, bicuspid, or duckbill valve, or any other suitable valve, is formed by folding and suturing a sheet of thinned animal pericardial tissue, e.g., equine, bovine, or porcine material (step 305). FIGS. 3B-3E illustrate plan views of exemplary sheets of animal pericardial tissue that may be used to form tissue valves. Specifically, FIG. 3B illustrates an approximately semicircular sheet 310 of tissue for use in preparing a tricuspid tissue valve. Although the sheet 310 may be any suitable dimensions, in the illustrated embodiment the sheet has a width of 10-16 mm, a length of 6-8 mm. The opposing edges may be at an angle between 0-70 degrees relative to one another so that when the sheet is folded and those edges are secured, e.g., sutured together, sheet 310 forms a generally funnel-like shape having approximately the same angle as the first flared end region to which it is to be secured. FIG. 3C illustrates an embodiment similar to that of FIG. 3B, but in which sheet 320 also includes wings 321 providing additional tissue material in regions along the suture line that may be subjected to high stresses, as well as a curved top contour 322 that provides an extended region for coaptation between the leaflets when the valve is closed. Wings may be approximately 2-5 mm long, and extend 0.5-1.5 mm beyond the lateral edges of sheet 320. FIG. 3D illustrates an embodiment similar to that of FIG. 3C, e.g., that includes wings 331 that may be of similar dimension as wings 321, but in which sheet 330 lacks a curved top contour. Sutures 332 are shown in FIG. 3D. FIG. 3E illustrates a sheet 340 of tissue suitable for use in preparing a bicuspid tissue valve, that has a generally rectangular shape, for example having a width of 14-15 mm and a length of 6.0-7.0 mm. Other dimensions may suitably be used. For example, the tissue sheet may have a flattened length of no greater than 18 mm, for example, a length of 10-16 mm, or 12-14 mm, or 14-18 mm, and may be folded and sutured to define two or more leaflets each having a length of, for example, 9 mm or less, or 8 mm or less, or 7 mm or less, or 6 mm or less, or even 5 mm or less, e.g., 5-8 mm. The tissue sheet may have a flattened height no greater than 10 mm, for example, a height of 2-10 mm, or 4-10 mm, or 4-8 mm, or 6-8 mm, or 4-6 mm. The tissue sheet may have a flattened area of no greater than 150 square mm, for example, 60-150 square mm, or 80-120 square mm, or 100-140 square mm, or 60-100 square mm. In some exemplary embodiments, the sheet of tissue may have a generally trapezoidal or "fan" shape, so that when opposing edges are brought together and sutured together, the sheet has a general "funnel" shape, with a wide opening along the outlet or upper edge and a narrow opening along the inlet or lower edge. Note that other suitable methods of securing opposing edges of the sheet alternatively may be used, e.g., adhesive, welding, and the like.

The tissue may have a thickness, for example, of between 0.050 mm and 0.50 mm, for example, about 0.10 mm and 0.20 mm. Typically, harvested bovine pericardial tissue has a thickness between about 0.3 mm and 0.5 mm, which as is known in the art is a suitable thickness for high-stress applications such as construction of aortic valves. However, for use in the device of the present invention, it may be preferable to thin the pericardial tissue. For example, the stresses to which the valve leaflets are exposed in a device constructed in accordance with the present invention may be a small fraction (e.g., ½5th) of the stresses in an aortic valve application, because of the relatively large surface area of the leaflets and the relatively low pressure gradients across the device. For this reason, thinned pericardial tissue may be used, enabling construction of a more compliant valve that may be readily fixed in a normally closed position but that opens under relatively low pressure gradients. Additionally, the use of thinner leaflets is expected to permit the overall profile of the device to be reduced in when the device is compressed to the contracted delivery state, thereby enabling its use in a wider range of patients.

For example, harvested pericardial tissue typically includes three layers: the smooth and thin mesothelial layer, the inner loose connective tissue, and the outer dense fibrous tissue. The pericardial tissue may be thinned by delaminating and removing the dense fibrous tissue, and using a sheet of the remaining mesothelial and loose connective layers, which may have a thickness of 0.10 mm to 0.20 mm, to construct the tissue valve. The dense fibrous tissue may be mechanically removed, for example using a dermatome, grabbing tool, or by hand, and any remaining fibers trimmed.

The animal pericardial tissue then may be three-dimensionally shaped on a mandrel to define a tissue valve having valve leaflets that are normally in a closed position, and then fixed in that position using glutaraldehyde or other suitable substance (step 306). Excess glutaraldehyde may be removed using an anticalcification treatment, for example to inhibit the formation of calcium deposits on the tissue valve.

The outlet or upper (wider) portion of the tissue valve then may be secured, e.g., sutured, to the first flared end region, and the inlet or lower (narrower) portion of the tissue valve secured, e.g., sutured to the biocompatible polymer at the neck region (step 307). For example, as illustrated in FIGS. 1A-1D, the lower portion of tissue valve 130 may be secured using sutures to biocompatible material 120 at or near sinusoidal ring 113 (for example, along a line 121 approximately 2-3 mm to the right of the narrowest portion of neck region 104), and also may be sutured to elongated struts 111', 111", and 111'" so as to define a tricuspid valve having leaflets 131. Other suitable methods of securing the tissue valve to stent 110 and to biocompatible material 120 may alternatively be used. Preferably, tissue valve 130 is secured to device 100 such that, when implanted, the tissue valve is disposed substantially only in the right atrium. Such a configuration may facilitate flushing of the external surfaces of leaflets 131 with blood entering the right atrium. By comparison, it is believed that if leaflets 131 were instead disposed within neck region 104 or second flared end region 106, they might inhibit blood flow and/or gradually lose patency over time as a result of tissue ingrowth caused by the stagnation of blood around the leaflets.

A method 400 of using device 100 illustrated in FIGS. 1A-1D to reduce left atrial pressure in a subject, for example, a human having CHF, will now be described with reference to FIG. 4. Some of the steps of method 400 may be further elaborated by referring to FIGS. 5A-5D.

First, an hourglass-shaped device having a plurality of sinusoidal rings connected by longitudinally extending struts that define first and second flared end regions and a neck disposed therebetween, as well as a tissue valve coupled to the first flared end region, is provided (step 401). Such a device may be provided, for example, using method 300 described above with respect to FIGS. 3A-3E.

Figure 5A:
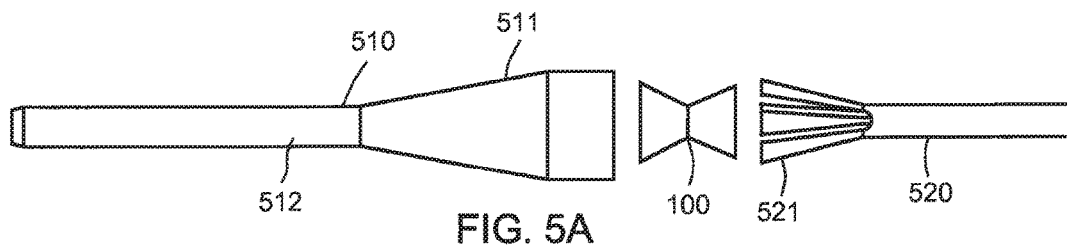
Figure 5B:
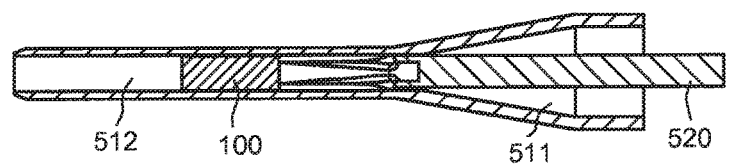

Then, the device is collapsed radially to a contracted delivery state, and loaded into a loading tube (step 402). For example, as illustrated in FIGS. 5A-5B, device 100 may be loaded into loading tube 510 using pusher 520 having "star"-shaped end 521. Loading tube 510 includes tapered loading end 511, which facilitates radial compression of device 100 into lumen 512 having a suitable internal diameter. Once device 100 is loaded into lumen 512, pusher 520 is retracted. Preferably, device 100 is loaded into loading tube 510 shortly before implantation, so as to avoid unnecessarily compressing device 100 or re-setting of the closed shape of leaflets 132, which may interfere with later deployment or operation of the device. In some embodiments, loading tube 510 has a diameter of 16 F or less, or 14 F or less, or 10 F or less, or 6 F or less, e.g., about 5 F, and device 100 has a crimped diameter of 16 F or less, or 14 F or less, or 10 F or less, or 6 F or less, e.g., about 5 F. In one illustrative embodiment, loading tube has a diameter of 15 F and device 100 has a crimped diameter of 14 F.

Figure 5C:
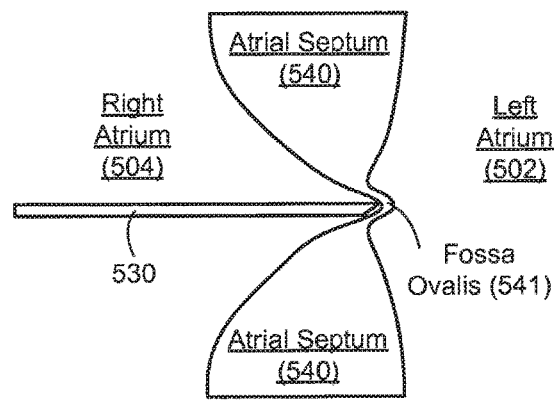

Referring again to FIG. 4, the device then is implanted, first by identifying the fossa ovalis of the heart septum, across which device 100 is to be deployed (step 403). Specifically, a BROCKENBROUGH needle may be percutaneously introduced into the right atrium via the subject's venous vasculature, for example, via the femoral artery. Then, under fluoroscopic or echocardiographic visualization, the needle is pressed against the fossa ovalis, at a pressure insufficient to puncture the fossa ovalis. As illustrated in FIG. 5C, the pressure from needle 530 causes "tenting" of fossa ovalis 541, i.e., causes the fossa ovalis to stretch into the left atrium. Other portions of atrial septum 540 are thick and muscular, and so do not stretch to the same extent as the fossa ovalis. Thus, by visualizing the extent to which different portions of the atrial septum 540 tents under pressure from needle 530, fossa ovalis 541 may be identified, and in particular the central portion of fossa ovalis 541 may be located.

Referring again to FIG. 4, the fossa ovalis (particularly its central region) may be punctured with the BROCKENBROUGH needle, and a guidewire may be inserted through the puncture by threading the guidewire through the needle and then removing the needle (step 404, not illustrated in FIG. 5). The puncture through the fossa ovalis then may be expanded by advancing a dilator over the guidewire. Alternatively, a dilator may be advanced over the BROCKENBROUGH needle, without the need for a guidewire. The dilator is used to further dilate the puncture and a sheath then is advanced over the dilator and through the fossa ovalis; the dilator and guidewire or needle then are removed (step 405, not illustrated in FIG. 5). The loading tube, with device 100 disposed in a contracted delivery state therein, then is advanced into the sheath (step 406, not illustrated in FIG. 5).

Figure 5D:
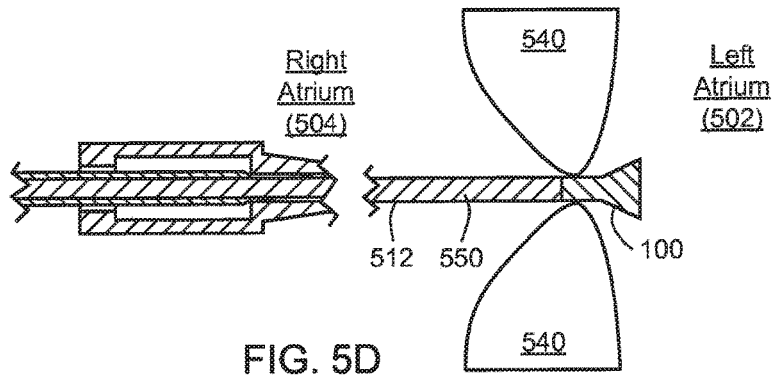

The device then is advanced out of the loading tube and into the sheath using a pusher, and then partially advanced out of the sheath, such that the second flared end of the device protrudes out of the sheath and into the left atrium, and expands to its deployed state (step 407). For example, as illustrated in FIG. 5D, pusher 550 may be used to partially advance device 100 out of sheath 512 and into left atrium 502, which causes the second flared end region to expand in the left atrium. The pusher may be configured such that it cannot advance the device 100 completely out of the sheath, but instead may only push out the side of the device to be disposed in the left atrium, that is, the second flared end region. After the pusher advances the second flared end region out of the sheath, the pusher may be mechanically locked from advancing the device out any further. For example, an expanded region may be disposed on the end of the pusher proximal to the physician that abuts the sheath and prevents further advancement of the pusher after the second flared end region is advanced out of the sheath. The device then may be fully deployed by pulling the sheath back, causing the second flared end region of the device to engage the left side of the atrial septum. Such a feature may prevent accidentally deploying the entire device in the left atrium.

The sheath then is retracted, causing the second flared end region to flank the left side of the atrial septum and the neck of the device to lodge in the puncture through the fossa ovalis, and allowing expansion of the first flared end of the device into the right atrium (step 408, see also FIG. 2B). Any remaining components of the delivery system then may be removed, e.g., sheath, and loading tube (step 409). Once positioned in the fossa ovalis, the device shunts blood from the left atrium to the right atrium when the left atrial pressure exceeds the right atrial pressure (step 410), thus facilitating treatment and/or the amelioration of symptoms associated with CHF.

The performance characteristics of device 100 were characterized using computational fluid dynamic modeling. FIG. 6A is a cross-sectional image of fluid flow through device 100 in the open configuration, in which intensity indicates fluid velocity through the device. As can be seen in FIG. 6A, there are substantially no points of stagnation or turbulence in the blood flow. The maximum shear stresses within device 100 were calculated to be about 50-60 Pascal, which is significantly lower than values that may lead to thrombus formation, which are above 150 Pascal.

The performance of device 100 was also characterized using hemodynamic testing. FIG. 6B is a plot of the flow rate through device 100 as a function of the pressure differential between the left and right atria, for devices having inner diameters of 3.5 mm (trace 610), 4.2 mm (trace 620), 4.8 mm (trace 630), and 5.2 mm (trace 640). At a pressure differential of 10 mm Hg, it can be seen that the flow rate of the 3.5 mm device was 670 ml/minute; the flow rate of the 4.2 mm device was 1055 ml/minute; the flow rate of the 4.8 mm device was 1400 ml/minute; and the flow rate of the 5.2 mm device was 1860 ml/minute. Based on these measurements, it is believed that devices having inner diameters of 4.5 mm to 4.8 mm may provide suitable flow parameters over time, when implanted, because ingrowth of septal tissue over the first 6 months following implantation may reduce the inner diameter to about 3.5 to 3.8 mm, thus reducing the flow rate to below about 800 ml/minute. At steady state, such a flow rate may reduce the left atrial pressure by 5 mmHg, to around 10-15 mmHg, and may reduce the pressure differential between the left and right atria to about 4-6 mmHg.

Additionally, device 100 was subjected to an accelerated wear and fatigue test for up to 100 million cycles to simulate and predict fatigue durability, and was observed to perform satisfactorily.

The devices and methods described herein may be used to regulate left atrial pressures in patients having a variety of disorders, including congestive heart failure (CHF), as well as other disorders such as patent foramen ovale (PFO), or atrial septal defect (ASD). The devices and methods also may be used to reduce symptoms and complications associated with such disorders, including myocardial infarction. It is believed that patients receiving the device may benefit from better exercise tolerance, less incidence of hospitalization due to acute episodes of heart failure, and reduced mortality rates.

The devices and methods described herein further may be used to non-invasively determine the pressure in the left atrium, and thus to assess the efficacy of the device and/or of any medications being administered to the patient. Specifically, with respect to FIG. 7, method 700 includes imaging an implanted hourglass-shaped device, e.g., device 100 described above with respect to FIGS. 1A-1D (step 701). Such imaging may be ultrasonic, e.g., cardioechographic, or may be fluoroscopic. Using such imaging, the time duration of the opening of tissue valve 130 may be measured (step 702). Based on the measured time duration, the flow of blood through the valve may be calculated (step 703). The left atrial pressure then may be calculated based on the calculated flow, for example, based on a curve such as shown in FIG. 6B (step 704). Based on the calculated left atrial pressure, the efficacy of the valve and/or of any medication may be assessed (step 705). A physician may adjust the medication and/or may prescribe a new treatment plan based on the assessed efficacy of the valve and/or the medication.

Some alternative embodiments of device 100 described above with respect to FIGS. 1A-1D are now described. In particular, tissue valves other than tricuspid valve 130 illustrated above with respect to FIGS. 1A-1D may be employed with device 100. For example, device 800 illustrated in FIGS. 8A-8C includes hourglass-shaped stent 110, which may be substantially the same as stent 110 described above, biocompatible material 120, and duckbill tissue valve 830. Like device 100, device 800 has three general regions: first flared or funnel-shaped end region 102 configured to flank the right side of the atrial septum, second flared or funnel-shaped end region 106 configured to flank the left side of the atrial septum, and neck region 104 disposed between the first and second flared end regions and configured to lodge in a puncture formed in the atrial septum, preferably in the fossa ovalis. Stent 110 includes plurality of sinusoidal rings 112-116 interconnected by longitudinally extending struts 111, which may be laser cut from a tube of shape memory metal. Neck region 104 and second flared end region 106 may be covered with biocompatible material 120, e.g., in the region extending approximately from sinusoidal ring 113 to sinusoidal ring 116.

Duckbill tissue valve 830 is coupled to stent 110 in first flared end region 102. Preferably, tissue valve 830 opens at a pressure of less than 1 mmHg, closes at a pressure gradient of 0 mmHg, and remains closed at relatively high back pressures, for example at back pressures of at least 40 mmHg. Like tissue valve 130, tissue valve 830 may be formed using any natural or synthetic biocompatible material, including but not limited to pericardial tissue, e.g., thinned and fixed bovine, equine, or porcine pericardial tissue. As shown in FIG. 8B, the outlet of duckbill tissue valve 830 is coupled, e.g., sutured, to first and second longitudinally extending struts 111', 111" in the region extending between first (uppermost) sinusoidal ring 112 and second sinusoidal ring 113. Referring again to FIG. 8A, the inlet to tissue valve 830 also is coupled, e.g., sutured, to the upper edge of the biocompatible material 120 along line 121, at or near sinusoidal ring 113, so as to provide a smooth profile.

FIGS. 8A and 8B illustrate device 800 when duckbill tissue valve 830 is in an open configuration, in which leaflets 931 are in an open position to permit flow. FIG. 8C illustrates device 800 when tissue valve 830 is in a closed configuration, in which leaflets 831 are in a closed position to inhibit flow, in which position they preferably form a substantially straight line. Device 800 preferably is configured so as to provide flow characteristics similar to those described above for device 100.

Referring now to FIG. 9, alternative device of the present invention is described. Device 900 has first and second flared end regions 902, 906, with neck region 904 disposed therebetween. Device 900 includes hourglass-shaped stent 910, biocompatible material 920, and tissue valve 930 and further comprises three general regions as described for the foregoing embodiments: first flared or funnel-shaped end region 902 configured to flank the right side of the atrial septum, second flared or funnel-shaped end region 906 configured to flank the left side of the atrial septum, and neck region 904 disposed between the first and second flared end regions and configured to lodge in a puncture formed in the atrial septum, preferably in the fossa ovalis. Like the devices described above, stent 910 includes plurality of sinusoidal rings 912 interconnected by longitudinally extending struts 911, which may be laser cut from a tube of shape memory metal. However, as compared to devices 100 and 800 described further above, sinusoidal rings 912 do not extend into first flared end region 902. Instead, the outlet end of tissue valve 930 is coupled to longitudinally extending struts 911' and 911". Neck region 904 and second flared end region 906 may be covered with biocompatible material 920.

Duckbill tissue valve 930 is coupled to stent 910 in first flared end region 902. Specifically, the outlet of tissue valve 930 is coupled, e.g., sutured, to first and second longitudinally extending struts 911', 911" in the region extending between the first (uppermost) sinusoidal ring 912 and the distal ends of struts 911', 911". The inlet end of tissue valve 930 also is coupled, e.g., sutured, to the upper edge of biocompatible material 920 at or near first (uppermost) sinusoidal ring 912, so as to provide a smooth profile. Device 900 is preferably configured so as to provide flow characteristics similar to those described above for device 100.

EXAMPLE

An exemplary device 800 such as described above with respect to FIGS. 8A-8C was implanted into four sheep with induced chronic heart failure (V1-V4), while four sheep with induced chronic heart failure did not receive the device, and were used as a control (C1-C4). An additional control animal was subjected to only a partial heart failure protocol, and did not receive the device (S1).

Chronic heart failure was induced in animals C1-C4 and V1-V4, who were less than 1 year of age and weighed between 70 and 120 pounds, by first anesthetizing the animals via a venous catheter positioned in a peripheral vessel, i.e., the ear. The animals were given an opiate or synthetic opiate (e.g., morphine or butorphanol) intravenously at 0.25 to 0.5 mg/kg, as well as telazol at 0.3 mg/kg, through the venous catheter, and anesthetized by intravenous etomidate. Anesthesia was maintained with 1.5% isoflurane delivered in 100% $O_2$, via a tracheal tube. The animals were placed on a fluoroscope table in left lateral recumbence, and a gastric tube (about 7 F) was inserted into the rumen to serve as a vent.

An introducer was then positioned within the carotid artery via cut down and modified Seldinger technique. A 6 F or 7 F Judkins left 4.5 catheter was advanced through the introducer into the left circumflex coronary artery (LCxA) under fluoroscopic guidance, and about 60,000 polystyrene microspheres of about 90 μm diameter were injected into the LCxA to induce embolization to induce myocardial infarction followed by chronic heart failure. The arterial and skin incisions then were closed, and the animals were administered about 500 mg of cephalexein p.o. bid for two days, as well as a synthetic opiate prn, specifically buprenorphine administered intramuscularly at about 0.03 to 0.05 mg/kg, once during recovery and following the anesthesia. Animals observed to have arrhythmia following or during the microsphere injection were also administered lidocaine following embolization, at about 2 to 4 mg/kg via intravenous bolus, followed by constant infusion at about 20 to 80 μf/kf/minute.

This procedure was repeated one week following the first procedure in animals V1-V4 and C1-C4. This model of induced chronic heart failure has about a 100% fatality rate at 12 weeks, and as discussed below each of the control animals died before the end of the 12 week study. The procedure was performed a single time in animal S1, and as discussed below this animal survived the 12 week study but deteriorated over the course of the study.

Device 800 was implanted into four animals V1-V4. Fluid filled catheters were implanted into animals V1-V4 and C1-C4, approximately seven days after the second embolization procedure. Fluid filled catheters were not implanted into animal S1. The implanted device 800 had an overall length of 15 mm (7 mm on the left atrial side and 8 mm on the right atrial side), a diameter on the left atrial side of 14 mm, a diameter on the right atrial side of 13 mm, an inside neck diameter of 5.3 mm, and an angle between the left and right atrial sides of the device of 70 degrees. The fluid filled catheters were implanted in the inferior vena cava (IVC), superior vena cava (SVC), pulmonary artery, and left atrium through a right mini-thoracotomy under anesthesia, and were configured to measure oxygen saturations and pressures in the IVC, pulmonary artery, right atrium, and left atrium. After implantation and throughout the study, the animals were each treated daily with aspirin, plavix, and clopidogrel. Their heart rate was periodically monitored.

Two-dimensional M-mode echocardiograms of the left ventricle were periodically obtained to document the ejection fraction (EF), as well as the shortening fraction, calculated as 100(EDD−ESD)/EDD, where EDD is the end-diastolic dimension (diameter across ventricle at the end of diastole) and ESD is the end-systolic dimension (diameter across ventricle at the end of systole). Echocardiographic studies of the animals were performed while they were either conscious or under light chemical restraint with butorphanol, and manually restrained in the right or left decubitis position, using an ultrasound system with a 3.5 to 5.0 mHz transducer (Megas ES, model 7038 echocardiography unit). The echocardiograms were recorded for subsequent analysis. The left ventricle fractional area shortening (FAS), a measure of left ventricle systolic function, was measured from the short axis view at the level of the papillary muscles. Measurements of left ventricle dimensions, thickness of the posterior wall, and intraventricular septum were obtained and used as an index of left ventricle remodeling. The major and minor axes of the left ventricle were measured and used to estimate left ventricle end-diastolic circumferential wall stress.

The clinical conditions of the animals were evaluated by comparing various parameters over a twelve-week period, including left atrial pressure, right atrial pressure, pulmonary artery pressure, and ejection fraction (EF). Parameters such as left and right atrial pressures, left and right ventricular dimensions, and left and right ventricular function were obtained based on the collected data. Data obtained during the study are discussed further below with respect to FIGS. 10A-10D and Tables 2-15.

During the course of the study, all four of the control animals C1-C4 were observed to suffer from high pulmonary artery pressure, high right atrial pressure, and low ejection fraction, and were immobile. All four control animals died during the trial, C3 at week 1, C4 at week 3, C1 at week 6, and C2 at week 9. Animal S1 survived but deteriorated over the course of the study.

By comparison, all of the animals V1-V4 into which the device had been implanted were observed to have dramatically improved hemodynamic conditions over the course of the study, and appeared healthy and energetic without signs of congestion by the end of the study. As discussed below with reference to FIGS. 10A-10D, device 800 was observed to reduce left atrial pressure in the implanted animals by about 5 mmHg, with an increase in cardiac output, and preservation of right atrial pressure and pulmonary artery pressure. Left ventricle parameters were observed to be substantially improved in the implanted animals as compared to the control animals, and right ventricle and pulmonary artery pressure were also observed to be normal in the implanted animals.

Three of the four implanted animals, V1, V3, and V4 survived the twelve week study. One of the implanted animals, V2, died at week 10 of a non-heart failure cause. Specifically, arrhythmia was diagnosed as the cause of death; the animal was observed to have arrhythmia at baseline, and had been defibrillated before implantation Throughout the study, this animal was observed to have good hemodynamic data. At the end of the study, the surviving implant animals were observed to respond normally to doses of dobutamine, indicating significant improvement in the condition of their heart failure.

Figure 10A:
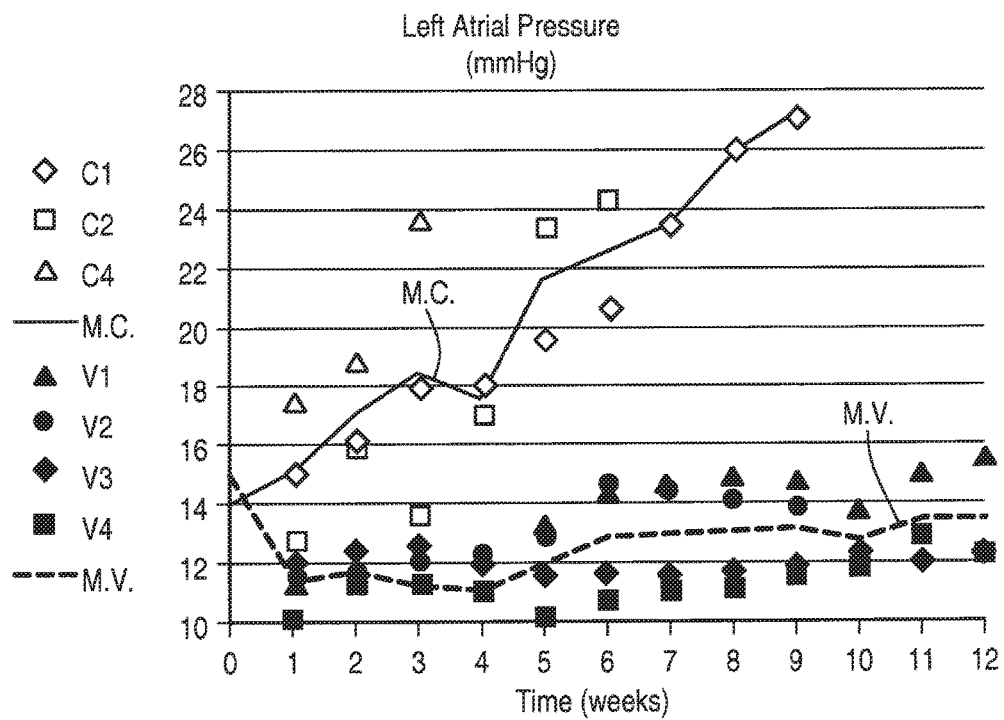

FIG. 10A is a plot of the measured left atrial pressure of the control animals (C1-C4), and of the implanted animals (V1-V4), along with mean values for each (M.C. and M.V., respectively). Data for control animal C3 is not shown, as the animal died in the first week of the study. The mean left atrial pressure for the control animals (M.C.) was observed to steadily increase over the course of the study, from about 14 mmHg at baseline to over 27 mmHg when the last control animal (C1) died. By comparison, the mean left atrial pressure for the implanted animals (M.V.) was observed to drop from about 15 mmHg at baseline to less than 12 mmHg at week one, and to remain below 14 mmHg throughout the study.

Figure 10B:
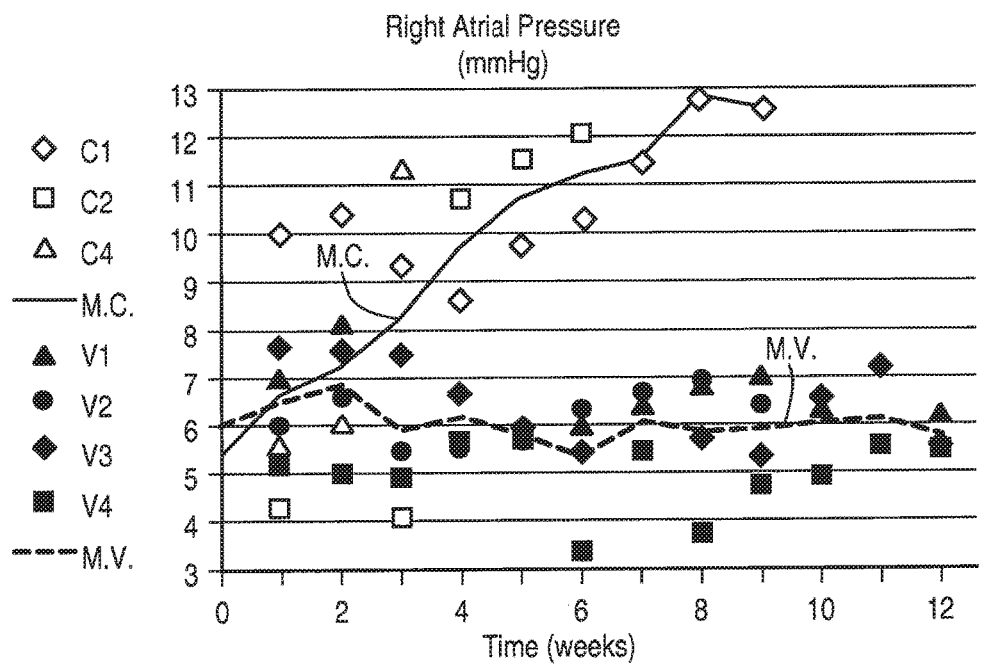

FIG. 10B is a plot of the measured right atrial pressure of the control animals (C1-C4), and of the implanted animals (V1-V4), along with mean values for each (M.C. and M.V., respectively). Data for control animal C3 is not shown. As for the left atrial pressure, the mean right atrial pressure for the control animals (M.C.) was observed to steadily increase over the course of the study, from about 5.5 mmHg at baseline to over 12 mmHg when the last control animal (C1) died. By comparison, the mean right atrial pressure for the implanted animals (M.V.) was observed to remain relatively steady throughout the study, increasing from about 6 mmHg to about 7 mm Hg over the first two weeks of the study, and then decreasing again to about 6 mmHg for the rest of the study.

Figure 10C:
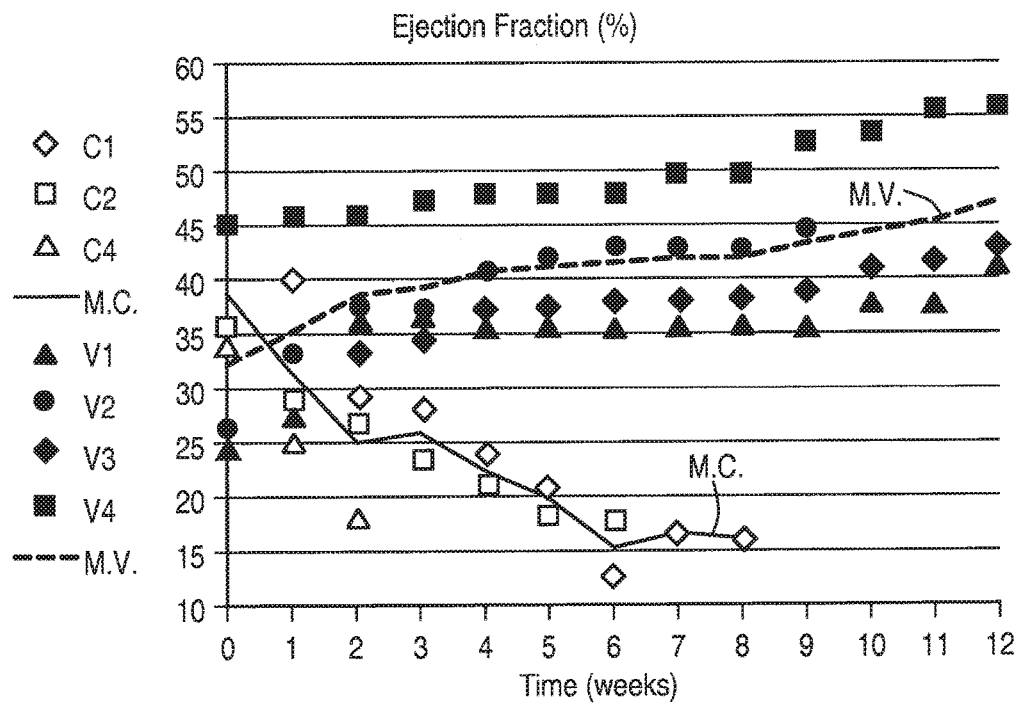

FIG. 10C is a plot of the measured ejection fraction of the control animals (C1-C4), and of the implanted animals (V1-V4), along with mean values for each (M.C. and M.V., respectively). Data for control animal C3 is not shown. The mean ejection fraction for the control animals (M.C.) was observed to steadily decrease over the course of the study, from about 38% at baseline to about 16% when the last control animal (C1) died. By comparison, the mean ejection fraction for the implanted animals (M.V.) was observed to steadily increase over the course of the study, from about 33% at baseline to about 46% at the conclusion of the study.

Figure 10D:
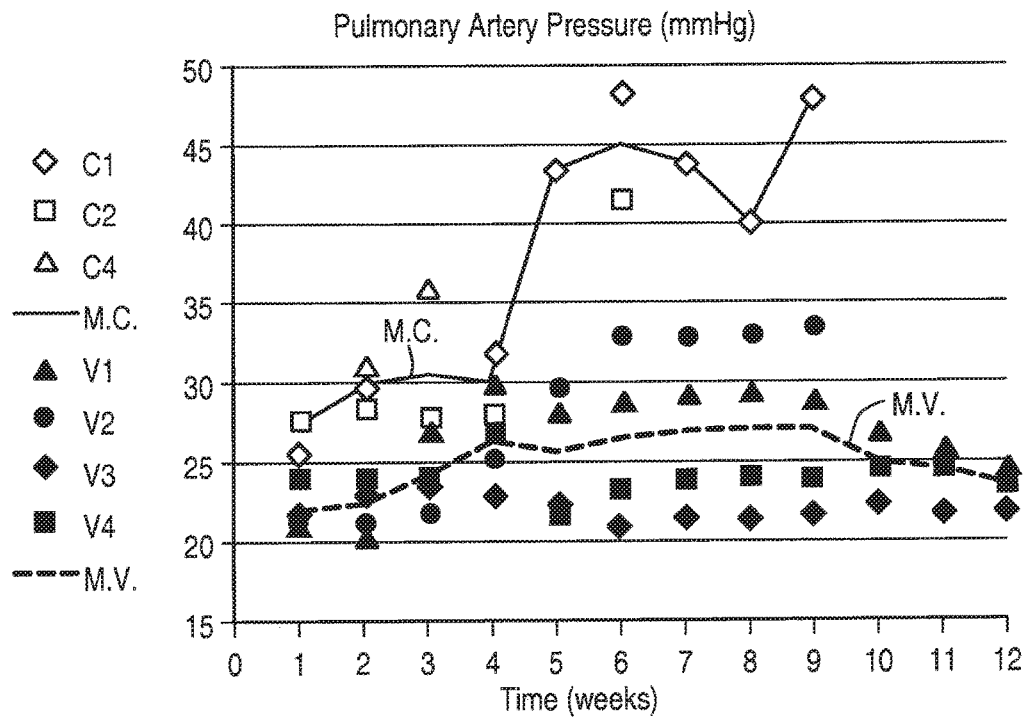

FIG. 10D is a plot of the measured pulmonary artery pressure of the control animals (C1-C4), and of the implanted animals (V1-V4), along with mean values for each (M.C. and M.V., respectively). Data for control animal C3 is not shown. The mean pulmonary artery pressure for the control animals (M.C.) was observed to vary significantly over the course of the study, from about 27 mmHg during the first week of the study, to about 45 mmHg at week six, then down to 40 mmHg at week eight, and then up to about 47 mmHg at week nine, when the last control animal (C1) died. By comparison, the mean pulmonary artery pressure for the implanted animals (M.V.) was observed to remain relatively steady, increasing from about 22 mmHg during week one, to about 27 mmHg during weeks four through nine, and then back down to about 24 mmHg by week twelve, at the conclusion of the study.

Upon explantation at the end of the study, three of the four implanted devices were observed to be completely patent and functional. For example, FIGS. 11A-11B are photographic images of device 800 upon explantation from one of the implanted animals, taken from the left atrial and right atrial sides respectively. A fourth device was observed to be patent up until week 11, using Fick's measurements and echocardiography. At histopathology, no inflammation was observed around the valves, and a thin endothelial layer was observed to have ingrown. For example, FIG. 11C is a microscope image of device 800 upon explantation from one of the implanted animals, showing approximately 0.2 mm of endothelial tissue in the device in the neck region.

Tables 2 through 15 present raw data obtained from the control animals C1-C4 and S1 and the implanted animals V1-V4, while awake, over the course of the 12 week study, including baseline immediately before implantation (Day 0, during which the animals were sedated). The mean values for control animals C1-C4 and S1 (M.C.) and the mean values for the implanted animals V1-V4 (M.V.), with standard deviations, are also presented in the tables. Missing data indicates either the death of the animal or omission to obtain data. Data for animal C3 is not shown because the animal died in the first week of the study. Data was not collected for any animal in week 7 of the study. As noted above, animal S1 was not implanted with pressure and saturation flow monitors, so no data is shown for that animal for certain measurements.

Table 2 presents the study's results pertaining to right atrial pressure (RAP, mmHg). As can be seen from Table 2, the average RAP for the control animals (C1-C4) increased significantly over the course of the study. For example, animal C1 experienced an RAP increase to about 330% of baseline before death, C2 to about 110% of baseline before death, and C4 to about 340% of baseline before death. The increase was relatively steady during this period. By contrast, the RAP for the implanted animals (V1-V4) started at a similar value to that of the control animals, at an average of 6±2 mmHg at baseline, but did not significantly vary over the course of the study. Instead, the average RAP of the implanted animals remained within about 1-2 mmHg of the baseline value for the entire study (between a high of 7±1 and a low of 5±1). Thus, the inventive device may inhibit increases in the right atrial pressure in subjects suffering from heart failure, and indeed may maintain the right atrial pressure at or near a baseline value. This is particularly noteworthy because, as described elsewhere herein, the device may offload a relatively large volume of blood from the left atrium to the right atrium; however the relatively high compliance of the right atrium inhibits such offloading from significantly increasing RAP.

TABLE 2

Right Atrial Pressure (RAP, mmHg)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 3.8   | 4.3   | 5.1   | 4.1   | 10.8  | 11.6  | 12.1  | 12.8  | 12.6  |        |        |        |
| C2   | 9.2   | 10.1  | 10.5  | 9.8   | 8.6   | 9.8   | 10.3  |       |       |        |        |        |
| C4   | 3.3   | 5.7   | 6.1   | 11.4  |       |       |       |       |       |        |        |        |
| S1   |       |       |       |       |       |       |       |       |       |        |        |        |
| V1   | 8.9   | 7.1   | 8.2   | 5.6   | 6.8   | 5.7   | 6.1   | 6.9   | 7.1   | 6.5    | 5.7    | 6.3    |
| V2   | 7.4   | 6.1   | 6.7   | 5.5   | 5.6   | 6.0   | 6.4   | 7.0   | 6.5   |        |        |        |
| V3   | 8.0   | 7.7   | 7.7   | 7.6   | 6.7   | 6.0   | 5.5   | 5.8   | 5.4   | 6.7    | 7.2    | 5.7    |
| V4   | 0.9   | 5.2   | 5.1   | 4.9   | 5.7   | 5.8   | 3.4   | 3.8   | 4.8   | 5.0    | 5.6    | 5.7    |
| M.C. | 5 ± 2 | 7 ± 2 | 7 ± 1 | 8 ± 2 | 10 ± 1| 11 ± 1| 11 ± 1| 13    | 13    |        |        |        |
| M.V. | 6 ± 2 | 7 ± 1 | 7 ± 1 | 6 ± 1 | 6 ± 0 | 6 ± 0 | 5 ± 1 | 6 ± 1 | 6 ± 1 | 6 ± 1  | 6 ± 1  | 6 ± 0  |

Table 3 presents the study's results pertaining to left atrial pressure (LAP, mmHg). As can be seen from Table 3, the average LAP of the control animals started at a similar value at baseline as that of the implanted animals, 14±1 mmHg for the former and 15±2 mmHg for the latter. However, the LAP of the control animals increased significantly over the course of the study. For example, animal C1 had a baseline LAP of 10.6 mmHg, and an LAP of 27.3 mmHg at week 9 just before death, about 250% of baseline. The LAP increases of the other control animals were smaller, but still significantly larger than that of the implanted animals. Indeed, in each case the LAP of the implanted animals actually decreased immediately following implantation. For example, the LAP for animal V1 decreased from 15.7 mmHg at baseline to 11.4 mmHg one week following implantation, about 73% of baseline. The average LAP for the implanted animals decreased from 15±2 at baseline to a low of 11±0 at week one, and then gradually increased to about 13±1 at week six (about 87% of baseline), where it remained for the remainder of the study.

TABLE 3

Left Atrial Pressure (LAP, mmHg)

|      | Day 0  | Wk. 1  | Wk. 2  | Wk. 3  | Wk. 4  | Wk. 5  | Wk. 6  | Wk. 8  | Wk. 9  | Wk. 10 | Wk. 11 | Wk. 12 |
|------|--------|--------|--------|--------|--------|--------|--------|--------|--------|--------|--------|--------|
| C1   | 10.6   | 12.8   | 15.9   | 13.6   | 17.0   | 23.5   | 24.4   | 26.0   | 27.3   |        |        |        |
| C2   | 14.4   | 15.1   | 16.3   | 18.1   | 18.1   | 19.7   | 20.7   |        |        |        |        |        |
| C4   | 16.4   | 17.7   | 18.9   | 23.7   |        |        |        |        |        |        |        |        |
| S1   |        |        |        |        |        |        |        |        |        |        |        |        |
| V1   | 15.7   | 11.4   | 11.3   | 8.8    | 9.2    | 13.4   | 14.3   | 15.0   | 14.9   | 13.9   | 15.2   | 15.6   |
| V2   | 19.8   | 11.7   | 11.7   | 12.1   | 12.3   | 13.0   | 14.7   | 14.2   | 14.0   |        |        |        |
| V3   | 14.3   | 12.1   | 12.4   | 12.7   | 12.0   | 11.5   | 11.6   | 11.8   | 11.9   | 12.4   | 13.0   | 12.3   |
| V4   | 10.3   | 10.1   | 11.3   | 11.4   | 11.0   | 10.2   | 10.8   | 11.2   | 11.7   | 11.9   | 12.2   | 12.1   |
| M.C. | 14 ± 1 | 15 ± 1 | 17 ± 1 | 18 ± 3 | 18 ± 0 | 22 ± 2 | 23 ± 2 | 26     | 27     |        |        |        |
| M.V. | 15 ± 2 | 11 ± 0 | 12 ± 0 | 11 ± 1 | 11 ± 1 | 12 ± 1 | 13 ± 1 | 13 ± 1 | 13 ± 1 | 13 ± 1 | 13 ± 1 | 13 ± 1 |

Table 4 further elaborates the results presented in Table 3, and presents the calculated change in LAP (ΔLAP, %). As can be seen in Table 4, control animals C2 and C4 each died after their LAP increased by about 44%, while control animal C1 died after its LAP increased by about 158%. By comparison, implanted animals V1, V2, and V3 each experienced significant decreases in LAP immediately following implantation, e.g., by about −27%, −41%, and −15% relative to baseline. The LAP for animal V4 remained near baseline following implantation. The LAP for animal V1 slowly increased back to baseline over the course of the study; the LAP for animal V2 remained significantly below baseline before its death but increased somewhat; the LAP for animal V3 also remained below baseline throughout the study but increased somewhat; and the LAP for animal V4 fluctuated somewhat above baseline but remained within about 18% of baseline. Thus, it can be seen that the inventive device may inhibit increases in the left atrial pressure in patients suffering from heart failure. Indeed, the device may actually decrease the left atrial pressure below baseline in patients suffering from heart failure for a time period immediately following implantation, in some embodiments to a level about 20% below baseline. The left atrial pressure subsequently may gradually increase back towards a baseline level over a time period of weeks or months, as the heart remodels and improves in efficiency. It is important to note that the control animals died from pulmonary edema, which correlates with LAPs that exceed the "danger zone" of 25 mmHg or more at which edema occurs.

TABLE 4

Change in Left Atrial Pressure (ΔLAP, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   |       | +5    | +51   | +29   | +61   | +122  | +131  | +145  | +158  |        |        |        |
| C2   |       | +21   | +14   | +26   | +26   | +37   | +44   |       |       |        |        |        |
| C4   |       | +8    | +15   | +44   |       |       |       |       |       |        |        |        |
| S1   |       |       |       |       |       |       |       |       |       |        |        |        |
| V1   |       | −27   | −28   | −44   | −41   | −15   | −9    | −4    | −5    | −11    | −3     | 0      |
| V2   |       | −41   | −41   | −39   | −38   | −34   | −26   | −28   | −29   |        |        |        |
| V3   |       | −15   | −13   | −11   | −16   | −20   | −19   | −17   | −16   | −13    | −9     | −13    |
| V4   |       | −2    | +10   | +10   | +7    | −1    | +5    | +8    | +13   | +16    | +18    | +17    |
| M.C. |       | +11 ± 4 | +27 ± 10 | +33 ± 5 | +44 ± 14 | +80 ± 42 | +87 ± 35 | +145 | +158 |  |  |  |
| M.V. |       | −21 ± 8 | −18 ± 11 | −21 ± 13 | −22 ± 11 | −17 ± 7 | −12 ± 7 | −10 ± 8 | −9 ± 9 | −3 ± 9 | +2 ± 8 | +1 ± 9 |

Table 5 presents the study's results pertaining to pulmonary artery pressure (PAP, mmHg). As can be seen in Table 5, the control animals experienced significant increases in PAP before death, e.g., about 230% of baseline for animal C1, 217% of baseline for animal C2, and 180% of baseline for animal C4. The PAP for the implanted animals also increased over the course of the study, but in most cases by significantly less than that of the control animals, e.g., to about 133% of baseline for animal V1, about 161% of baseline for animal V2, about 156% of baseline for animal V3, and about 169% for animal V4. The inventive device thus may inhibit increases in pulmonary artery pressure in subjects suffering from heart failure, relative to what they may otherwise have experienced during heart failure.

TABLE 5

Pulmonary Artery Pressure (PAP, mmHg)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 20.8  | 27.9  | 28.5  | 27.9  | 28.0  |       | 41.7  | 40.2  | 48.0  |        |        |        |
| C2   | 22.3  | 25.8  | 29.7  | 26.9  | 32.0  | 43.5  | 48.4  |       |       |        |        |        |
| C4   | 20.1  | 28.4  | 31.2  | 36.1  |       |       |       |       |       |        |        |        |
| S1   |       |       |       |       |       |       |       |       |       |        |        |        |
| V1   | 18.6  | 21.2  | 20.7  | 27.1  | 30.2  | 28.4  | 29.0  | 29.8  | 29.2  | 27.1   | 26.3   | 24.8   |
| V2   | 20.9  | 21.5  | 21.4  | 21.9  | 25.4  | 29.7  | 33.0  | 33.0  | 33.6  |        |        |        |
| V3   | 14.1  | 22.0  | 23.3  | 23.5  | 23.1  | 22.6  | 21.0  | 21.6  | 21.8  | 22.6   | 22.0   | 22.0   |
| V4   | 14.0  | 24.1  | 24.2  | 24.1  | 26.8  | 22.0  | 23.4  | 24.3  | 24.2  | 24.7   | 25.0   | 23.6   |
| M.C. | 21 ± 1 | 27 ± 1 | 30 ± 1 | 30 ± 3 | 30 ± 2 | 43 | 45 ± 3 | 40 | 48 |  |  |  |
| M.V. | 17 ± 2 | 22 ± 1 | 22 ± 1 | 24 ± 1 | 26 ± 1 | 26 ± 2 | 27 ± 3 | 27 ± 3 | 27 ± 3 | 25 ± 1 | 24 ± 1 | 23 ± 1 |

Table 6 presents the study's results pertaining to heart rates (HR, beats per minute). During each week of the study, except for week one, it can be seen that the heart rates of the control animals (C1-C4 and S1) were higher than those of the implanted animals. Thus the inventive device may reduce heart rate in subjects suffering from heart failure. Put another way, the inventive device provides may enhance the efficiency of the pulmonary system and therefore reduce the frequency with which the heart must beat to satisfy the body's oxygen demands.

TABLE 6

Heart Rate (HR, beats per minute)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   |       | 131   | 147   | 127   | 127   | 117   | 123   | 127   | 143   |        |        |        |
| C2   |       | 146   | 192   | 165   | 138   | 156   | 149   |       |       |        |        |        |
| C4   |       | 135   |       |       |       |       |       |       |       |        |        |        |
| S1   |       | 143   | 131   | 124   | 123   | 125   | 125   | 130   | 133   | 131    |        |        |
| V1   |       | 121   | 149   | 151   | 110   | 132   | 137   | 94    | 106   | 91     |        |        |
| V2   |       | 142   | 132   | 120   | 140   | 137   | 144   | 126   | 135   |        |        |        |
| V3   |       | 151   | 107   | 74    | 82    | 111   | 98    | 95    | 107   | 112    | 105    | 96     |
| V4   |       | 187   | 159   | 118   | 130   | 139   | 101   | 72    | 112   | 122    | 102    |        |
| M.C. |       | 139 ± 3 | 157 ± 18 | 139 ± 13 | 129 ± 5 | 136 ± 20 | 133 ± 8 | 126 ± 1 | 136 ± 6 | 133 | 131 |  |
| M.V. |       | 150 ± 4 | 137 ± 1 | 116 ± 16 | 115 ± 3 | 130 ± 6 | 120 ± 12 | 97 ± 11 | 115 ± 7 | 108 ± 9 | 105 | 99 ± 2 |

Table 7 presents the study's results relating to oxygen saturation in the vena cava ($VC\_SO_2$, %). The control animals and the implanted animals had similar $VC\_SO_2$ levels throughout the course of the study, although for both groups the levels were lower than at baseline. It is expected that oxygen saturation in the vena cava is relatively low, because the vessel carries deoxygenated blood from the body to the heart.

TABLE 7

Oxygen Saturation in Vena Cava ($VC\_SO_2$, %)

| | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 90 | 85 | 84 | 85 | 80 | 83 | 80 | 80 | 79 | | | |
| C2 | | 80 | 81 | 75 | 77 | 75 | 78 | | | | | |
| C4 | | 82 | 77 | 62 | | | | | | | | |
| S1 | | | | | | | | | | | | |
| V1 | 94 | 80 | 80 | 81 | 79 | 80 | 68 | 80 | 80 | 80 | 79 | 80 |
| V2 | 98 | 78 | 78 | 70 | 81 | 78 | 73 | 79 | 79 | | | |
| V3 | | 75 | 74 | 75 | 74 | 71 | 75 | 74 | 79 | 67 | 74 | 78 |
| V4 | | 73 | 73 | 72 | 67 | 76 | 71 | 76 | 79 | 73 | 74 | 75 |
| M.C. | 90 | 82 ± 1 | 81 ± 2 | 74 ± 6 | 79 ± 1 | 79 ± 4 | 79 ± 1 | 80 | 79 | | | |
| M.V. | 96 ± 1 | 76 ± 2 | 76 ± 2 | 75 ± 2 | 75 ± 3 | 76 ± 2 | 72 ± 1 | 77 ± 2 | 79 ± 0 | 73 ± 4 | 76 ± 2 | 78 ± 1 |

Table 8 presents the study's results relating to oxygen saturation in the pulmonary artery ($PA\_SO_2$, %). The $PA\_SO_2$ values for the implanted animals are somewhat higher than those for the control animals (e.g., between about 5-10% higher), indicating that device 100 was patent and transferring blood from the left atrium to the right atrium. It is expected that oxygen saturation in the pulmonary artery is relatively low, because the vessel carries deoxygenated blood from the heart to the lungs.

TABLE 8

Oxygen Saturation in Pulmonary Artery ($PA\_SO_2$, %)

| | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 84 | 81 | 76 | 78 | 71 | | 76 | 75 | 73 | | | |
| C2 | | 64 | 77 | 67 | 70 | 69 | 70 | | | | | |
| C4 | | 78 | 76 | 57 | | | | | | | | |
| S1 | | | | | | | | | | | | |
| V1 | 91 | 81 | 83 | 82 | 81 | 85 | 82 | 83 | 84 | 83 | 80 | 80 |
| V2 | 92 | 81 | 80 | 84 | 87 | 87 | 80 | 82 | 84 | | | |
| V3 | | 77 | 79 | 84 | 79 | 76 | 80 | 78 | 85 | 71 | 77 | 81 |
| V4 | | 76 | 80 | 84 | 75 | 78 | 76 | 83 | 83 | 78 | 77 | 77 |
| M.C. | 84 | 74 ± 5 | 76 ± 0 | 67 ± 5 | 71 ± 0 | 69 | 73 ± 2 | 75 | 73 | | | |
| M.V. | 92 ± 0 | 79 ± 1 | 81 ± 1 | 84 ± 1 | 81 ± 3 | 82 ± 3 | 80 ± 1 | 81 ± 1 | 84 ± 0 | 77 ± 3 | 78 ± 1 | 79 ± 1 |

Table 9 presents the oxygen saturation in the left atrium ($LA\_SO_2$, %). The $LA\_SO_2$ values for the implanted animals are similar to those for the control animals. Animals with $LA\_SO_2$ values of less than 94% are considered to have low cardiac output.

TABLE 9

Oxygen Saturation in Left Atrium ($LA\_SO_2$, %)

| | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|---|---|---|---|---|---|---|---|---|---|---|---|---|
| C1 | 100 | 96 | 97 | 94 | 93 | 95 | 92 | 96 | 93 | | | |
| C2 | | 96 | 97 | 98 | 99 | 96 | 95 | | | | | |
| C4 | | 95 | 95 | 98 | | | | | | | | |
| S1 | | | | | | | | | | | | |
| V1 | 100 | 93 | 96 | 97 | 94 | 96 | 97 | 97 | 97 | 97 | 96 | 96 |
| V2 | 100 | 97 | 97 | 96 | 92 | 96 | 87 | 95 | 97 | | | |
| V3 | | 96 | 93 | 97 | 96 | 93 | 97 | 96 | 96 | 94 | 96 | 96 |
| V4 | | 95 | 96 | 96 | 97 | 97 | 97 | 99 | 98 | 97 | 98 | 98 |

TABLE 9-continued

Oxygen Saturation in Left Atrium (LA_SO$_2$, %)

|      | Day 0   | Wk. 1  | Wk. 2  | Wk. 3  | Wk. 4  | Wk. 5  | Wk. 6  | Wk. 8  | Wk. 9  | Wk. 10 | Wk. 11 | Wk. 12 |
|------|---------|--------|--------|--------|--------|--------|--------|--------|--------|--------|--------|--------|
| M.C. | 100     | 96 ± 0 | 96 ± 1 | 97 ± 1 | 96 ± 2 | 96 ± 1 | 94 ± 1 | 96     | 93     |        |        |        |
| M.V. | 100 ± 0 | 95 ± 1 | 96 ± 1 | 97 ± 0 | 95 ± 1 | 96 ± 1 | 95 ± 3 | 97 ± 1 | 97 ± 0 | 96 ± 1 | 97 ± 1 | 97 ± 1 |

Table 10 presents the study's results pertaining to the left ventricle internal diameter in diastole (LVIDd, cm), which also may be referred to in the art as left ventricular end-diastolic dimension (LVEDD or LVDD). It may be seen that the LVIDd for the control (C1-C4 and S1) and implanted (V1-V4) animals were relatively similar, and does not significantly vary during weeks 1-12 of the study. This may be attributed to the relatively low pressures during implantation. It may be expected that when the device 100 is implanted in a subject with high LAP, the LVIDd will decrease after implantation as a result of the significant reduction in LAP.

TABLE 10

Left Ventricle Internal Diameter in Diastole (LVIDd, cm)

|      | Day 0   | Wk. 1   | Wk. 2   | Wk. 3   | Wk. 4   | Wk. 5   | Wk. 6   | Wk. 8   | Wk. 9   | Wk. 10  | Wk. 11  | Wk. 12  |
|------|---------|---------|---------|---------|---------|---------|---------|---------|---------|---------|---------|---------|
| C1   | 4.6     | 5.4     | 5.0     | 5.1     | 5.4     | 5.3     | 4.8     | 4.8     | 4.8     |         |         |         |
| C2   | 4.0     | 4.1     | 4.4     | 4.4     | 4.0     | 4.0     | 3.8     |         |         |         |         |         |
| C4   | 4.2     | 5.7     | 5.7     | 5.5     |         |         |         |         |         |         |         |         |
| S1   | 4.3     | 4.7     | 4.9     | 5.0     | 4.7     |         | 5.0     | 5.0     | 5.0     |         | 4.4     | 5.0     |
| V1   | 3.8     | 4.1     | 4.2     | 4.3     | 3.8     | 4.0     | 4.1     | 4.5     | 4.3     | 4.4     | 4.3     | 4.0     |
| V2   | 5.3     | 4.5     | 4.5     | 5.4     | 5.0     | 4.9     | 5.0     | 4.9     | 5.0     |         |         |         |
| V3   | 5.4     | 6.3     | 6.2     | 5.9     | 6.0     | 5.6     | 5.5     | 6.0     | 6.2     | 6.3     | 5.9     | 5.6     |
| V4   | 4.4     | 4.9     | 4.7     | 4.3     | 4.0     | 3.9     | 4.1     | 4.1     | 4.1     | 4.2     | 4.4     | 4.1     |
| M.C. | 4.3 ± .1 | 5.0 ± .4 | 5.0 ± .3 | 5.0 ± .2 | 4.7 ± .4 | 4.7 ± .7 | 4.5 ± .4 | 4.9 ± .1 | 4.9 ± .1 |         | 4.4     | 5.0     |
| M.V. | 4.7 ± .4 | 5.0 ± .5 | 4.9 ± .4 | 5.0 ± .4 | 4.7 ± .5 | 4.6 ± .4 | 4.7 ± .3 | 4.9 ± .4 | 4.9 ± .5 | 5.0 ± .7 | 4.9 ± .5 | 4.6 ± .5 |

Table 11 presents the study's results pertaining to the left ventricle internal diameter in systole (LVIDs, cm), which also may be referred to in the art as left ventricular end-systolic dimension (LVESD or LVSD). While the LVIDd discussed above with respect to Table 10 was similar for both groups of animals, it may be seen here that for the control animals, the LVIDs increased from baseline in week one (e.g., from an average 3.5±0.2 at baseline to 4.2±0.3 at week one), and then increased further and/or remained elevate. By comparison, the LVIDs for the implanted animals increased slightly from baseline in week one (e.g., from an average 4.0±0.2 at baseline to 4.2±0.4 at week one), but then decreased relatively steadily over the course of the study (e.g., to 3.5±0.4 at week twelve). This decrease reflects the remodeling of the left ventricle over time that results from offloading blood flow from the left atrium back to the right atrium through the inventive device.

TABLE 11

Left Ventricle Internal Diameter in Systole (LVIDs, cm)

|    | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|----|-------|-------|-------|-------|-------|-------|-------|-------|-------|--------|--------|--------|
| C1 | 3.8   | 4.7   | 4.4   | 4.5   | 4.9   | 4.9   | 4.4   | 4.4   | 4.4   |        |        |        |
| C2 | 3.0   | 3.3   | 3.8   | 3.8   | 3.5   | 3.7   | 3.6   |       |       |        |        |        |
| C4 | 3.5   | 4.8   | 5.0   | 5.1   |       |       |       |       |       |        |        |        |
| S1 | 3.6   | 4.1   | 4.3   | 4.4   | 4.2   |       | 4.5   | 4.6   | 4.6   |        | 4.7    | 4.7    |
| V1 | 3.6   | 3.5   | 3.5   | 3.6   | 3.2   | 3.3   | 3.4   | 3.7   | 3.6   | 3.6    | 3.5    | 3.2    |
| V2 | 4.7   | 3.8   | 3.7   | 3.8   | 4.0   | 3.9   | 3.9   | 3.9   | 4.0   |        |        |        |
| V3 | 4.6   | 5.3   | 5.2   | 4.9   | 4.9   | 4.6   | 4.5   | 4.9   | 5.0   | 5.0    | 4.7    | 4.4    |
| V4 | 3.4   | 4.0   | 3.7   | 3.3   | 3.1   | 2.9   | 3.1   | 3.1   | 3.0   | 3.1    | 3.2    | 2.9    |

TABLE 11-continued

Left Ventricle Internal Diameter in Systole (LVIDs, cm)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| M.C. | 3.5 ± .2 | 4.2 ± .3 | 4.3 ± .3 | 4.5 ± .3 | 4.2 ± .4 | 4.3 ± .6 | 4.2 ± .3 | 4.5 ± .1 | 4.5 ± .1 |  | 4.7 | 4.7 |
| M.V. | 4.0 ± .3 | 4.2 ± .4 | 4.0 ± .4 | 3.9 ± .4 | 3.8 ± .4 | 3.7 ± .4 | 3.7 ± .3 | 3.9 ± .4 | 3.9 ± .4 | 3.9 ± .6 | 3.8 ± .5 | 3.5 ± .4 |

Table 12 elaborates on the results of Table 11, and presents the changes in the left ventricle internal diameter in systole (ΔLVIDs, %). As can be seen in Table 12, the control animals experienced an average increase in LVIDs of about 20-29% over the course of the study, while the implanted animals experienced an average decrease in LVIDs of about 0-9%. Thus, the inventive device may inhibit increases in the internal diameter of the left ventricle in subjects suffering from heart disease, and indeed may reduce the internal diameter of the left ventricle in subjects suffering from heart disease, in some embodiments by up to 10%.

TABLE 12

Change in Left Ventricle Internal Diameter in Systole (ΔLVIDs, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   |       | +23   | +15   | +18   | +28   | +28   | +16   | +16   | +16   |        |        |        |
| C2   |       | +11   | +25   | +27   | +17   | +23   | +20   |       |       |        |        |        |
| C4   |       | +37   | +43   | +46   |       |       |       |       |       |        |        |        |
| S1   |       | +13   | +17   | +22   | +17   |       | +24   | +26   | +27   |        | +29    | +28    |
| V1   |       | −1    | −2    | +1    | −11   | −8    | −6    | +4    | +1    | +2     | −2     | −10    |
| V2   |       | −18   | −21   | −19   | −14   | −17   | −17   | −17   | −14   |        |        |        |
| V3   |       | +17   | +13   | +8    | +7    | +1    | −2    | +7    | +10   | +10    | +2     | −4     |
| V4   |       | +19   | +9    | −2    | −9    | −12   | −7    | −8    | −9    | −8     | −6     | −14    |
| M.C. |       | +21 ± 6 | +25 ± 6 | +28 ± 6 | +21 ± 4 | 25 ± 2 | +20 ± 2 | +21 ± 5 | +22 ± 6 |    | +29 | +28 |
| M.V. |       | +4 ± 9 | +0 ± 8 | −3 ± 6 | −7 ± 5 | −9 ± 4 | −8 ± 3 | −4 ± 6 | −3 ± 5 | +1 ± 5 | −2 ± 2 | −9 ± 3 |

Table 13 presents the study's results pertaining to ejection fraction (EF, %). The EF of the control animals may be seen to decline significantly over the course of the study, while the EF of the implanted animals increases significantly over the course of the study. For example, it may be seen that for the control animals, C1 experienced a decline in EF to about 45% of baseline; C2 to about 28% of baseline; C4 to about 47% of baseline; and S1 to about 41% of baseline. By comparison, for the implanted animals, V1 experienced an increase in EF to about 169% of baseline; V2 also to about 169% of baseline; V3 to about 129% of baseline; and V4 to about 127% of baseline. The inventive device thus may not only inhibit decreases in EF of subjects suffering from heart failure, but indeed may increase the EF of such subjects significantly, for example by 25-50%, or even 25-70% or more.

TABLE 13

Ejection Fraction (EF, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 35.5  | 28.9  | 26.8  | 23.5  | 21.0  | 18.3  | 17.8  | 16.4  | 16.0  |        |        |        |
| C2   | 45.3  | 40.1  | 29.1  | 28.0  | 23.6  | 20.9  | 12.7  |       |       |        |        |        |
| C4   | 34.3  | 32.4  | 25.2  | 16.2  |       |       |       |       |       |        |        |        |
| S1   | 33.2  | 27.6  | 26.9  | 25.0  | 22.6  |       | 20.7  | 18.6  | 16.8  |        | 14.8   | 13.7   |
| V1   | 24.5  | 27.3  | 36.1  | 36.6  | 35.9  | 36.0  | 35.7  | 35.7  | 35.6  | 37.7   | 37.8   | 41.4   |
| V2   | 26.4  | 33.2  | 37.3  | 37.2  | 40.5  | 42.0  | 42.9  | 43.0  | 44.6  |        |        |        |
| V3   | 32.6  | 33.6  | 33.3  | 34.5  | 37.2  | 37.2  | 37.9  | 38.2  | 38.9  | 41.0   | 41.8   | 41.9   |
| V4   | 45.3  | 45.7  | 46.0  | 47.5  | 47.9  | 47.8  | 47.9  | 49.7  | 52.7  | 53.2   | 55.5   | 57.5   |
| M.C. | 37.1 ± 2.8 | 32.3 ± 2.8 | 27.0 ± .8 | 23.2 ± 2.5 | 22.4 ± .7 | 19.6 ± 1.3 | 17.0 ± 2.3 | 17.5 ± 1.1 | 16.4 ± .4 |  | 14.8 | 13.7 |
| M.V. | 32.2 ± 4.7 | 34.9 ± 3.9 | 38.2 ± 2.7 | 39.0 ± 2.9 | 40.4 ± 2.7 | 40.8 ± 2.7 | 41.1 ± 2.7 | 41.6 ± 3.1 | 42.9 ± 3.7 | 44.0 ± 4.7 | 45.0 ± 5.4 | 46.9 ± 5.3 |

Table 14 elaborates on the results presented in Table 14, and presents the change in ejection fraction. As can be seen in Table 14, the EF of each of the control animals decreased significantly relative to baseline, e.g., by up to 72% for animal C2, while the EF for each of the implanted animals increased significantly.

As noted above with respect to Table 10, the left ventricle internal diameter in diastole (LVIDd) did not significantly change for the implanted animals over the course of the study. Absent such a decrease in the LVIDd, an increase in the EF may be interpreted as an increase in cardiac output. The inventive device thus may not only inhibit decreases in cardiac output of subjects suffering from heart failure, but indeed may increase the cardiac output of such subjects significantly.

TABLE 14

Change in Ejection Fraction (EF, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   |       | −18   | −24   | −34   | −41   | −48   | −50   | −54   | −55   |        |        |        |
| C2   |       | −11   | −36   | −38   | −48   | −54   | −72   |       |       |        |        |        |
| C4   |       | −6    | −19   | −53   |       |       |       |       |       |        |        |        |
| S1   |       | −17   | −27   | −25   | −32   | −38   | −44   | −49   | −55   | −59    |        |        |
| V1   |       | +11   | +47   | +49   | +46   | +47   | +46   | +45   | +45   | +54    | +54    | +69    |
| V2   |       | +26   | +42   | +41   | +54   | +59   | +63   | +63   | +69   |        |        |        |
| V3   |       | +3    | +2    | +6    | +14   | +14   | +16   | +17   | +19   | +26    | +28    | +29    |
| V4   |       | +1    | +2    | +5    | +6    | +6    | +6    | +10   | +16   | +18    | +23    | +27    |
| M.C. |       | −13 ± 3 | −26 ± 4 | −37 ± 6 | −40 ± 5 | −51 ± 3 | −53 ± 10 | −49 ± 5 | −52 ± 3 | −55 | −59 |        |
| M.V. |       | +10 ± 6 | +23 ± 2 | +25 ± 12 | +30 ± 12 | +32 ± 13 | +33 ± 13 | +34 ± 12 | +38 ± 12 | +32 ± 11 | +35 ± 10 | +41 ± 14 |

Table 15 presents the study's results pertaining to fractional shortening (FS, %). Similar to ejection fraction discussed above with respect to Tables 13-14, the FS of each of the control animals may be seen in Table 15 to decline significantly over the course of the study. For example, animal C1 experienced a decline in FS to about 47% of baseline before death; animal C2 to about 24% of baseline; animal C4 to about 46% of baseline; and animal S1 to about 39% of baseline. In contrast, the FS of each of the implanted animals increased significantly over the course of the study. For example, animal V1 experienced an increase in FS to about 183% of baseline; animal V2 to about 166% of baseline; animal V3 to about 132% of baseline; and animal V4 to about 127% of baseline. Thus, the inventive device not only inhibits decreases in fractional shortening for subjects suffering from heart failure, but also may increase fractional shortening significantly, e.g., by about 25-85% of baseline.

TABLE 15

Fractional Shortening (FS, %)

|      | Day 0 | Wk. 1 | Wk. 2 | Wk. 3 | Wk. 4 | Wk. 5 | Wk. 6 | Wk. 8 | Wk. 9 | Wk. 10 | Wk. 11 | Wk. 12 |
|------|-------|-------|-------|-------|-------|-------|-------|-------|-------|--------|--------|--------|
| C1   | 17.0  | 13.7  | 12.5  | 10.9  | 9.7   | 8.4   | 8.0   | 7.5   | 8.0   |        |        |        |
| C2   | 23.2  | 19.3  | 13.5  | 13.0  | 10.7  | 9.1   | 5.5   |       |       |        |        |        |
| C4   | 16.2  | 15.5  | 11.8  | 7.4   |       |       |       |       |       |        |        |        |
| S1   | 15.6  | 12.8  | 12.5  | 11.6  | 10.3  |       | 9.4   | 8.4   | 7.6   |        | 6.6    | 6.1    |
| V1   | 10.9  | 12.6  | 17.1  | 17.5  | 16.9  | 16.9  | 16.9  | 17.0  | 16.9  | 18.1   | 17.6   | 20.0   |
| V2   | 12.4  | 15.8  | 18.1  | 19.0  | 19.9  | 20.7  | 21.2  | 21.6  | 20.6  |        |        |        |
| V3   | 15.7  | 16.4  | 16.2  | 16.7  | 18.3  | 18.2  | 18.5  | 18.8  | 19.3  | 20.5   | 20.8   | 20.8   |
| V4   | 22.4  | 22.6  | 22.9  | 23.7  | 23.7  | 23.6  | 23.8  | 24.9  | 26.7  | 27.1   | 28.8   | 28.4   |
| M.C. | 18.0 ± 1.8 | 15.3 ± 1.4 | 12.6 ± 0.4 | 10.7 ± 1.2 | 10.2 ± 0.3 | 8.7 ± 0.4 | 7.7 ± 1.2 | 8.0 ± 0.4 | 7.8 ± 0.2 |  | 6.6 | 6.1 |
| M.V. | 15.3 ± 2.5 | 16.8 ± 2.1 | 18.6 ± 1.5 | 19.2 ± 1.6 | 19.7 ± 1.5 | 19.8 ± 1.5 | 20.1 ± 1.5 | 20.6 ± 1.7 | 20.9 ± 2.1 | 21.9 ± 2.7 | 22.4 ± 3.3 | 23.1 ± 2.7 |

As the foregoing results illustrate, devices constructed and implanted according to the present invention may provide for significantly improved mortality rates in subjects suffering from heart failure. In particular, the devices may significantly enhance ejection fraction, fractional shortening, and/or cardiac output in subjects who would otherwise have significantly diminished cardiac function as a result of excessive left atrial and left ventricular pressures. For example, subjects may be classified under the New York Heart Association (NYHA) classification system as having Class II (Mild) heart failure, who have slight limitation of physical activity and are comfortable at rest, but for whom ordinary physical activity results in fatigue, palpitation, or dyspnea; Class III (Moderate) heart failure, who have marked limitation of physical activity, may be comfortable at rest, and may experience fatigue, palpitation, or dyspnea if they engage in less than normal activity; or as having Class IV (Severe) heart failure, who are unable to carry out any physical activity without discomfort, exhibit symptoms of cardiac insufficiency at rest, and have increased discomfort if they undertake any physical activity. The present devices may significantly increase the cardiac output of such class III or class IV subjects, particularly those with low ejection fraction, enabling them to engage in significantly more physical activity than they otherwise could. The present devices further may decrease pulmonary artery pressure in subjects with left heart failure, and additionally may reduce or inhibit pulmonary congestion in patients with pulmonary congestion resulting from such heart failure, for example by inhibiting episodes of acute pulmonary edema. Indeed, as the above-described Example illustrates, the inventive device may reduce LAP and PAP significantly relative to what those pressures would otherwise be; such pressure reductions may not only provide immediate relief from acute symptoms, but further may facilitate cardiac remodeling over the weeks following implant and thus provide for enhanced cardiac function. The devices may in some embodiments include means for measuring the various parameters of interest, e.g., means such as discussed above with respect to the animal trials.

Delivery System

Referring to FIGS. 12A and 12B, apparatus 1200 is provided for delivering devices of the present invention, e.g., device 100 of FIGS. 1A to 1D, device 800 of FIGS. 8A to 8C, device 900 of FIG. 9, and/or devices described in U.S. Patent Publication No. 2013/0030521 to Nitzan, assigned to the assignee of the present invention, the entire contents of which are incorporated herein by reference. Apparatus 1200 may include distal end 1202, catheter 1204, and proximal end 1206 having handle 1208. Distal end 1202 comprises components suitable for coupling apparatus 1200 to devices of the present invention, as described in detail below. Catheter 1204 comprises a biocompatible tube shaft of suitable size, e.g., approximately 14 Fr., and suitable length, e.g., approximately 75-100 cm and preferably 85 cm. Proximal end 1206 comprises handle 1208 that is configured to be manipulated, e.g., by a human hand, to transition components in distal end 1202 from an engaged position shown in FIG. 12A to a disengaged position shown in FIG. 12B. Handle 1208 may be manipulated, for example, by moving finger grips 1210 proximally from a locked position shown in FIG. 12A to an unlocked position shown in FIG. 12B. In addition, handle 1208 may be manipulated by moving finger grips 1210 distally from the locked position to the unlocked position so as to transition components in distal end 1202 from the disengaged position to the engaged position to load devices of the present invention.

FIGS. 13A and 13B illustrate distal end 1202 in the engaged position of FIG. 12A and the disengaged position of FIG. 12B, respectively. At distal end 1202, apparatus 1200 may include latching legs 1212, 1214, and 1216 having hook portions 1218, 1220, and 1222, respectively. Latching legs 1212, 1214, and 1216 comprise a biocompatible material such as a biocompatible metal or polymer, and are positioned longitudinally and radially so as to firmly secure devices of the present invention for delivery. Hook portions 1218, 1220, and 1222 extend outwardly from the distal end of latching legs 1212, 1214, and 1216, respectively, and are configured to fit securely between struts and rings of the devices of the present invention. Preferably, hook portions 1218, 1220, and 1222 hook outwardly away from center axis 1223 of catheter 1204 in both the engaged and disengaged positions as shown in FIGS. 12A and 12B. Center axis 1223 is centered relative to catheter 1204 on both a longitudinal and cross-sectional basis. By facing outwardly from center axis 1223, hook portions 1218, 1220, and 1222 may engage the inner surface of the device, e.g., within a lumen of a shunt. In one embodiment, hook portions 1218, 1220, and 1222 hook generally perpendicularly away from center axis 1223 from a radial perspective. As will be readily understood by one of ordinary skill in the art, while three latching legs are illustrated, more or fewer latching legs may be used without departing from the scope of the present invention. For example, one, two, four, five, six, or more latching legs may be used. Catheter 1204 may include catheter end 1224 which may have a larger diameter than the remaining shaft of catheter 1204. Catheter end 1224 comprises a biocompatible material such as a biocompatible metal or polymer, and may be the same or different material than the remaining shaft of catheter 1204. Components at distal end 1202, such as latching legs 1212, 1214, and 1216, may be at least partially disposed within catheter end 1224.

Referring now to FIGS. 14A to 14D, the inner components at distal end 1202 of apparatus 1200 are illustrated. FIGS. 14A and 14B respectively illustrate distal end 1202 in the engaged position of FIGS. 12A and 13A and the disengaged position of FIGS. 12B and 13B. As shown in FIG. 14A, catheter 1204 and catheter end 1224 comprise lumens 1226 and 1228, respectively, for housing the inner components. Latching legs 1212 and 1214 share common ramp portion 1230 having inner section 1232 and outer section 1234 while latching leg 1216 has separate ramp portion 1236 having inner section 1238 and outer section 1240. Inner sections 1232 and 1238 are angled so as to be positioned closer to the central axis of catheter 1204 and catheter end 1224 relative to the positions of outer sections 1234 and 1240. Latching legs may also include jogs and protrusions. For example, latching leg 1216 illustratively includes protrusion 1242 proximal to ramp portion 1236, and jog 1244 between hook portion 1222 and ramp portion 1236. Protrusion 1242 is configured to contact the distal surface of annular member 1248 to maintain suitable positioning of latching leg 1216. Jog 1244 is shaped to prevent release ring 1246 from moving too distally.

Release ring 1246 is coupled to latching legs 1212, 1214, and 1216. For example, latching legs 1212, 1214, and 1216 may be partially disposed within release ring 1246 as illustrated in FIGS. 14A to 14D. Release ring 1246 is moveable within catheter end 1224. Release ring 1246 may be located in a first position, e.g., an engaged position, where release ring 1246 contacts inner sections 1232 and 1238 of ramp portions 1230 and 1236 such that latching legs 1212, 1214, and 1216 extend radially outward as shown in FIGS. 14A and 14C. Release ring 1246 may be moved to a second position, e.g., a disengaged position, where release ring 1246 contacts outer sections 1234 and 1240 of ramp portions 1230 and 1236 such that latching legs 1212, 1214, and 1216 move radially inward as shown in FIGS. 14B and 14D. In one embodiment, release ring 1246 is configured to move from the second position to the first position to load a device of the present invention and to move from the first position to the second position to release the device.

Annular member 1248 may be partially disposed in the proximal end of catheter end 1224 and configured to couple catheter end 1224 to catheter 1204 via a suitable coupling mechanism, e.g., teeth 1250, ribs. Annular member 1248 includes lumen 1252 sized to accept pull chord 1254 therethrough.

Pull chord 1254 is coupled to release ring 1246 and actuation of pull chord 1254 moves release ring 1246 from the first position shown in FIG. 14A to the second position shown in FIG. 14B, and vice versa. In a preferred embodiment, pull chord 1254 is coupled to handle 1208 such that pull chord 1254 is actuated by moving finger grips 1210 from a locked position shown in FIG. 12A to an unlocked position shown in FIG. 12B, and vice versa.

Pull chord 1254 may be coupled to release ring 1246 via release ring base 1256. In this embodiment, release ring base 1256 is directly coupled to release ring 1246 and pull chord 1254 such that actuation of pull chord 1254 moves release ring base 1256 to move release ring 1246 from the first position the second position, and vice versa.

Spring 1258 may be coupled to the proximal surface of release ring base 1256 and the distal surface of annular member 1248 such that release ring base 1256 and annular member 1248 maintain spring 1258 therebetween. Spring 1258 is configured to bias release ring 1246 towards a particular position such as towards the first position as shown in FIG. 14A.

FIGS. 14A and 14C illustrate the components at distal end 1202 in an engaged position, where FIG. 14C omits catheter end 1224 for clarity. As pull chord 1254 is actuated, e.g., via handle 1208, release ring 1246 is moved, e.g., via release ring base 1256, from the engaged position to the disengaged position shown in FIGS. 14B and 14D, where FIG. 14D omits catheter end 1224 for clarity. Release ring 1246 slides along ramp portions 1230 and 1236 from inner sections 1232 and 1238 to outer sections 1234 and 1240 such that latching legs 1212, 1214, and 1216 move from being extended radially outward to being positioned radially inward. As release ring 1246 moves from the engaged position to the disengaged position, spring 1258 is compressed and as release ring 1246 moves from the disengaged position to the engaged position, spring 1258 is decompressed.

FIG. 15A illustrates the components at distal end 1202 of apparatus 1200 engaged to an exemplary device of the present invention and FIG. 15B illustrates the components disengaged from the exemplary device. Device 1500 includes rings 1502 and struts 1504 and may be constructed similar to device 100 of FIGS. 1A to 1D, device 800 of FIGS. 8A to 8C, device 900 of FIG. 9, and/or devices described in U.S. Patent Publication No. 2013/0030521 to Nitzan. As shown in FIG. 15A, latching legs 1212, 1214, and 1216 are sized, shaped, angled, and spaced apart from one another so as to engage device 1500 in openings between rings 1502 and struts 1504 when device 1500 is in a contracted, delivery state. Hook portions 1218, 1220, and 1222 also are sized, shaped, and angled to fit between rings 1502 and struts 1504 and hook portions 1218, 1220, 1222 hook outwardly away from the center axis at the distal end of the delivery apparatus such that hook portions 1218, 1220, 1222 are disposed in the lumen of device 1500 in the disengaged position of FIG. 15B and engage at the inner surface of device 1500. As shown in FIG. 15B, latching legs 1212, 1214, and 1216 are configured to move radially inward a sufficient distance to decouple hook portions 1218, 1220, and 1222 from device 1500 in the disengaged position, thereby releasing device 1500 for implantation.

Exemplary method 1600 of delivering device 100 illustrated in FIGS. 1A-1D to reduce left atrial pressure in a subject, for example, a human having CHF, using apparatus 1200 illustrated in FIGS. 12A-12B will now be described with reference to FIG. 16. Some of the steps of method 1600 may be further elaborated by referring to FIGS. 17A-17Q.

First, a device and apparatus for delivering the device are provided (step 1601). The device may be an hourglass-shaped device having a plurality of sinusoidal rings connected by longitudinally extending struts that define first and second flared end regions and a neck disposed therebetween, as well as an optional tissue valve coupled to the first flared end region. Such a device may be provided, for example, using method 300 described above with respect to FIGS. 3A-3E. The delivery apparatus may be apparatus 1200 illustrated in FIGS. 12A-12B.

Then, the device is collapsed radially to a contracted, delivery state and coupled to the delivery apparatus (step 1602). For example, as illustrated in FIGS. 17A-17C, device 100 may be loaded into loading tube 1700 by first placing device 100 within wide diameter end 1702 of loading tube 1700 as shown in FIG. 17A. Then, using loading tool 1702, device 100 is crimped down within loading tube 1700. Loading tool 1704 includes thin leg end 1706 having two thin legs and wide leg end 1708 having two wide legs. Device 100 may be pushed into loading tube 1700 first by wide leg end 1708 as illustrated in FIG. 17B and then pushed further into loading tube 1700 by thin leg end 1706 as illustrated in FIG. 17C.

In FIG. 17D, device 100 is disposed within thin diameter end 1710 of loading tube 1700. Thin diameter end 1710 has a suitable internal diameter for contracting the device, e.g., approximately 14 Fr. Loading tube 1700 includes tapered section 1712 between wide diameter end 1702 and thin diameter end 1710. Tapered section 1712 facilitates radial compression of device 100 into thin diameter end 1710. Loading tube 1700 is coupled to loading cartridge 1714 via coupling section 1716 having a suitable coupling mechanism, e.g., threads, ribs. Loading cartridge 1714 may be transparent and has a suitable internal diameter, e.g., approximately 14 Fr.

Referring to FIG. 17E, device 100 is pushed into loading cartridge 1714 using pusher 1718. Pusher 1718 has a suitable diameter, e.g., approximately 14 Fr., and may have a "star"-shaped end (not shown). Loading cartridge 1714 is disconnected from loading tube 1700 and connected to hemostatis valve section 1720, which may be a Tuohy Borst valve, as shown in FIG. 17F. Valve section 1720 includes knob 1722 and Y-connector 1724. Distal end 1202 of apparatus 1200 is inserted through knob 1722 of valve section 1720. Knob 1722 and Y-connector 1724 are adjusted to permit movement of apparatus 1200 while maintaining a seal to prevent fluid leakage, e.g., air leakage, blood leakage. The steps shown in FIGS. 17A-17F may be performed while device 100 is immersed in an anticoagulant such as heparinized saline.

FIGS. 17G and 17H illustrate coupling device 100 to apparatus 1200 at distal end 1202. Distal end 1202 is advanced within loading cartridge 1714 toward device 100.

The components of distal end 1202 may be in the disengaged position as illustrated in FIG. 17G. For example, the release ring at distal end 1202 may contact an outer section of the ramp portions of the latching legs such that the latching legs are disposed radially inward. Next, distal end 1202 is moved longitudinally toward device 100 and rotated to align the latching legs with suitable portions of device 100, e.g., at openings between struts and rings of device 100. Once suitable position is achieved, the components of distal end 1202 may move to the engaged position as illustrated in FIG. 17H. For example, the release ring may be moved via a pull chord and handle such that the release ring contacts an inner section of the ramp portions of the latching legs so the latching legs extend radially outward. A clinician may verify that device 100 is engaged to apparatus 1200 by slowing advancing and retracting apparatus 1200 a distance, e.g., approximately 5 mm, while device 100 remains in loading cartridge 1714. In addition, a clinician may verify that apparatus 1200 is capable of disengaging from device 100 within loading cartridge 1714 by pressing handle to cause the components at distal end 1202 to disengage and then moving distal end 1202 away from device 100. After such verification, the clinician may reengage apparatus 1200 to device 100. Preferably, device 100 is loaded into loading cartridge 1714 shortly before implantation, so as to avoid unnecessarily compressing device 100 or re-setting of the closed shape of leaflets 132, which may interfere with later deployment or operation of the device.

Referring back to FIG. 16, the device then is implanted, first by identifying the fossa ovalis of the heart septum, across which device 100 is to be deployed (step 1603). Specifically, a BROCKENBROUGH needle may be percutaneously introduced into the right atrium via the subject's venous vasculature, for example, via the femoral artery. Then, under fluoroscopic or echocardiographic visualization, the needle is pressed against the fossa ovalis, at a pressure insufficient to puncture the fossa ovalis. As illustrated in FIG. 5C, the pressure from needle 530 causes "tenting" of fossa ovalis 541, i.e., causes the fossa ovalis to stretch into the left atrium. Other portions of atrial septum 540 are thick and muscular, and so do not stretch to the same extent as the fossa ovalis. Thus, by visualizing the extent to which different portions of the atrial septum 540 tents under pressure from needle 530, fossa ovalis 541 may be identified, and in particular the central portion of fossa ovalis 541 may be located.

Referring again to FIG. 16, the fossa ovalis (particularly its central region) may be punctured with the BROCKENBROUGH needle, and a guidewire may be inserted through the puncture by threading the guidewire through the needle and then removing the needle (step 1604). The puncture through the fossa ovalis then may be expanded by advancing a dilator over the guidewire. Alternatively, a dilator may be advanced over the BROCKENBROUGH needle, without the need for a guidewire. The dilator is used to further dilate the puncture and a sheath then is advanced over the dilator and through the fossa ovalis; the dilator and guidewire or needle then are removed (step 1605). The sheath, which may be 14 Fr., is then flushed.

Distal end 1202 of apparatus 1200, with device 100 coupled thereto in a contracted, delivery state, then is advanced into the sheath (step 1606). For example, the delivery system may be flushed, e.g., via fluid connected to fluid tube 1730, and then loading cartridge 1714 may be coupled to sheath 1726, e.g., via port 1728, as illustrated in FIG. 17I. The clinician should verify that loading cartridge contains no air therein. Next, while holding sheath 1726 in place, loading cartridge 1714 is advanced distally within port 1728 as illustrated in FIG. 17G. The device and delivery apparatus are advanced distally in sheath 1726 until proximal end 1206 of apparatus 1200 is a predetermined distance X, e.g., approximately 1 cm, from knob 1722 as illustrated in FIG. 17K. The delivery system again may be flushed, e.g., via fluid connected to fluid tube 1730. The engagement of the latching legs of apparatus 1200 with device 100 permit movement of device 100 longitudinally forward and longitudinally backward through sheath 1726.

Then, under fluoroscopic or echocardiographic visualization, sheath 1726 may be repositioned such that the distal tip of sheath 1726 is disposed a predetermined distance, e.g., approximately 1-2 cm, distal to the fossa ovalis towards the left atrium. Next, device 100 and apparatus 1200 are advanced distally such that the device is partially advanced out of the sheath so the second flared end of the device protrudes out of the sheath and into the left atrium, and expands to its deployed state (step 1607). For example, device 100 and apparatus 1200 may be advanced distally until the handle at proximal end 1206 contacts knob 1722 as shown in FIG. 17L. Such advancement causes device 100 to partially protrude out of sheath 1726 and into left atrium LA, which causes the second flared end region to expand in the left atrium LA, as shown in FIG. 17M. The neck of device 100 is configured to self-position device 100 within the distal end of sheath 1726 when device 100 is partially deployed. Device 100 may be advanced across the atrial septum AS such that the angle $\theta$ between center axis 1728 of device 100, sheath 1726, apparatus 1200, and/or catheter 1204 and the outer surface of the atrial septum at the left atrial side below device 100 is generally perpendicular, e.g., between about 80 and about 100 degrees, between about 85 and about 95 degrees, or about 90 degrees, as shown in FIG. 17M. Alternatively, device 100 may be positioned across the atrial septum AS, e.g., across a puncture through the fossa ovalis, at a non-perpendicular angle between center axis 1728 and the outer wall of the atrial septum at the left atrial side below device 100. For example, the angle $\theta'$ may be substantially greater than 90 degrees as shown in FIG. 17N. Such an angle may be appropriate when device 100, sheath 1726, apparatus 1200, and/or catheter 1204 are advanced toward the atrial septum transapically or through the inferior vena cava. Exemplary angles $\theta'$ between center axis 1728 and the outer surface of the atrial septum below device 100 include between about 110 and about 170 degrees, between about 120 and about 160 degrees, between about 130 and about 150 degrees about 120 degrees, about 125 degrees, about 130 degrees, about 135 degrees, about 140 degrees, about 145 degrees, about 150 degrees, about 155 degrees, about 160 degrees, about 165 degrees, and about 170 degrees.

As another example, the angle $\theta''$ may be substantially less than 90 degrees as shown in FIG. 17O. Such an angle may be appropriate when device 100, sheath 1726, apparatus 1200, and/or catheter 1204 are advanced toward the atrial septum through the superior vena cava. Exemplary angles $\theta''$ between center axis 1728 and the outer surface of the atrial septum at the left atrial side below device 100 include between about 10 and about 70 degrees, between about 20 and about 60 degrees, between about 30 and about 50 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, and about 70 degrees.

An hourglass shape may aid in non-perpendicular deployment because the flared ends of the device engage the atrial septum, even when positioned at an angle relative to the central axis of the puncture through the atrial septum.

Next, under fluoroscopic or echocardiographic visualization, it is verified that the second flared end of the device protrudes from sheath 1726 and then knob 1722 is used to lock the delivery system in place. Sheath 1726 is pulled proximally to perform "back tenting," causing the second flared end region of device 100 to engage the left side of the atrial septum AS as shown in FIG. 17M. Such a feature may prevent accidentally deploying the entire device in the left atrium LA and may assist in positioning the device when advanced at non-perpendicular angles as described in FIGS. 17N and 17O.

Using fluoroscopic or echocardiographic visualization, the clinician next verifies that the device is positioned across the fossa ovalis. The clinician then reduces the pulling force of the sheath and allows the fossa ovalis to straighten. Then, while holding sheath 1726 in place, knob 1722 is released and the components at distal end 1202 of apparatus 1200 are moved from an engaged position to a disengaged position, e.g., by actuating handle 1208 as shown in FIG. 17P. Then, apparatus 1200 is pulled proximally a predetermined distance, e.g., approximately 5-6 cm.

The device then may be fully deployed by pulling the sheath proximally causing the second flared end region to flank the left side of the atrial septum and the neck of the device to lodge in the puncture through the fossa ovalis, and allowing expansion of the first flared end of the device into the right atrium as shown in FIG. 17Q (step 1608). Any remaining components of the delivery system then may be removed, e.g., sheath and distal end of delivery apparatus (step 1609). Once positioned in the fossa ovalis, the device shunts blood from the left atrium to the right atrium when the left atrial pressure exceeds the right atrial pressure (step 1610), thus facilitating treatment and/or the amelioration of symptoms associated with CHF.

It should be noted that the inventive devices also may be used with patients having disorders other than heart failure. For example, in one embodiment the device may be implanted in a subject suffering from myocardial infarction, for example in the period immediately following myocardial infarction (e.g., within a few days of the event, or within two weeks of the event, or even within six months of the event). During such a period, the heart remodels to compensate for reduced myocardial function. For some subjects suffering from severe myocardial infarction, such remodeling may cause the function of the left ventricle to significantly deteriorate, which may lead to development of heart failure. Implanting an inventive device during the period immediately following myocardial infarction may inhibit such deterioration in the left ventricle by reducing LAP and LVEDP during the remodeling period. For example, in the above-described Example, heart failure was induced in the sheep by injecting microspheres that block the coronary artery and induce myocardial infarction. Following the myocardial infarction, the sheep developed heart failure. As can be seen in the various results for the implanted animals, implanting the inventive device even a week following the myocardial infarction inhibited degradation of the heart and yielded significantly improved mortality rates and cardiac functioning both immediately and over time as the subjects' hearts remodeled. As such, it is believed that implanting an inventive device for even a few weeks or months following myocardial infarction may provide significant benefits to the subject as their heart remodels. The device optionally then may be removed.

While various illustrative embodiments of the invention are described above, it will be apparent to one skilled in the art that various changes and modifications may be made herein without departing from the invention. It will further be appreciated that the devices described herein may be implanted in other positions in the heart. For example, device 100 illustrated in FIGS. 1A-1D may be implanted in an orientation opposite to that shown in FIG. 2B, so as to shunt blood from the right atrium to the left atrium, thus decreasing right atrial pressure; such a feature may be useful for treating a high right atrial pressure that occurs in pulmonary hypertension. Similarly, device 100 may be implanted across the ventricular septum, in an orientation suitable to shunt blood from the left ventricle to the right ventricle, or in an orientation suitable to shunt blood from the right ventricle to the left ventricle. The appended claims are intended to cover all such changes and modifications that fall within the true spirit and scope of the invention.

What is claimed:

1. An apparatus for coupling to an atrial shunt for regulating blood pressure between a patient's left atrium and right atrium, the apparatus comprising:
   a catheter having a proximal region and a distal region, the distal region sized and shaped to be advanced to the patient's atrial septum;
   one or more latching legs disposed at the distal region of the catheter, the one or more latching legs having a hook portion and a ramp portion disposed proximal to the hook portion;
   a ring coupled to the one or more latching legs;
   an actuator disposed at the proximal region of the catheter, the actuator configured to move the ring between a first position, where the ring contacts a first section of the ramp portion such that the one or more latching legs extend radially outward, and a second position, where the ring contacts a second section of the ramp portion such that the one or more latching legs move radially inward; and
   a ring base coupled to the ring and the actuator, wherein the actuator causes the ring base to move the ring between the first position and the second position.

2. The apparatus of claim 1, wherein the apparatus is configured to deliver the atrial shunt to the atrial septum of the patient such that a first flared end region of the atrial shunt is disposed in the right atrium in an expanded state, a second flared end region of the atrial shunt is disposed in the left atrium in an expanded state, and a neck region between the first and second flared end regions is positioned at the atrial septum.

3. The apparatus of claim 1, wherein the catheter comprises a lumen extending between the proximal region and the distal region of the catheter.

4. The apparatus of claim 3, wherein the one or more latching legs and the ring are at least partially disposed within the lumen.

5. The apparatus of claim 1, further comprising a sheath, wherein the catheter is configured to be at least partially disposed within the sheath.

6. The apparatus of claim 5, wherein the sheath is configured to receive the atrial shunt in a contracted state.

7. The apparatus of claim 1, further comprising a pull chord coupled to the ring, wherein the actuator is configured to move the pull chord to move the ring between the first position and the second position.

8. The apparatus of claim 1 further comprising a spring coupled to the ring base, the spring configured to bias the ring toward the first position.

9. The apparatus of claim 8, further comprising an annular member disposed proximal to the ring base and configured to maintain the spring between the ring base and the annular member.

10. The apparatus of claim 1, wherein the hook portion of the one or more latching legs hooks outwardly away from a center axis of the catheter.

11. An apparatus for coupling to an atrial shunt for regulating blood pressure between a patient's left atrium and right atrium, the apparatus comprising:
a catheter having a proximal region and a distal region, the distal region sized and shaped to be advanced to the patient's atrial septum;
one or more latching legs disposed at the distal region of the catheter, the one or more latching legs having a hook portion and a ramp portion disposed proximal to the hook portion, the one or more latching legs comprising two latching legs that share a common ramp portion and a third latching leg having a separate ramp portion;
a ring coupled to the one or more latching legs; and
an actuator disposed at the proximal region of the catheter, the actuator configured to move the ring between a first position, where the ring contacts a first section of the ramp portion such that the one or more latching legs extend radially outward, and a second position, where the ring contacts a second section of the ramp portion such that the one or more latching legs move radially inward.

12. The apparatus of claim 11, further comprising a pull chord coupled to the ring, wherein the actuator is configured to move the pull chord to move the ring between the first position and the second position.

13. A method of coupling to an atrial shunt configured for implantation at an atrial septum, the method comprising:
advancing a distal region of a catheter of an apparatus to the atrial septum, the apparatus further comprising an actuator at a proximal region of the catheter, one or more latching legs disposed at the distal region of the catheter and having a hook portion and a ramp portion disposed proximal to the hook portion, the one or more latching legs configured to move the atrial shunt longitudinally forward and longitudinally backward through a sheath, and a ring coupled to the one or more latching legs; and
actuating the actuator to move the ring between a first position, where the ring contacts a first section of the ramp portion such that the one or more latching legs extend radially outward, and a second position, where the ring contacts a second section of the ramp portion such that the one or more latching legs move radially inward.

14. The method of claim 13, wherein the advancing further comprises advancing the atrial shunt in the sheath, the method further comprising:
expanding a second flared end of the atrial shunt from the sheath such that the atrial shunt engages the left side of the atrial septum; and
retracting the sheath such that a first flared end of the atrial shunt expands and is disposed in a right atrium.

15. The method of claim 13, wherein the atrial shunt is configured for implantation at an atrial septum of a patient having a heart pathology comprising at least one of heart failure, pulmonary congestion, pulmonary hypertension, or myocardial infarction.

16. A method of coupling to an atrial shunt configured for implantation at an atrial septum, the method comprising:
advancing a distal region of a catheter of an apparatus to the atrial septum, the apparatus further comprising an actuator at a proximal region of the catheter, one or more latching legs disposed at the distal region of the catheter and having a hook portion and a ramp portion disposed proximal to the hook portion, and a ring coupled to the one or more latching legs;
actuating the actuator to move the ring between a first position, where the ring contacts a first section of the ramp portion such that the one or more latching legs extend radially outward, and a second position, where the ring contacts a second section of the ramp portion such that the one or more latching legs move radially inward; and
positioning the atrial shunt across a puncture through a fossa ovalis such that a neck region of the atrial shunt is positioned in the puncture, and wherein a first flared end region of the atrial shunt is disposed in a right atrium in an expanded state and a second flared end region is disposed in a left atrium in an expanded state.

17. The method of claim 16, wherein positioning the atrial shunt comprises positioning the atrial shunt across the puncture through the fossa ovalis at a non-perpendicular angle between a center axis of the catheter and an outer wall of the atrial septum.

18. The method of claim 16, wherein positioning the atrial shunt comprises back tenting the fossa ovalis by pulling the apparatus proximally such that the expanded second flared end of the atrial shunt at least partially engages an outer wall of the fossa ovalis.

19. A method of coupling to an atrial shunt configured for implantation at an atrial septum, the method comprising:
identifying a middle of a fossa ovalis of the atrial septum by pressing a needle against the fossa ovalis to partially tent the fossa ovalis, and puncturing the middle of the fossa ovalis with the needle such that the atrial shunt is deployed away from a limbus, an atrial wall, and a ridge between an inferior vena cava and coronary sinus;
advancing a distal region of a catheter of an apparatus to the atrial septum, the apparatus further comprising an actuator at a proximal region of the catheter, one or more latching legs disposed at the distal region of the catheter and having a hook portion and a ramp portion disposed proximal to the hook portion, and a ring coupled to the one or more latching legs; and
actuating the actuator to move the ring between a first position, where the ring contacts a first section of the ramp portion such that the one or more latching legs extend radially outward, and a second position, where the ring contacts a second section of the ramp portion such that the one or more latching legs move radially inward.

20. The method of claim 19, wherein actuating the actuator to move the ring between the first position and the second position comprises actuating the actuator to move a pull chord coupled to the ring to move the ring between the first position and the second position.

* * * * *